United States Patent
Strum et al.

(10) Patent No.: US 11,364,222 B2
(45) Date of Patent: Jun. 21, 2022

(54) COMBINATION THERAPY FOR TREATMENT OF CANCER

(71) Applicants: G1 Therapeutics, Inc., Research Triangle Park, NC (US); The Board of Trustees of the University of Illinois, Urbana, IL (US)

(72) Inventors: Jay C. Strum, Hillsborough, NC (US); Gregory R. Thatcher, Urbana, IL (US); Rui Xiong, Urbana, IL (US); Jiong Zhao, Urbana, IL (US); Debra A. Tonetti, Urbana, IL (US)

(73) Assignee: G1 Therapeutics, Inc., Research Triangle Park, NC (US)

( * ) Notice: Subject to any disclaimer, the term of this patent is extended or adjusted under 35 U.S.C. 154(b) by 214 days.

(21) Appl. No.: 16/460,502

(22) Filed: Jul. 2, 2019

(65) Prior Publication Data

US 2019/0321332 A1   Oct. 24, 2019

Related U.S. Application Data

(63) Continuation of application No. PCT/US2018/012675, filed on Jan. 5, 2018.

(60) Provisional application No. 62/443,588, filed on Jan. 6, 2017.

(51) Int. Cl.
*A61K 31/381* (2006.01)
*A61P 35/00* (2006.01)
*A61K 31/519* (2006.01)
*A61K 31/5377* (2006.01)

(52) U.S. Cl.
CPC .......... *A61K 31/381* (2013.01); *A61K 31/519* (2013.01); *A61K 31/5377* (2013.01); *A61P 35/00* (2018.01)

(58) Field of Classification Search
None
See application file for complete search history.

(56) References Cited

U.S. PATENT DOCUMENTS

| | | |
|---|---|---|
| 4,133,814 A | 1/1979 | Jones et al. |
| 4,418,068 A | 11/1983 | Jones |
| 4,659,516 A | 4/1987 | Bowler et al. |
| 5,393,763 A | 2/1995 | Black et al. |
| 5,457,117 A | 10/1995 | Black et al. |
| 5,478,847 A | 12/1995 | Draper |
| 5,491,123 A | 2/1996 | Hagen et al. |
| 5,780,497 A | 7/1998 | Miller et al. |
| 5,880,137 A | 3/1999 | Miller et al. |
| 5,998,402 A | 12/1999 | Miller et al. |
| 6,005,102 A | 12/1999 | Raveendranath et al. |
| 6,326,392 B1 | 12/2001 | Gast et al. |
| 6,403,614 B1 | 6/2002 | Dodge et al. |
| 6,479,535 B1 | 11/2002 | Pickar et al. |
| 6,512,002 B2 | 1/2003 | Lee et al. |
| 6,583,170 B1 | 6/2003 | Pickar et al. |
| 6,632,834 B2 | 10/2003 | Thompson et al. |
| 6,756,401 B2 | 6/2004 | Day et al. |
| 6,777,424 B2 | 8/2004 | Littman et al. |
| 6,797,719 B2 | 9/2004 | Arbuthnot et al. |
| 6,821,989 B2 | 11/2004 | Rosati |
| 6,962,993 B2 | 11/2005 | Blumenkopf et al. |
| 7,345,171 B2 | 3/2008 | Beylin et al. |
| 7,371,774 B2 | 5/2008 | Moinet |
| 8,030,330 B2 | 10/2011 | Arbuthnot et al. |
| 8,455,534 B2 | 6/2013 | Smith et al. |
| 8,598,186 B2 | 12/2013 | Tavares et al. |
| 8,598,197 B2 | 12/2013 | Tavares et al. |
| 8,642,632 B2 | 2/2014 | Miller |
| 8,691,830 B2 | 4/2014 | Tavares et al. |
| 8,703,810 B2 | 4/2014 | Kahraman et al. |
| 8,822,683 B2 | 9/2014 | Tavares et al. |
| 8,829,012 B2 | 9/2014 | Tavares et al. |
| 8,853,423 B2 | 10/2014 | Govek et al. |
| 9,078,871 B2 | 7/2015 | Kahraman et al. |
| 9,102,682 B2 | 8/2015 | Tavares et al. |
| 9,193,714 B2 | 11/2015 | Smith et al. |
| 9,260,442 B2 | 2/2016 | Tavares |
| 9,464,092 B2 | 10/2016 | Strum et al. |
| 9,475,798 B2 | 10/2016 | Govek et al. |
| 9,481,691 B2 | 11/2016 | Tavares et al. |
| 9,487,530 B2 | 11/2016 | Strum et al. |
| 9,499,564 B2 | 11/2016 | Tavares et al. |
| 9,527,857 B2 | 12/2016 | Strum et al. |
| 9,717,735 B2 | 8/2017 | Strum et al. |
| 9,745,316 B2 | 8/2017 | Tavares |
| 9,856,268 B2 | 1/2018 | Tavares |
| 9,931,345 B2 | 4/2018 | Strum et al. |
| 9,957,276 B2 | 5/2018 | Tavares et al. |
| 10,076,523 B2 | 9/2018 | Strum et al. |
| 10,085,992 B2 | 10/2018 | Strum et al. |
| 10,087,191 B2 | 10/2018 | Yu et al. |
| 10,118,910 B2 | 11/2018 | Thatcher et al. |
| 10,189,849 B2 | 1/2019 | Tavares et al. |
| 10,189,850 B2 | 1/2019 | Tavares et al. |
| 10,189,851 B2 | 1/2019 | Tavares et al. |
| 10,208,011 B2 | 2/2019 | Strum et al. |
| 10,231,969 B2 | 3/2019 | Strum et al. |

(Continued)

FOREIGN PATENT DOCUMENTS

| | | |
|---|---|---|
| EP | 545478 A1 | 6/1993 |
| EP | 551849 A1 | 7/1993 |
| EP | 622673 A1 | 11/1994 |
| EP | 752421 A1 | 1/1997 |
| EP | 802184 B1 | 6/2002 |
| EP | 1947085 A1 | 7/2008 |
| GB | 2483736 A | 3/2012 |
| JP | 2005-129430 A | 5/2005 |

(Continued)

OTHER PUBLICATIONS

Abdelhamid et al., "Benzothiophene Selective Estrogen Receptor Modulators Provide Neuroprotection by a Novel GPR30-Dependent Mechanism" ACS Chem. Neuro., Mar. 16, 2011; 2: 256-268.

(Continued)

*Primary Examiner* — Savitha M Rao
*Assistant Examiner* — Gregg Polansky
(74) *Attorney, Agent, or Firm* — Knowles Intellectual Property Strategies, LLC

(57) ABSTRACT

Compositions, combinations and methods comprising a CDK4/6 inhibitor of Formula D with a selective estrogen receptor downregulator of Formula A, B or C that are advantageous for the treatment of abnormal cellular proliferation, including a cancer or a tumor.

32 Claims, 20 Drawing Sheets

(56) References Cited

U.S. PATENT DOCUMENTS

| | | | |
|---|---|---|---|
| 10,376,519 | B2 | 8/2019 | Strum et al. |
| 10,377,735 | B2 | 8/2019 | Thatcher et al. |
| 10,413,547 | B2 | 9/2019 | Strum et al. |
| 10,434,104 | B2 | 10/2019 | Strum et al. |
| 10,464,940 | B2 | 11/2019 | Tavares et al. |
| 10,519,148 | B2 | 12/2019 | Guan et al. |
| 10,618,905 | B2 | 4/2020 | Strum et al. |
| 10,633,362 | B2 | 4/2020 | Strum et al. |
| 10,654,831 | B2 | 5/2020 | Strum et al. |
| 10,660,896 | B2 | 5/2020 | Strum et al. |
| 10,696,682 | B2 | 6/2020 | Tavares et al. |
| 10,703,747 | B2 | 7/2020 | Thatcher et al. |
| 10,709,711 | B2 | 7/2020 | Strum et al. |
| 10,807,964 | B2 | 10/2020 | Thatcher et al. |
| 10,829,490 | B2 | 11/2020 | Strum et al. |
| 10,925,878 | B2 | 2/2021 | Strum et al. |
| 10,966,984 | B2 | 4/2021 | Strum et al. |
| 10,981,887 | B2 | 4/2021 | Strum et al. |
| 10,988,479 | B1 | 4/2021 | Schneider et al. |
| 11,040,042 | B2 | 6/2021 | Strum et al. |
| 2001/0056099 | A1 | 12/2001 | Day et al. |
| 2002/0013327 | A1 | 1/2002 | Lee et al. |
| 2002/0016340 | A1 | 2/2002 | Rosati |
| 2002/0128276 | A1 | 9/2002 | Day et al. |
| 2004/0044059 | A1 | 3/2004 | Pinney et al. |
| 2004/0236084 | A1 | 11/2004 | Biwersi et al. |
| 2005/0240017 | A1 | 10/2005 | Wallace |
| 2007/0112009 | A1 | 5/2007 | Lafay et al. |
| 2011/0009353 | A1 | 1/2011 | Chen-Kiang et al. |
| 2011/0312909 | A1 | 12/2011 | Ciomei et al. |
| 2012/0071535 | A1 | 3/2012 | Smith et al. |
| 2013/0116232 | A1 | 5/2013 | Kahraman et al. |
| 2013/0178445 | A1 | 7/2013 | Kushner et al. |
| 2014/0235660 | A1 | 8/2014 | Burks et al. |
| 2014/0378422 | A1 | 12/2014 | Catheme et al. |
| 2015/0005286 | A1 | 1/2015 | Smith et al. |
| 2015/0080438 | A1 | 3/2015 | Wintermantel et al. |
| 2015/0246926 | A1 | 9/2015 | Tavares et al. |
| 2015/0258080 | A1 | 9/2015 | Hager et al. |
| 2015/0284357 | A1 | 10/2015 | Thatcher et al. |
| 2015/0291552 | A1 | 10/2015 | Thatcher et al. |
| 2016/0090377 | A1 | 3/2016 | Govek et al. |
| 2016/0090378 | A1 | 3/2016 | Kahraman et al. |
| 2016/0108054 | A1 | 4/2016 | Tavares |
| 2016/0175284 | A1 | 6/2016 | Labadie et al. |
| 2016/0175289 | A1 | 6/2016 | Labadie et al. |
| 2016/0304450 | A1 | 10/2016 | Liang et al. |
| 2016/0311805 | A1 | 10/2016 | Kushner et al. |
| 2016/0347742 | A1 | 12/2016 | Labadie et al. |
| 2016/0368911 | A1 | 12/2016 | Campos et al. |
| 2017/0129855 | A1 | 5/2017 | Liang et al. |
| 2017/0166550 | A1 | 6/2017 | Thatcher et al. |
| 2017/0166551 | A1 | 6/2017 | Thatcher et al. |
| 2018/0360840 | A1 | 12/2018 | Strum et al. |
| 2019/0070185 | A1 | 3/2019 | Strum et al. |
| 2019/0119292 | A1 | 4/2019 | Tavares et al. |
| 2019/0125752 | A1 | 5/2019 | Strum et al. |
| 2019/0135820 | A1 | 5/2019 | Smith et al. |
| 2019/0151311 | A1 | 5/2019 | Strum et al. |
| 2019/0167691 | A1 | 6/2019 | Strum et al. |
| 2019/0321370 | A1 | 10/2019 | Sorrentino et al. |
| 2019/0374545 | A1 | 12/2019 | Sorrentino et al. |
| 2020/0022983 | A1 | 1/2020 | Strum et al. |
| 2020/0123126 | A1 | 4/2020 | Thatcher et al. |
| 2020/0123168 | A1 | 4/2020 | Smith et al. |
| 2020/0239486 | A1 | 7/2020 | Strum et al. |
| 2020/0277300 | A1 | 9/2020 | Tavares et al. |
| 2020/0283406 | A1 | 9/2020 | Strum et al. |
| 2020/0331925 | A1 | 10/2020 | Strum et al. |
| 2020/0345743 | A1 | 11/2020 | Strum et al. |
| 2020/0405721 | A1 | 12/2020 | Beelen et al. |
| 2021/0030758 | A1 | 2/2021 | Strum et al. |
| 2021/0047328 | A1 | 2/2021 | Strum et al. |
| 2021/0077498 | A1 | 3/2021 | Strum et al. |
| 2021/0122755 | A1 | 4/2021 | Smith et al. |
| 2021/0171554 | A1 | 6/2021 | Strum et al. |
| 2021/0179567 | A1 | 6/2021 | Schneider et al. |
| 2021/0213022 | A1 | 7/2021 | Strum et al. |
| 2021/0267986 | A1 | 9/2021 | Sorrentino et al. |
| 2021/0299130 | A1 | 9/2021 | Strum et al. |
| 2021/0387993 | A1 | 12/2021 | Schneider et al. |
| 2021/0395259 | A1 | 12/2021 | Tavares et al. |

FOREIGN PATENT DOCUMENTS

| | | |
|---|---|---|
| WO | WO 1998/033798 A2 | 8/1998 |
| WO | WO 1999/015500 A1 | 4/1999 |
| WO | WO 1999/024027 A2 | 5/1999 |
| WO | WO 2002/003975 A2 | 1/2002 |
| WO | WO 2002/003976 A2 | 1/2002 |
| WO | WO 2002/003977 A2 | 1/2002 |
| WO | WO 2002/003986 A2 | 1/2002 |
| WO | WO 2002/003988 A2 | 1/2002 |
| WO | WO 2002/003989 A2 | 1/2002 |
| WO | WO 2002/003990 A2 | 1/2002 |
| WO | WO 2002/003991 A2 | 1/2002 |
| WO | WO 2002/003992 A2 | 1/2002 |
| WO | WO 2002/004418 A2 | 1/2002 |
| WO | WO 2002/013802 A2 | 2/2002 |
| WO | WO 2003/062236 A1 | 7/2003 |
| WO | WO 2005/005426 A1 | 1/2005 |
| WO | WO 2005/016929 A1 | 2/2005 |
| WO | WO 2005/040166 A1 | 5/2005 |
| WO | WO 2005/052147 A2 | 6/2005 |
| WO | WO 2005/105213 A2 | 11/2005 |
| WO | WO 2006/074985 A1 | 7/2006 |
| WO | WO 2006/078834 A1 | 7/2006 |
| WO | WO 2006/084338 A1 | 8/2006 |
| WO | WO 2007/048847 A2 | 5/2007 |
| WO | WO 2007/087684 A1 | 8/2007 |
| WO | WO 2008/002490 A2 | 1/2008 |
| WO | WO 2009/003003 A2 | 12/2008 |
| WO | WO 2009/013195 A1 | 1/2009 |
| WO | WO 2009/085185 A1 | 7/2009 |
| WO | WO 2010/020675 A1 | 2/2010 |
| WO | WO 2010/039997 A2 | 4/2010 |
| WO | WO 2010/051127 A2 | 5/2010 |
| WO | WO 2010/093578 A1 | 8/2010 |
| WO | WO 2010/127452 A1 | 11/2010 |
| WO | WO 2010/132725 A2 | 11/2010 |
| WO | WO 2011/101409 A1 | 8/2011 |
| WO | WO 2011/103485 A1 | 8/2011 |
| WO | WO 2011/139769 A2 | 12/2011 |
| WO | WO 2011/156518 A2 | 12/2011 |
| WO | WO 2012/037410 A2 | 3/2012 |
| WO | WO 2012/037411 A2 | 3/2012 |
| WO | WO 2012/048058 A2 | 4/2012 |
| WO | WO 2012/084711 A1 | 6/2012 |
| WO | WO 2012/061156 A1 | 10/2012 |
| WO | WO 2013/090829 A1 | 6/2013 |
| WO | WO 2013/090836 A1 | 6/2013 |
| WO | WO 2013/090921 A1 | 6/2013 |
| WO | WO 2013/142266 A1 | 9/2013 |
| WO | WO 2013/148748 A1 | 10/2013 |
| WO | WO 2013/163239 A1 | 10/2013 |
| WO | WO 2014/066692 A1 | 5/2014 |
| WO | WO 2014/066695 A1 | 5/2014 |
| WO | WO 2014/130310 A1 | 8/2014 |
| WO | WO 2014/151899 A1 | 9/2014 |
| WO | WO 2014/037842 A1 | 12/2014 |
| WO | WO 2014/191726 A1 | 12/2014 |
| WO | WO 2014/203129 A1 | 12/2014 |
| WO | WO 2014/203132 A1 | 12/2014 |
| WO | WO 2014/205136 A1 | 12/2014 |
| WO | WO 2014/205138 A1 | 12/2014 |
| WO | WO 2015/000867 A1 | 1/2015 |
| WO | WO 2015/028409 A1 | 3/2015 |
| WO | WO 2015/061407 A1 | 4/2015 |
| WO | WO 2015/092634 A1 | 6/2015 |
| WO | WO 2015/136016 A2 | 9/2015 |
| WO | WO 2015/136017 A1 | 9/2015 |
| WO | WO 2015/149045 A1 | 10/2015 |
| WO | WO 2016/097071 A1 | 6/2016 |
| WO | WO 2016/097072 A1 | 6/2016 |

(56) References Cited

FOREIGN PATENT DOCUMENTS

| WO | WO 2016/097073 A1 | 6/2016 |
|---|---|---|
| WO | WO 2016/189011 A1 | 12/2016 |
| WO | WO 2017/056115 A1 | 4/2017 |
| WO | WO 2017/059139 A1 | 4/2017 |
| WO | WO 2017/060326 A1 | 4/2017 |
| WO | WO 2017/072792 A1 | 5/2017 |
| WO | WO 2017/100712 A1 | 6/2017 |

OTHER PUBLICATIONS

Bolton et al., "Genotoxic Estrogen Pathway: Endogenous and Equine Estrogen Hormone Replacement Therapy" The Chemical Biology of DNA Damage, 2010; 185-199.
Bolton et al. "Potential Mechanisms of Estrogen Quinone Carcinogenesis" Chem. Res. Toxicol., 2008, 21: 93-101; Epub Dec. 4, 2007.
Bolton et al. "Quinoids Formed from Estrogens and Antiestrogens", Methods in Enzymology 2004; 378: 110-122.
Chandrasena, et al. "Problematic Detoxification of Estrogen Quinones by NAD(P)H-Dependent Quinone Oxidoreductase and Gluthathione-S-transferase", Chem. Res., Toxicol., 2008, 21, 1324-1329.
Chu et al. "Discovery of [4-Amino-2-(1-methanesulfonylpiperidin-4-ylamino)pyrimidin-5-yl](2,3-difluoro-6- methoxyphenyl)methanone (R547), a potent and selective cyclin-dependent kinase inhibitor with significant in vivo antitumor activity" J Med Chem, Nov. 2, 2006; 49(22): 6549-6560,.
Dowers, et al. Bioactivation of Selective Estrogen Receptor Modulators (SERMs) Chem. Res. Toxicol., 2006, 19: 1125-1137.
Gherezghiher et al. "The Naphthol Selective Estrogen Receptor Modulator (SERM), LY2066948, is Oxidized to an o-quinone Analogous to the Naphthol Equine Estrogen, Equilenin", Chemico-Biological Interactions, 196, (2012); 1-10.
Goldberg et al., "Pyrazinoindolone inhibitors of MAPKAP-K2", Bioogranic & Medicinal Chemistry Letters, Dec. 23, 2007, 18, 938-941.
Guillard et al., "Synthesis and biological evaluations of new pyrrolo[2,3-b]pyrimidine as SDI analogs", Heterocycles, 2008, 75(5), 1163-1189.
Guo et al., "ZB716, a steroidal selective estrogen receptor degrader (SERD), is orally efficacious in blocking tumor growth in mouse xenograft models", Oncotarget, 2018, 9, 6924-693 7.
Gutgesell et al., "Combination therapy of targeted anticancer pathways and estrogen receptor ligands and their responses in de novo and tamoxifen resistant cell models", Poster Presented at San Antonio Breast Cancer Symposium, Dec. 8, 2016.
Gutgesell et al., "Estrogen receptor ligands and their responses in de novo and tamoxifen resistant cell models", Poster Presented at AACR, Apr. 16-20, 2016; New Orleans, LA.
Hamilton et al., "A Phase 1 Study of AZD9496, a Novel Oral, Selective Estrogen Receptor Degrader (SERD) in Women with Estrogen Receptor Positive, HER-2 Negative Advanced Breast Cancer (ABC)", Poster Presented at San Antonio Breast Cancer Symposium, Dec. 6-10, 2016.
Hemachandra et al., Hops (*Humulus lupulus*) Inhibits Oxidative Estrogen Metabolism and Estrogen-Induced Malignant Transformation in Human Mammary Epithelial Cells (MCF-10A) Published OnlineFirst Oct. 13, 2011; DOI: 10.1158/1940-6207.CAPR-11-0348.
Hemachandra et al.. "SERMs Attenuate Estrogen-Induced Malignant Transformation of Human Mammary Epithelial Cells by Upregulating Detoxification of Oxidative Metabolites", Published OnlineFirst, Mar. 5, 2014; DOI: 10.1158/1940-6207.CAPR-13-0296.
International Search Report and Written Opinion for PCT/US18/12675 dated May 4, 2018.
Kastrati et al., "A Novel Aspirin Prodrug Inhibits NFkB Activity and Breast Cancer Stem Cell Properties" BMC Cancer, 2015, 15, 845.

Kastrati et al., "Estrogen-Induced Apoptosis of Breast Epithelial Cells Is Blocked by NO/cGMP and Mediated by Extranuclear Estrogen Receptors" Endocrinology. 2010, 151(12), 5602-16, doi: 10.1210/en.2010-0378. Epub Oct. 13, 2010.
Kastrati et al., "Raloxifene and Desmethylarzoxifene Block Estrogen-Induced Malignant Transformation of Human Breast Epithelial Cells" PLoS, 2011, 6(11), e27876.
Kim et al., "Click Synthesis of Estradiol-Cyclodextrin Conjugates as Cell Compartment Selective Estrogens" Bioorganic & Medicinal Chemistry, 2010, 18(2) 809-821.
Kubinyi (3D QSAR in Drug Design: Ligand-Protein Interactions and Molecular Similarity, vol. 2-3, Springer, 1998, 800 pages). p. 243-44.
Liu et al. "Analysis of Protein Covalent Modification by Xenobiotics Using a Covert Oxidatively Activated Tag: Raloxifene Proof-of-Principle Study" Chem. Res. Toxicol., 2005, 18: 1485-1496.
Liu et al. "Bioactivation of the Selective Estrogen Receptor Modulator Desmethylated Arzoxifene to Quinoids: 4'-Fluoro Substitution Prevents Quinoid Formation" Chem. Res. Toxicol. 2005, 18: 162-173.
Liu et al. "Bioactivation of the Selective Estrogen Receptor Modulator Acolbifene to Quinone Methides", Chem. Res. Toxicol., 2005, 18: 174-182.
Liu et al. "Chemical Modification Modulates Estrogenic Activity, Oxidative Reactivity, and Metabolic Stability in 4'F-DMA, a New Benzothiophene Selective Estrogen Receptor Modulator", Chem. Res. Toxicol., 2006, 19: 779-787.
Liu et al. "Uterine Peroxidase-Catalyzed Formation of Diquinone Methides from the Selective Estrogen Receptor Modulators Raloxifene and Desmethylated Arzoxifene", Chem. Res. Toxicol., 2007, 20: 1676-1684.
Molloy et al. "Novel Selective Estrogen Mimics for the Treatment of Tamoxifen-Resistant Breast Cancer", Molecular Cancer Therapeutics, 2014, 13(11), 2515-2526; Published OnlineFirst Sep. 9, 2014: DOI: 10.1158/1535-7163.MCT-14-0319.
McInnes, C., "Progress in the evaluation of CDK inhibitors as anti-tumor agents" Drug Discov Today, 2008, 13(19-20): 875-881.
Michalsen et al., "Selective Estrogen Receptor Modulator (SERM) Lasofoxifene Forms Reactive Quinones Similar to Estradiol", Chem. Res. Toxicol., 2012, 25, 1472-1483.
Overk et al., " Structure-Activity Relationships for a Family of Benzothiophene Selective Estrogen Receptor Modulators Including Raloxifene and Arzoxifene", Chem. Med. Chem., 2007, 2: 1520-1526.
Park et al., "Toxicogenetics in drug development", Toxicology Letters, 2001, 120(1-3), 281-291.
Patel et al., "A Chimeric SERM-Histone Deacetylase Inhibitor Approach to Breast Cancer Therapy", Chem. Med. Chem., 2014, 9, 602-613.
Peng et al., "Selective Estrogen Receptor Modulator Delivery of Quinone Warheads to DNA Triggering Apoptosis in Breast Cancer Cells", ACS Chemical Biology, 2009 4(12), 1039-1049.
Peng et al., "Unexpected Hormonal Activity of a Catechol Equine Estrogen Metabolite Reveals Reversible Glutathione Conjugation", Chem. Res. Toxicol., 2010, 23: 1374-1383.
Presser, Armin and Antje Hüfner "Trimethylsilyldiazomethane—A Mild and Efficient Reagent for the Methylation of Carboxylic Acids and Alcohols in Natural Products" Monatshefte für Chemie, 2004, 13 5(8), 1015-1022.
Pubchem: Substance Record for SID 236885489. 13.02.2015. [retrieved on Mar. 24, 2017], Retrieved from the Internet. <URL: https://pubchem.ncbi.nlm.nih.gov/substance/236885489>.
Qin et al., "Benzothiophene Selective Estrogen Receptor Modulators with Modulated Oxidative Activity and Receptor Affinity", J. Med. Chem., 2007, 50: 2682-2692.
Qin et al., "Structural Modulation of Oxidative Metabolism in Design of Improved Benzothiophene Selective Estrogen Receptor Modulators", Drug Metabolism and Disposition, 2009, 3 7(1), 161-169.
Romagnoli et al., "Synthesis and Biological Evaluation of 2- and 3-Aminobenzo[b]thiophene Derivatives as Antimitotic Agents and Inhibitors of Tubulin Polymerization", J. Med. Chem., 2007, 50(9), 2273-2277.

(56) References Cited

OTHER PUBLICATIONS

Romagnoli et al., "Synthesis and biological evaluation of 2-(3', 4', 5"-trimethoxybenzoyl)-3-aryl/aiylaminobenzo[b]thiophene derivatives as novel class of antiproliferative agents", Eur J Med Chem., 2010, 45(12), 5781-5791.
Schönauer, K. and E. Zibral "Reactions with organophosphorus compounds, 50.: Trimethylsilylethoxymethylene triphenylphosphorane, a novel reagent for the homologation of carbonyl compounds", Tetrahedron Letters, 1983, 24(6), 573-576.
Shimamura, T. et al., "Identification of potent 5-pyrimidinyl-2-aminothiazole CDK4, 6 inhibitors with significant selectivity over CDK1, 2, 5, 7, and 9", Bioorg Med Chem Lett., 2006, 16(14): 3751-3754.
Sielecki et al., "Quinazolines as cyclin dependent kinase inhibitors", BMCL, 2001, 11(9), 1157-1160.
Soni, R. et al., "Selective in vivo and in vitro effects of a small molecule inhibitor of cyclin-dependent kinase 4", J Natl Cancer Inst., 2001, 93(6), 436-446.
Thatcher et al., "Endocrine-independent ER+ breast cancer therapy: Benzothiophene SERMs, SERDs, MERDs, SEMs, and ShERPAs" PowerPoint presented at 252nd ACS National Meeting, Aug. 21, 2016.
Toader et al., "Nitrosation, Nitration, and Autoxidation of the Selective Estrogen Receptor Modulator Raloxifene by Nitric Oxide, Peroxynitrite, and Reactive Nitrogen/Oxygen Species", Chem. Res. Toxicol., 2003, 16(10), 1264-1276.
Toogood, P. L. et al. "Discovery of a potent and selective inhibitor of cyclin-dependent kinase 4/6", J Med Chem, 2005, 48(7), 2388-2406.
Tria et al., "Discovery of LSZ102, a potent orally bioavailable selective estrogen receptor degrader (SERD) for the treatment of estrogen receptor positive breast cancer", Journal of Medicinal Chemistry, 2018, 61, 2837-2864.
Vandevrede et al., "A NO Donor Approach to Neuroprotective and Procognitive Estrogen Therapy Overcomes Loss of NO Synthase Function and Potentially Thrombotic Risk", PLoS One. 2013; 8(8): e70740. Published online Aug. 16, 2013. doi: 10.1371/journal.pone. 0070740.
Wang et al., "Development of a Liquid Chromatography Electrospray Ionization Tandem Mass Spectrometry Method for Analysis of Stable 4-Hydroxyequilenin-DNA Adducts in Human Breast Cancer Cells", Chem. Res. Toxicol., 2009, 22: 1129-1136.
Wang et al., "Estrogen Receptor a Enhances the Rate of Oxidative DNA Damage by Targeting an Equine Estrogen Catechol Metabolite to the Nucleus", The Journal of Biological Chemistry, 2009, 284(13), 8633-8642.
Wang et al., "Redox Cycling of Catechol Estrogens Generating Apurinic/Apyrimidinic Sites and 8-oxo-Deoxyguanosine via Reactive Oxygen Species Differentiates Equine and Human Estrogens", Chem. Res. Toxicol., 2010, 23: 1365-1373.
Wermuth, "The Practice of Medicinal Chemistry", 2nd Ed., Academic Press, 2003, 768 pages, Chaps. 9-10; Published Jun. 11, 2003.
White, J.D. et al., "Transformations of Quinic Acid. Asymmetric Synthesis and Absolute Configuration of Mycosporin I and Mycosporingly", Journal of Organic Chemistry, 1995, 60(12), 3600-3611.
Xiong et al., "Novel Selective Estrogen Receptor Downregulators (SERDs) Developed against Treatment-Resistant Breast Cancer", J. Med. Chem., 2017, 60: 1325-1342.
Xiong et al., "Selective Human Estrogen Receptor Partial Agonists (ShERPAs) for Tamoxifen-Resistant Breast Cancer", J. Med. Chem., 2016, 59: 219-237.
Yu et al., "Comparative Methods for Analysis of Protein Covalent Modification by Electrophilic Quinoids Formed from Xenobiotics", Bioconjugate Chem., 2009, 20: 728-741.

Yu et al., "Structural Modulation of Reactivity/Activity in Design of Improved Benzothiophene Selective Estrogen Receptor Modulators: Induction of Chemopreventive Mechanisms", Mol. Cancer, Ther. 2007, 6(9), 2418-2428; DOI: 10.1158/1535-7163.MCT-07-0268.
U.S. Appl. No. 17/153,516, Tavares et al., filed Jan. 20, 2021.
U.S. Appl. No. 17/222,873, Strum et al., filed Apr. 5, 2021.
U.S. Appl. No. 17/234,686, Strum et al., filed Apr. 19, 2021.
U.S. Appl. No. 17/236,687, Schneider et. al., filed May 7, 2021.
U.S. Appl. No. 17/315,011, Sorrentino et al., filed May 7, 2021.
U.S. Appl. No. 16/886,309, Strum, et al., filed May 28, 2020.
U.S. Appl. No. 16/924,033, Beelen et al., filed Jul. 8, 2020.
U.S. Appl. No. 16/926,035, Strum, et al., filed Jul. 10, 2020.
U.S. Appl. No. 17/067,549, Strum, et al., filed Oct. 9, 2020.
U.S. Appl. No. 17/074,550, Thatcher et al., filed Oct. 19, 2020.
Andreano Kaitlyn et al., "G1T38, an oral selective estrogen receptor degrader, and the CDK 4/6 inhibitor lerociclib inhibit tumor growth in animal models of endocrine-resistant breast cancer", Breast Cancer Research and Treatment, 2020, 180(3), 635-646, XP037077693.
European Search Report and Search Opinion for EP187361159 dated Jul. 24, 2020.
NCT02983071—Clinical trial, NCT02983071, "History of changes for study: NCT02983071-G1T38, a CDK 4/6 inhibitor in combination with Fulvestrant in hormone receptor-positive, HER2-negative locally advanced or metastatic breast cancer", Clinicaltrials. gov archive Dec. 7, 2016 pp. 1-5, XP055714462.
Wardell S. et al., "Abstract 5641: Effects of G1T48, a novel orally bioavailable selective estrogen receptor degrader (SERD), and the CDK 4/6 inhibitor, G1T38, on tumor growth in animal models of endocrine resistant breast cancer", Cancer Research, 2017, 77(13), 1-4, XP055714473.
Wardell S. E. et al., "Efficacy of SERD/SERM hybrid CDK 4/6 inhibitor combinations in models of endocrine therapy-resistant breast cancer", Clinical Cancer Research, 2015, 21(22), 5121-5130, XP055555127.
Beith, Jane, et al., Hormone receptor positive, HER2 negative metastatic breast cancer: a systematic review of the current treatment landscape, J. of Clin. Oncol., 2016, 12 (Suppl. 1), 3-18.
Redfern, Andrew, et al., Hormone receptor positive HER2 negative metastatic breast cancer: future treatment landscape Asia-Pacific J. of Clin. Oncol., Mar. 2016, 12 (Suppl. 1), 19-31.
Rugo, Hope S., et al. Endocrine Therapy for hormone receptor—positive metastatic breast cancer: American Society of Clinical Oncology Guideline, J. of Clin. Oncol., Sep. 1, 2016, 34 (25), 3069-3103.
Weir, Hazel M., et al., "AZD9496: An Oral Estrogen Receptor Inhibitor That Blocks the Growth of ER-Positive and ESRI-Mutant Breast Tumors in Preclinical Models," Therapeutics, Targets, and Chemical Biology, Cancer Res; 76(11)3307-18, Jun. 1, 2016.
Xiong, et al. "Novel Selective Estrogen Receptor Downregulators Developed Using Endocrine-Independent Breast Cancer Cell Lines", Department of Medicinal Chemistry & Pharmacognosy, Department of Biopharmaceutical Science, IL Chicago, Poster Presented at AACR, Apr. 14, 2016, 1 page.
Xiong, et al. "Novel Selective Estrogen Receptor Downregulators Developed Using Endocrine-Independent Breast Cancer Cell Lines", Department of Medicinal Chemistry & Pharmacognosy, Department of Biopharmaceutical Science, IL Chicago, Poster Presented at AACR, Mar. 25, 2016, 1 page.
Xiong et al., "Novel Selective Estrogen Receptor Downregulators (SERDs) for Advanced Breast Cancer", Department of Medicinal Chemistry & Pharmacognosy, Department of Biopharmaceutical Science, IL Chicago, Poster Presented at UIC Cancer Center, Oct. 15, 2015., 1 page.
Xiong, et al., "Novel Selective Estrogen Receptor Downregulators (SERDs) for Advanced Breast Cancer", Department of Medicinal Chemistry & Pharmacognosy, Department of Biopharmaceutical Science, IL Chicago, Poster Presented at UIC Research Day, Feb. 25, 2016, 1 page.
U.S. Appl. No. 17/554,940, Roberts et al., filed Dec. 17, 2021.
U.S. Appl. No. 17/403,577, Strum et al., filed Aug. 16, 2021.
U.S. Appl. No. 17/234,686, Strum, filed Apr. 19, 2021.

COMBINATION THERAPY FOR TREATMENT OF CANCER

CROSS REFERENCE TO RELATED APPLICATIONS

This application is a continuation of International Patent Application No. PCT/US2018/012675, filed Jan. 5, 2018, which claims the benefit of U.S. Provisional Application 62/443,588 filed on Jan. 6, 2017. These applications are hereby incorporated by reference for all purposes.

FEDERAL FUNDING

This invention was made in part with government support under contract no. 1R01CA188017-01A1 awarded by the National Institutes of Health. The government has certain rights in this invention.

JOINT RESEARCH AGREEMENT

The present invention was made by or on behalf of the below listed parties to a joint research agreement. The joint research agreement was in effect on or before the date of the filing of this application and the claimed invention was made as a result of activities undertaken within the scope of the joint research agreement. The parties to the joint research agreement are G1 Therapeutics, Inc. and The Board of Trustees of The University of Illinois.

BACKGROUND OF THE INVENTION

In 2017, the Susan G. Komen Foundation estimated that there were almost 250,000 new cases of invasive breast cancer diagnosed in the United States alone, and over 40,000 women died of the disease. Approximately 70% of breast cancer patients have estrogen receptor positive (ER+) tumors. The selective estrogen receptor modulator (SERM), tamoxifen, and aromatase inhibitors (AIs) represent first-line treatment for ER+ patients; however, almost 50% of patients either do not respond or acquire resistance within five years of treatment. Multiple mechanisms contribute to the development of an ER+ treatment resistant (TR) phenotype, in which growth is endocrine independent, including ligand-independent constitutive activation of ER. These cancers are difficult to treat and can lead to less favorable outcomes.

Genentech disclosed a series of tetrahydro-pyrido[3,4-b]indol-1-yl compounds with estrogen receptor modulation activity in US2016/0175289 and a combination therapy of three compounds, one of which was GDC-0810, for estrogen receptor modulation in US2015/0258080.

AstraZeneca is currently developing AZD9496, a novel, oral selective estrogen receptor downregulator in patients with estrogen receptor positive breast cancer (WO 2014/191726).

Additional anti-estrogenic compounds are disclosed in WO 2012/084711; WO 2002/013802; WO 2002/004418; WO 2002/003992; WO 2002/003991; WO 2002/003990; WO 2002/003989; WO 2002/003988; WO 2002/003986; WO 2002/003977; WO 2002/003976; WO 2002/003975; WO 2006/078834; U.S. Pat. No. 6,821,989; US 2002/0128276; U.S. Pat. No. 6,777,424; US 2002/0016340; U.S. Pat. Nos. 6,326,392; 6,756,401; US 2002/0013327; U.S. Pat. Nos. 6,512,002; 6,632,834; US 2001/0056099; U.S. Pat. Nos. 6,583,170; 6,479,535; WO 1999/024027; U.S. Pat. No. 6,005,102; EP 0802184; U.S. Pat. Nos. 5,998,402; 5,780,497 and 5,880,137.

J-Pharma is currently developing benzothiophene compounds for the treatment of disorders related to urate transportation. See for example WO 2012/048058.

Bionomics LTD is developing benzofurans, benzothiophenes, benzoselenophenes, and indoles for treatment of tubulin polymerization related disorders. See for example WO 2007/087684.

Additional benzothiophene compounds are disclosed in WO 2010/127452, WO 2010/093578, WO 2009/013195, EP1947085, JP 2005-129430, US 2007/0112009, WO 2005/016929, EP0752421, EP0622673, EP0551849, EP0545478, U.S. Pat. No. 5,491,123, and WO 2006/084338.

U.S. Patent Applications and PCT Applications assigned to University of Illinois that describe benzothiophene based-compounds for estrogen receptor modulation include US 2017-0166550, US 2017-0166551, WO 2017/100712, and WO 2017/100715.

Despite the progress made in the medical treatment of hormone-sensitive and resistant tumors and cancers, a need still remains to provide new therapies and methods for the treatment of these serious diseases.

SUMMARY OF THE INVENTION

This invention provides advantageous new combinations, compositions and methods to treat a cancer or tumor in a host, typically a human, that includes administering to the host a compound selected from Formula A, B or C (a selective estrogen receptor downregulator, SERD) or a pharmaceutically acceptable salt thereof in combination with a compound selected from Formula D (a CDK 4/6 inhibitor), or a pharmaceutically acceptable salt thereof. In one embodiment, the cancer or tumor is or has been hormone sensitive, and may be or have been, for example, estrogen or androgen sensitive.

By "combination" is meant that the selected compounds as described herein are administered in a single dosage form, or in two or more separate dosage forms given either simultaneously or consecutively, as long as they are provided in a manner that they can act in a concerted fashion to achieve the desired results. In one embodiment, a pharmaceutical composition is provided that includes at least the selected SERD and the selected CDK 4/6 inhibitor, either of which can be in the form of a pharmaceutically acceptable salt, optionally in a pharmaceutically acceptable carrier.

Formula A is a compound selected from:

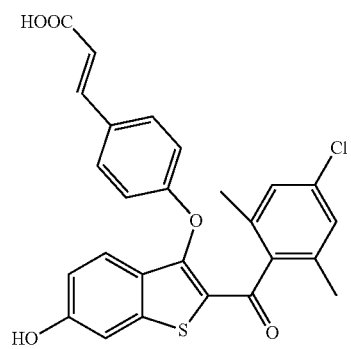

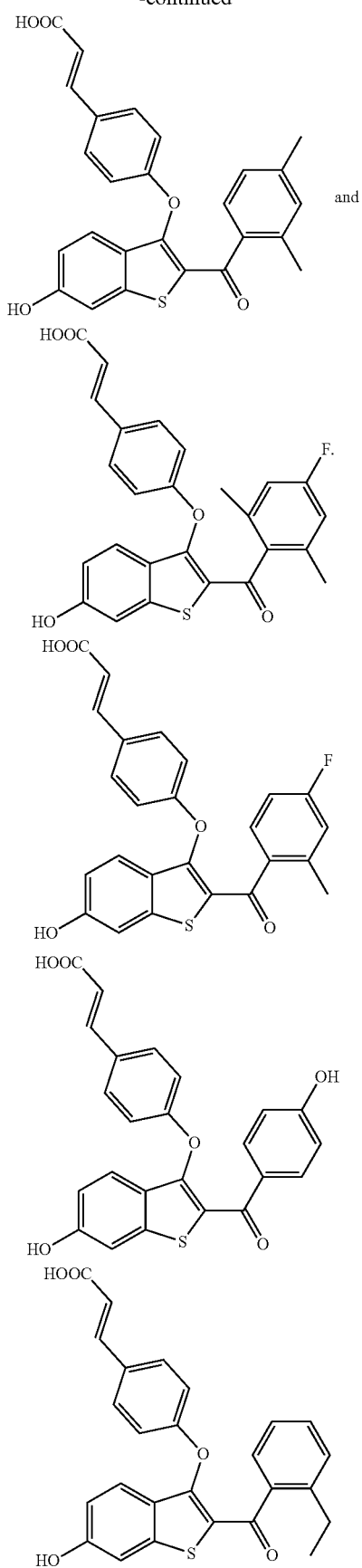
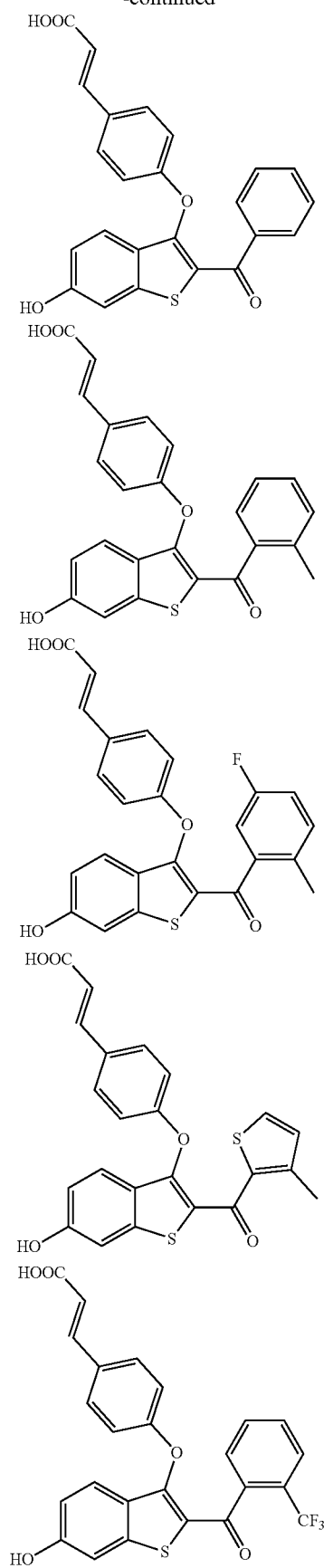
and

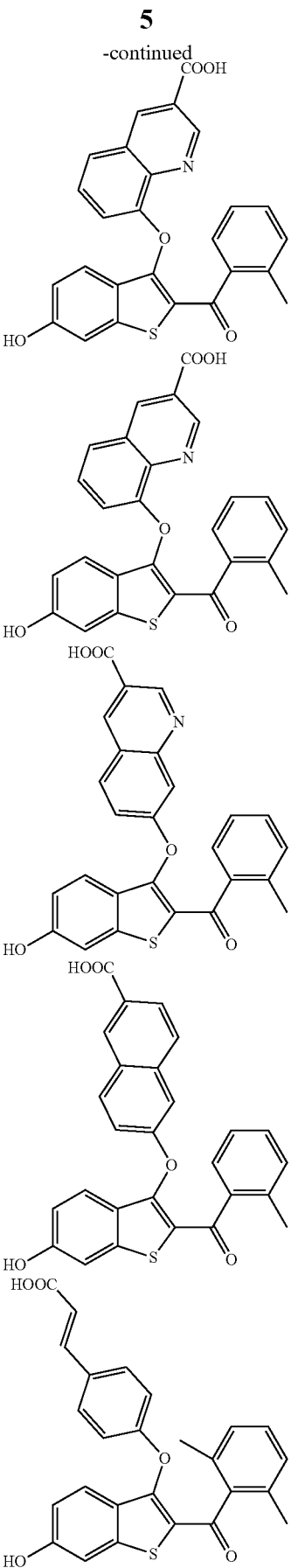
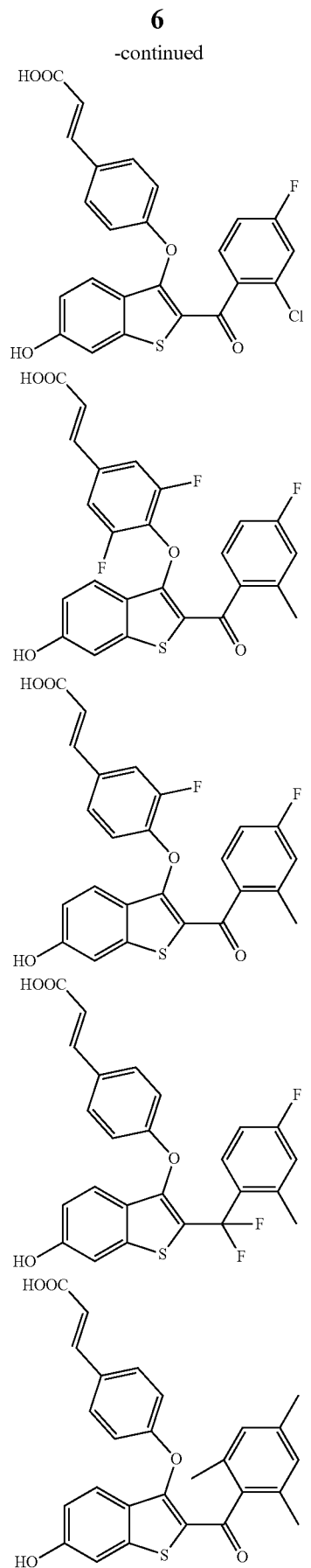

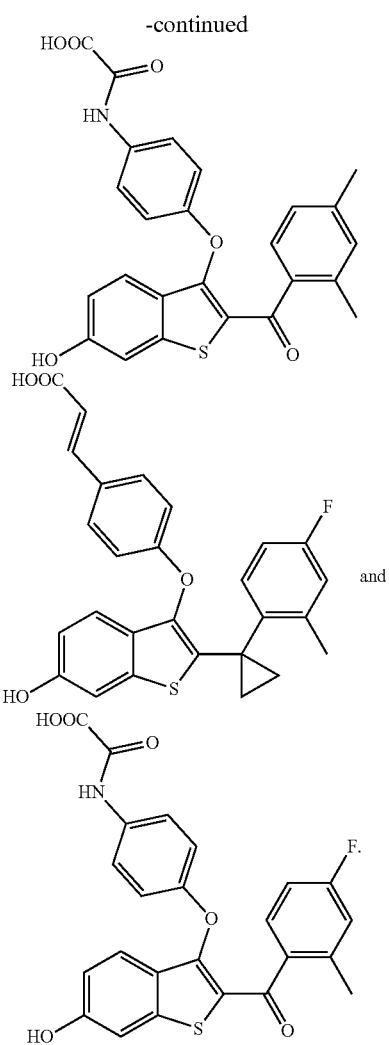

Formula B is a compound selected from:
Formula C is:

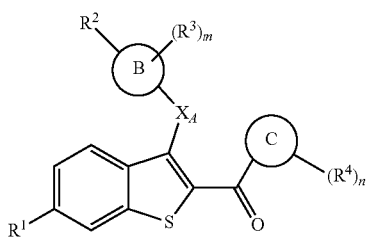

Formula C wherein:
m is 0, 1, 2, 3, or 4;
n is 0, 1, 2, 3, or 4;
$X_A$ is selected from —O—, —CH$_2$—, —S—, —NH—, —NMe-, —CF$_2$—, and C$_3$cycloalkyl;
Ring B is phenyl, naphthyl, quinolinyl, 5- or 6-membered monocyclic heteroaryl or 7-, 8-, 9- or 10 membered bicyclic heterocyclyl;
Ring C is phenyl, thiophenyl (i.e., thienyl), 5- or 6-membered monocyclic heteroaryl or 7-, 8-, 9- or 10-membered bicyclic heterocyclyl;

$R^1$ is selected from hydroxyl, hydrogen, halogen, —O(C$_1$-C$_6$ alkyl), —OC(O)(C$_1$-C$_6$ alkyl), —OC(O)C$_6$H$_5$, —OC(O)O(C$_1$-C$_6$ alkyl), —OC(O)OC$_6$H$_5$ and —OSO$_2$(C$_2$-C$_6$ alkyl);
$R^2$ is selected from —CH═CHCOOH, —NH(CO)COOH, —COOH, —C$_2$-C$_6$alkenylene-COOH and —C$_2$-C$_6$alkynylene-COOH;
$R^3$ is independently selected at each occurrence from hydrogen, halogen, —CN, —NO$_2$, —C$_1$-C$_6$alkyl and —C$_1$-C$_6$fluoroalkyl; and
$R^4$ is independently selected at each occurrence from hydrogen, halogen, hydroxyl, —C$_1$-C$_6$alkyl, —C$_1$-C$_6$fluoroalkyl, —CN, —O(C$_1$-C$_6$alkyl), and —O(C$_1$-C$_6$fluoroalkyl).

These compounds are disclosed in, for example, US 2017-0166550, US 2017-0166551, WO 2017/100712, and WO 2017/100715.

Formula D is a compound selected from:

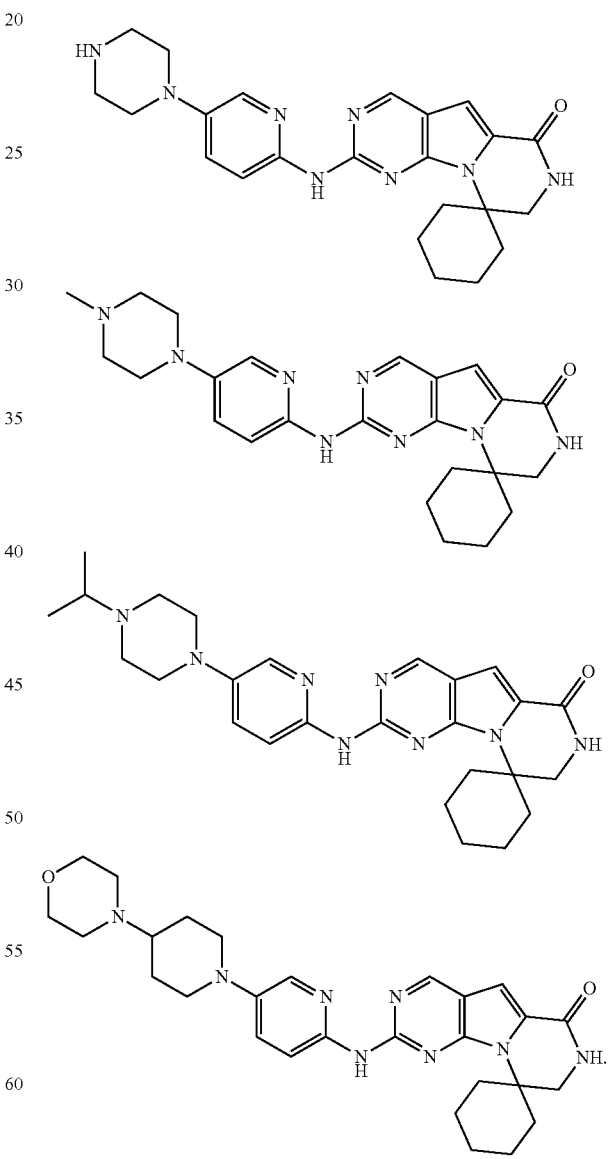

These compounds are described in U.S. Pat. Nos. 8,598,186, 8,598,197, 9,481,691, and PCT Patent Application WO2010/075542.

A particularly advantageous combination is the method of use as described herein or composition that includes:

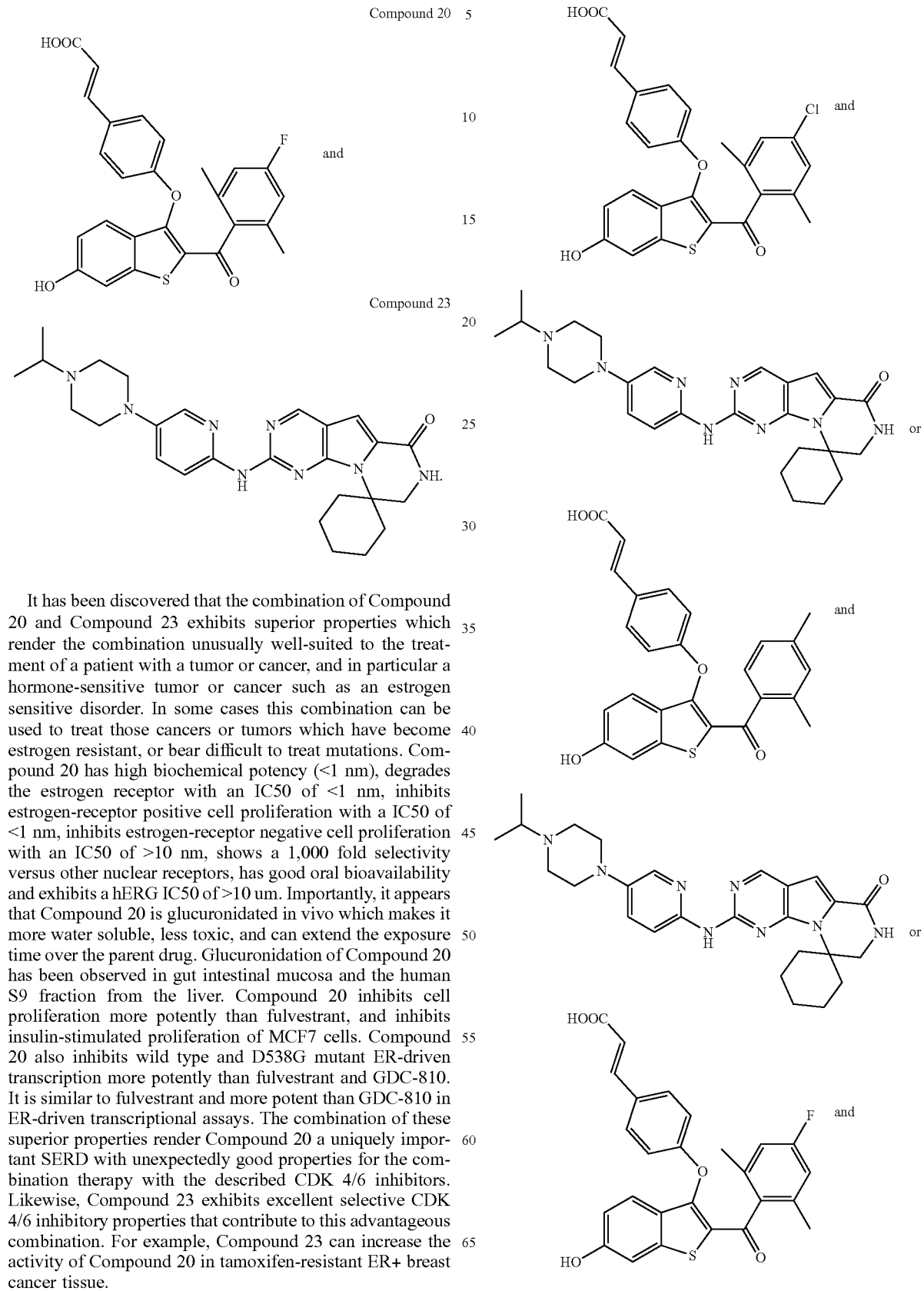

Compound 20 and

Compound 23

It has been discovered that the combination of Compound 20 and Compound 23 exhibits superior properties which render the combination unusually well-suited to the treatment of a patient with a tumor or cancer, and in particular a hormone-sensitive tumor or cancer such as an estrogen sensitive disorder. In some cases this combination can be used to treat those cancers or tumors which have become estrogen resistant, or bear difficult to treat mutations. Compound 20 has high biochemical potency (<1 nm), degrades the estrogen receptor with an IC50 of <1 nm, inhibits estrogen-receptor positive cell proliferation with a IC50 of <1 nm, inhibits estrogen-receptor negative cell proliferation with an IC50 of >10 nm, shows a 1,000 fold selectivity versus other nuclear receptors, has good oral bioavailability and exhibits a hERG IC50 of >10 um. Importantly, it appears that Compound 20 is glucuronidated in vivo which makes it more water soluble, less toxic, and can extend the exposure time over the parent drug. Glucuronidation of Compound 20 has been observed in gut intestinal mucosa and the human S9 fraction from the liver. Compound 20 inhibits cell proliferation more potently than fulvestrant, and inhibits insulin-stimulated proliferation of MCF7 cells. Compound 20 also inhibits wild type and D538G mutant ER-driven transcription more potently than fulvestrant and GDC-810. It is similar to fulvestrant and more potent than GDC-810 in ER-driven transcriptional assays. The combination of these superior properties render Compound 20 a uniquely important SERD with unexpectedly good properties for the combination therapy with the described CDK 4/6 inhibitors. Likewise, Compound 23 exhibits excellent selective CDK 4/6 inhibitory properties that contribute to this advantageous combination. For example, Compound 23 can increase the activity of Compound 20 in tamoxifen-resistant ER+ breast cancer tissue.

Other methods and compositions described herein include the combination of:

-continued
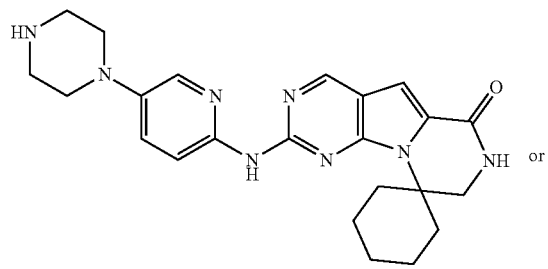
5
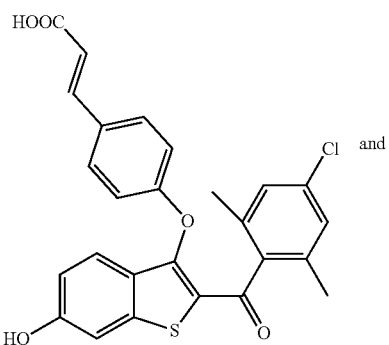 and
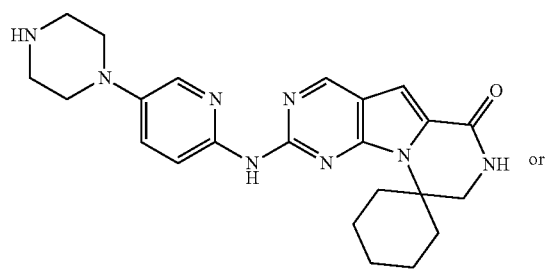 or
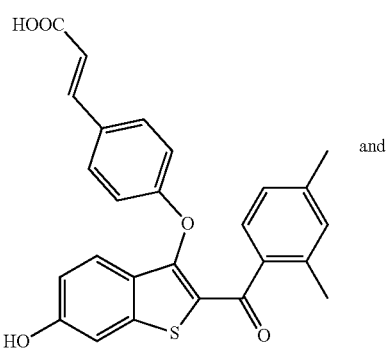 and
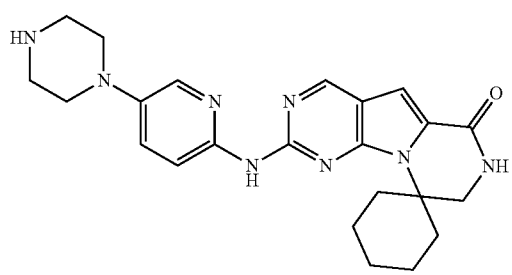
or a pharmaceutically acceptable salt of one or both of the compounds, optionally in one or more pharmaceutically acceptable carriers.
Other aspects of the invention as provided herein are methods of use as described herein or composition that include a combination of:
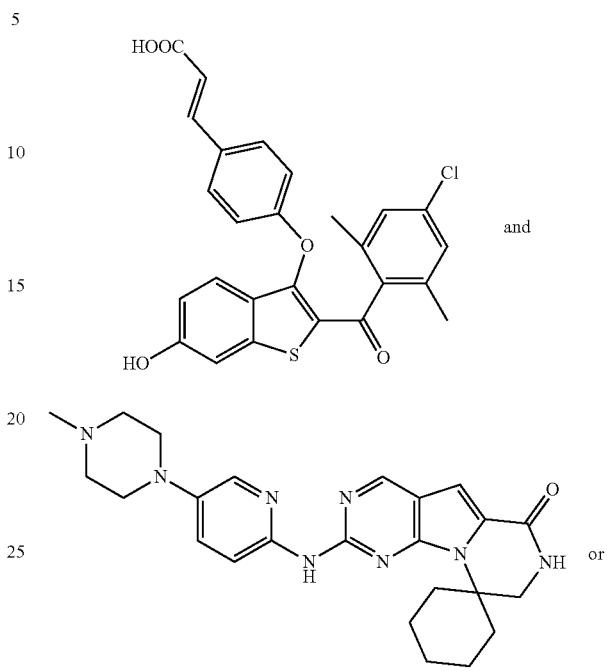
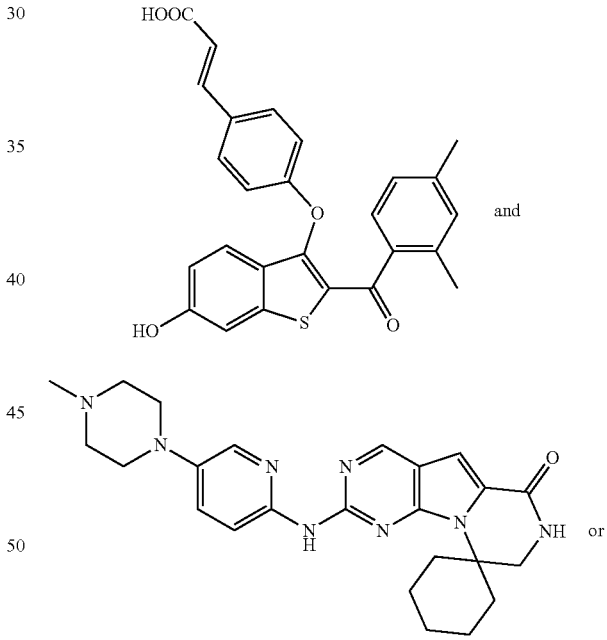
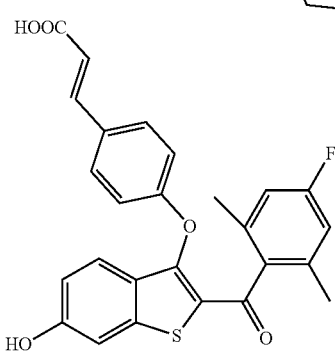 and -continued

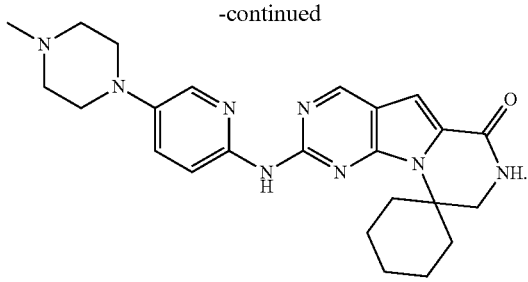

The present invention thus includes at least the following features:

(a) a method of treating a hormone sensitive tumor or cancer, such as an estrogen sensitive tumor or cancer as described herein, comprising administering to a subject in need thereof a therapeutically effective amount of at least one SERD compound selected from Formula A, Formula B and Formula C, or its pharmaceutically acceptable salt and at least one CDK 4/6 inhibiting compound of Formula D or its pharmaceutically acceptable salt, optionally in a pharmaceutically acceptable carrier;

(b) a method of treating a kidney, prostate, or lung cancer as described herein, comprising administering to a subject in need thereof a therapeutically effective amount of the combination of at least one SERD compound selected from Formula A, Formula B and Formula C, or its pharmaceutically acceptable salt and at least one CDK 4/6 inhibiting compound of Formula D or its pharmaceutically acceptable salt, optionally in one or more pharmaceutically acceptable carriers;

(c) a method of treating breast, ovarian, or endometrial cancer as described herein, comprising administering to a subject in need thereof a therapeutically effective amount of a combination of at least one SERD compound selected from Formula A, Formula B and Formula C, or its pharmaceutically acceptable salt and at least one CDK 4/6 inhibiting compound of Formula D or its pharmaceutically acceptable salt, optionally in one or more pharmaceutically acceptable carriers;

(d) a method of treating hormone receptor positive metastatic breast cancer as described herein, comprising administering to a subject in need thereof a therapeutically effective amount of a combination of at least one SERD compound selected from Formula A, Formula B and Formula C, or its pharmaceutically acceptable salt and at least one CDK 4/6 inhibiting compound of Formula D or its pharmaceutically acceptable salt, optionally in one or more pharmaceutically acceptable carriers;

(e) a method of treating tamoxifen resistant breast cancer as described herein, comprising administering to a subject in need thereof a therapeutically effective amount of a combination of compound of Formula A, Formula B, or Formula C, or a pharmaceutically acceptable salt thereof and a compound of Formula D or a pharmaceutically acceptable salt thereof, optionally in one or more pharmaceutically acceptable carriers;

(f) a method of treating triple negative breast cancer as described herein, comprising administering to a subject in need thereof a therapeutically effective amount of a combination of at least one SERD compound selected from Formula A, Formula B and Formula C, or its pharmaceutically acceptable salt and at least one CDK 4/6 inhibiting compound of Formula D or its pharmaceutically acceptable salt, optionally in one or more pharmaceutically acceptable carriers;

(g) a pharmaceutically acceptable combination or composition as described herein, comprising a compound of Formula A, Formula B, or Formula C, or its pharmaceutically acceptable salt, and a compound of Formula D, or its pharmaceutically acceptable salt, optionally in one or more pharmaceutically acceptable carriers;

(h) a pharmaceutically acceptable combination or composition as described herein, comprising a compound of Formula A, Formula B, or Formula C, or its pharmaceutically acceptable salt, and a compound of Formula D or its pharmaceutically acceptable salt, that is useful in the treatment or prevention of an estrogen-related disorder, including without limitation a tumor or cancer;

(i) use of a pharmaceutically acceptable combination or composition as described herein, in the manufacture of a medicament(s) for the treatment or prevention of an estrogen-related disorder, including but not limited to a tumor or cancer;

(j) a method for manufacturing a medicament for the therapeutic use to treat or prevent a disorder of abnormal cellular proliferation including but not limited to a tumor or cancer, characterized in that a pharmaceutically acceptable composition or combination as described herein, is used in the manufacture of the medicament(s);

(k) a pharmaceutically acceptable combination or composition as described herein, comprising a compound of Formula A, Formula B, or Formula C, or its pharmaceutically acceptable salt, and a compound of Formula D or its pharmaceutically acceptable salt, for use in the treatment or prevention of breast, kidney, uterine, ovarian or endometrial cancer;

(l) use of a pharmaceutically acceptable combination or composition as described herein, in the manufacture of a medicament for the treatment or prevention of breast, kidney, uterine, ovarian or endometrial cancer;

(m) a method for manufacturing a medicament(s) for the therapeutic use in treating or preventing breast, kidney, uterine, ovarian or endometrial cancer, characterized in that a pharmaceutically acceptable composition or combination as described herein, comprising a compound of Formula A, Formula B, or Formula C, or its pharmaceutically acceptable salt, and a compound of Formula D or its pharmaceutically acceptable salt, is used in the manufacture of the medicament(s);

(n) a pharmaceutically acceptable combination or composition as described herein, comprising a compound of Formula A, Formula B, or Formula C, or its pharmaceutically acceptable salt, and a compound of Formula D or its pharmaceutically acceptable salt, for use in the treatment or prevention of hormone receptor positive metastatic breast cancer;

(o) use of a pharmaceutically acceptable combination or composition as described herein, comprising a compound of Formula A, Formula B, or Formula C, or its pharmaceutically acceptable salt, and a compound of Formula D or its pharmaceutically acceptable salt, in the manufacture of a medicament for the treatment or prevention of a hormone receptor positive metastatic breast cancer tumor;

(p) a method for manufacturing a medicament for treatment or prevention of a hormone receptor positive metastatic breast cancer, characterized in that a pharmaceutically acceptable composition or combination as described herein, comprising a compound of Formula A, Formula B, or Formula C, or its pharmaceutically acceptable salt, and a compound of Formula D or its pharmaceutically acceptable salt, is used in the manufacture;

(q) a process for the preparation of a therapeutic product that contain an effective amount of a pharmaceutically acceptable composition or combination as described herein, comprising a compound of Formula A, Formula B, or Formula C, or its pharmaceutically acceptable salt, and a compound of Formula D, or its pharmaceutically acceptable salt.

Figure 13:
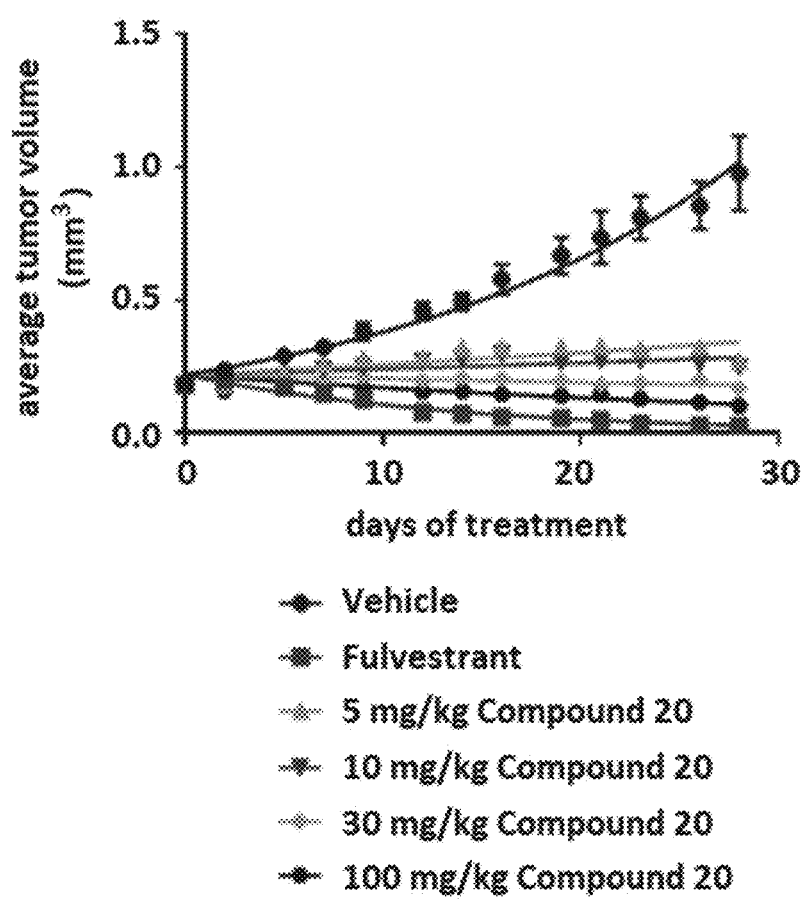

FIG. 13 is a graph measuring the inhibition of tumor volume in LTED xenograft tumors in OVX nu/nu (ovariectomy nude) mice following administration of doses ranging from 5 mg/kg to 100 mg/kg of Compound 20. As discussed in Example 17, Compound 20 was effective in decreasing tumor volume at all doses and the decrease in tumor volume correlated to the dose amount. The x-axis is treatment length measured in days and the y-axis is the average tumor volume measured in mm$^3$.

Figure 14A:
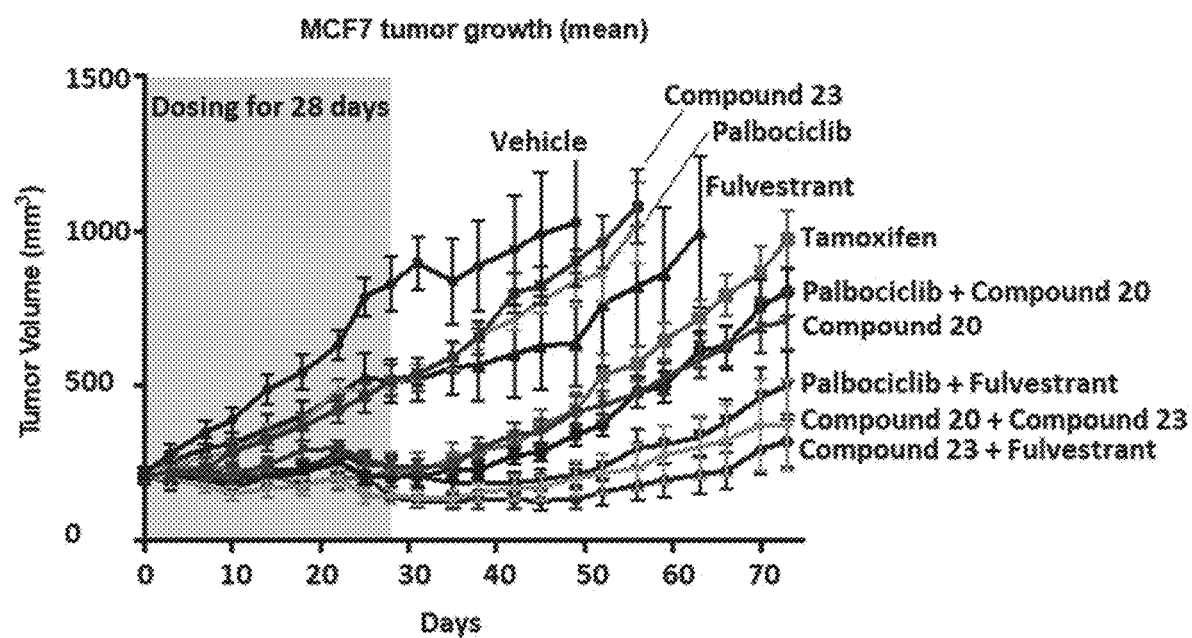

FIG. 14A is a graph measuring the inhibition of MCF7 ESR1$^{WT}$ tumor growth in vivo following administration of Compound 20, Compound 23, fulvestrant, palbociclib, and tamoxifen administered alone and in various combinations. The dosing amounts and schedules are discussed in Example 14. Mice were dosed for 28 days and tumor volume was measured past 70 days. As further discussed in Example 18, Compound 23 increased the efficacy of other compounds, including Compound 20 and fulvestrant. The x-axis is time measured in days and the y-axis is tumor volume measured in mm$^3$.

Figure 14B:
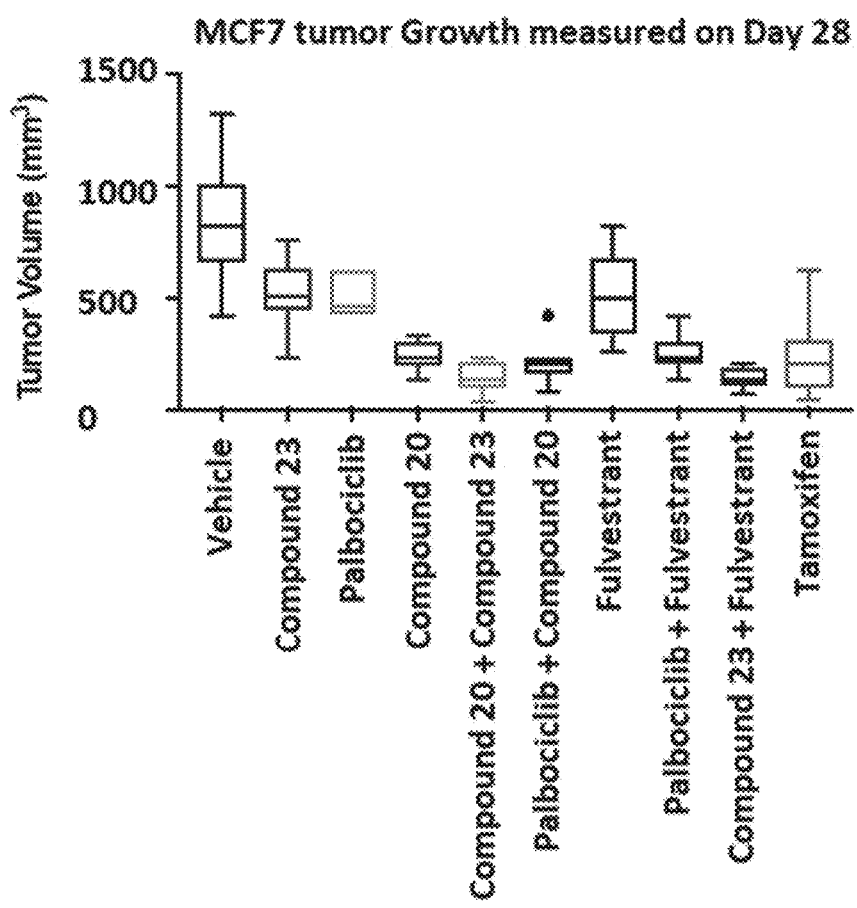

FIG. 14B is a graph measuring the inhibition of MCF7 ESR1$^{WT}$ tumor growth in vivo following administration of Compound 20, Compound 23, fulvestrant, palbociclib, and tamoxifen administered alone and in various combinations on day 28, the final day of dosing. Tumor volume was measured past 70 days. As further discussed in Example 18, Compound 23 increased the efficacy of other compounds, including Compound 20 and fulvestrant at the 28-day time point. The x-axis is time measured in days and the y-axis is tumor volume measured in mm$^3$.

Figure 15A:
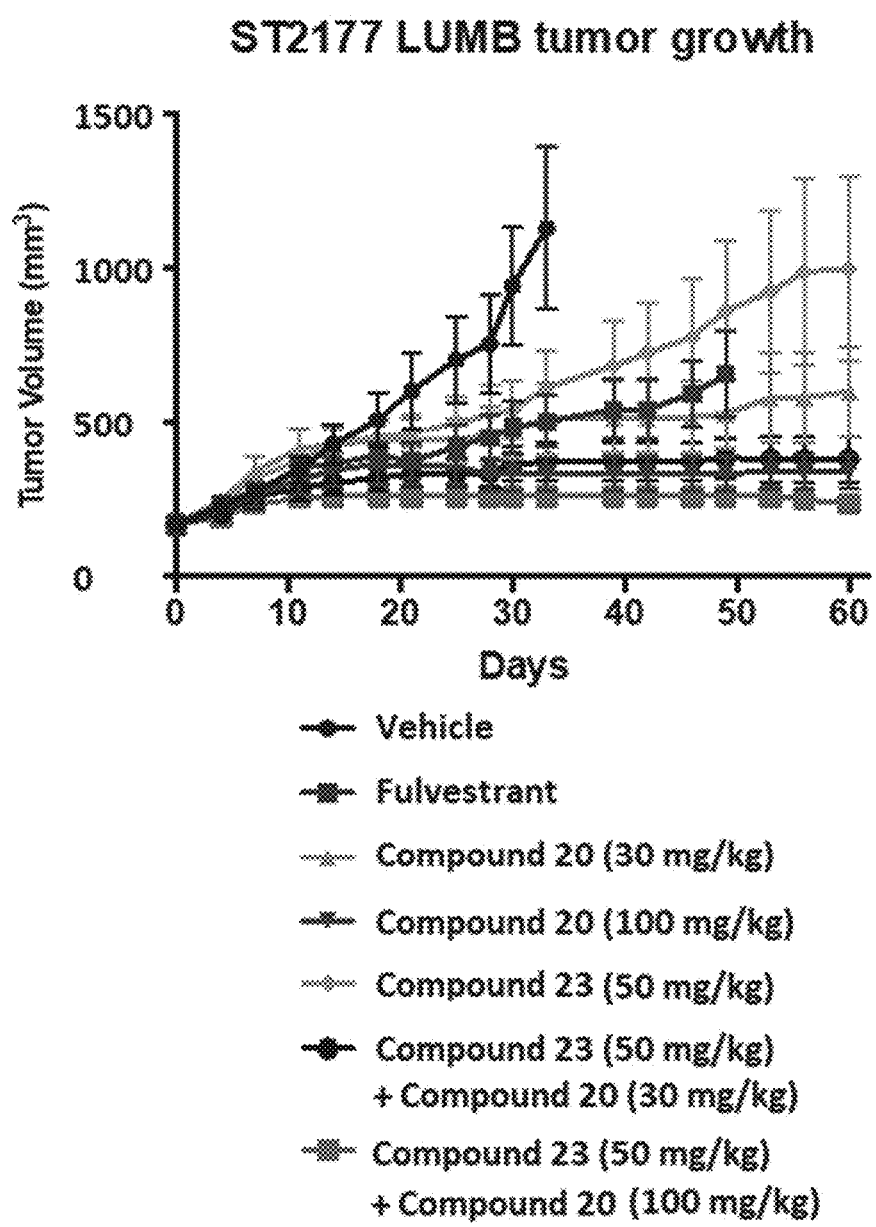

FIG. 15A is a graph measuring the inhibition of MCF7 ESR1$^{Y537S}$ tumor growth in vivo following oral administration of Compound 20 and Compound 23 administered alone and in combination compared to the subcutaneous administration of fulvestrant. The dosing amounts and schedules are discussed in Example 18. As further discussed in Example 14, Compound 23 (50 mg/kg) increased the efficacy Compound 20 when Compound 20 was administered at a dose of 30 mg/kg and 100 mg/kg. The x-axis is time measured in days and the y-axis is tumor volume measured in mm$^3$.

Figure 15B:
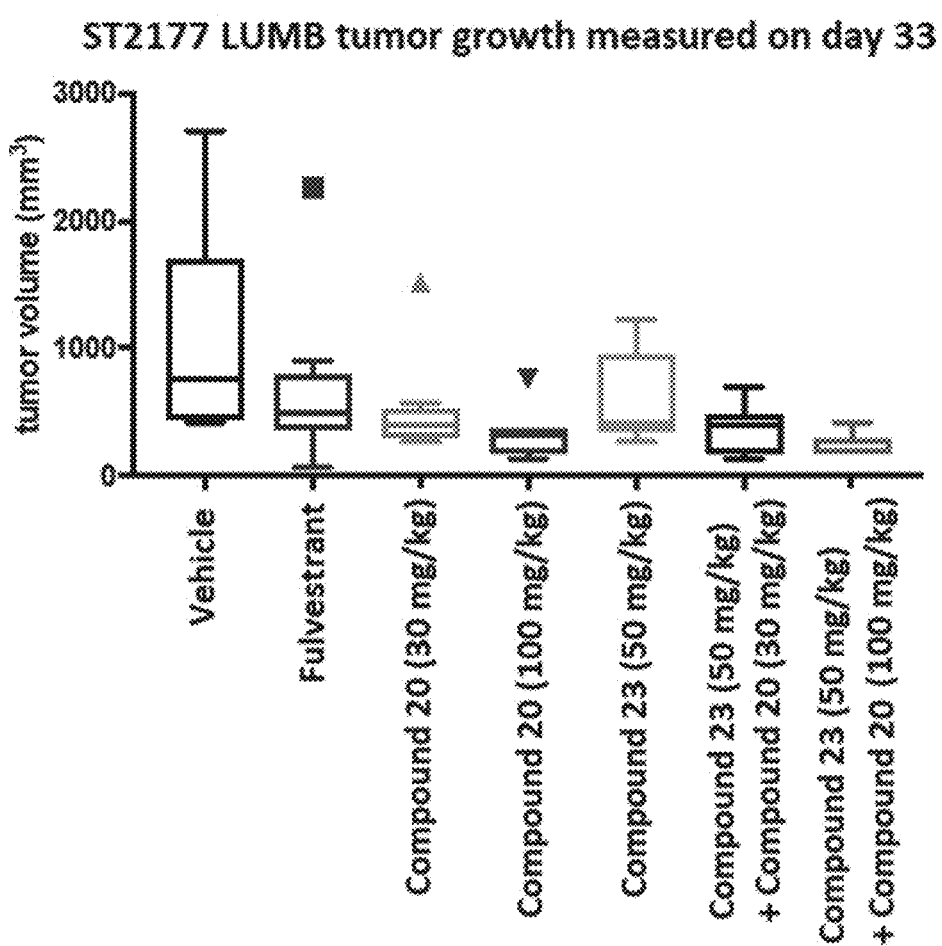

FIG. 15B is a graph measuring the inhibition of MCF7 ESR1$^{Y537S}$ tumor growth in vivo following oral administration of Compound 20 and Compound 23 administered alone and in combination compared to the subcutaneous administration of fulvestrant on day 33 of the study. The dosing amounts and schedules are discussed in Example 18. As further discussed in Example 14, the combination of Compound 23 (50 mg/kg) and Compound 20 (30 mg/kg or 100 mg/kg) was effective in decreasing tumor volume. The x-axis is time measured in days and the y-axis is tumor volume measured in mm$^3$.

DETAILED DESCRIPTION OF THE INVENTION

Definitions

The following terms and expressions used herein have the indicated meanings.

Terms used herein may be preceded and/or followed by a single dash, "-", or a double dash, "=", to indicate the bond order of the bond between the named substituent and its parent moiety; a single dash indicates a single bond and a double dash indicates a double bond. In the absence of a single or double dash it is understood that a single bond is formed between the substituent and its parent moiety; further, substituents are intended to be read "left to right" unless a dash indicates otherwise. For example, $C_1$-$C_6$alkoxycarbonyloxy and —OC(O)$C_1$-$C_6$ alkyl indicate the same functionality; similarly arylalkyl and -alkylaryl indicate the same functionality.

The terms "a" and "an" do not denote a limitation of quantity, but rather denote the presence of at least one of the referenced item. The term "or" means "and/or". Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of examples, or exemplary language (e.g., "such as"), is intended merely to better illustrate the invention and does not pose a limitation on the scope of the invention unless otherwise claimed. Unless defined otherwise, technical and scientific terms used herein have the same meaning as is commonly understood by one of skill in the art to which this invention belongs.

"Alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

"Alkyl" is a branched or straight chain saturated aliphatic hydrocarbon group. In several non-limiting embodiments, the alkyl group contains from 1 to about 12 carbon atoms, more generally from 1 to about 6 carbon atoms, from 1 to about 4 carbon atoms, or 1 to 3 carbon atoms. In one non-limiting embodiment, the alkyl contains from 1 to about 8 carbon atoms. In certain embodiments, the alkyl is $C_1$-$C_2$, $C_1$-$C_3$, $C_1$-$C_4$, $C_1$-$C_5$, or $C_1$-$C_6$. The specified ranges as used herein indicate an alkyl group having each member of the range described as an independent species. For example, the term $C_1$-$C_6$ alkyl as used herein indicates a straight or branched alkyl group having from 1, 2, 3, 4, 5, or 6 carbon atoms and is intended to mean that each of these is described as an independent species. For example, the term $C_1$-$C_4$ alkyl as used herein indicates a straight or branched alkyl group having from 1, 2, 3, or 4 carbon atoms and is intended to mean that each of these is described as an independent species. Examples of alkyl include, but are not limited to, methyl, ethyl, n-propyl, isopropyl, n-butyl, isobutyl, sec-butyl, t-butyl, n-pentyl, isopentyl, tert-pentyl, neopentyl, n-hexyl, 2-methylpentane, 3-methylpentane, 2,2-dimethylbutane, and 2,3-dimethylbutane. In an alternative embodiment, the alkyl group is optionally substituted. The term "Alkyl" also encompasses cycloalkyl or carbocyclic groups. For example, when a term is used that includes "alk" then "cycloalkyl" or "carbocyclic" can be considered part of the definition, unless unambiguously excluded by the context. For example and without limitation, the terms alkyl, alkoxy, haloalkyl, etc. can all be considered to include the cyclic forms of alkyl, unless unambiguously excluded by context.

"Alkenyl" is a linear or branched aliphatic hydrocarbon groups having one or more carbon-carbon double bonds that may occur at a stable point along the chain. In several non-limiting embodiments, the alkenyl group contains from 2 to about 12 carbon atoms, more generally from 2 to about 6 carbon atoms, from 2 to about 4 carbon atoms, or 2 to 3 carbon atoms. In one non-limiting embodiment, the alkenyl contains from 2 to about 8 carbon atoms. In certain embodiments, the alkenyl is $C_2$, $C_2$-$C_3$, $C_2$-$C_4$, $C_2$-$C_5$, or $C_2$-$C_6$. The specified ranges as used herein indicate an alkenyl group having each member of the range described as an independent species. For example, the term $C_2$-$C_6$ alkenyl as used herein indicates a straight or branched alkenyl group having 2, 2, 3, 4, 5, or 6 carbon atoms and is intended to mean that each of these is described as an independent species. For example, the term $C_2$-$C_4$ alkenyl as used herein indicates a straight or branched alkenyl group having from 2, 3, or 4 carbon atoms and is intended to mean that each of these is described as an independent species. Examples of alkenyl include, but are not limited to, ethylene, propylene, n-butylene, isobutylene, n-pentylene, and isopentylene. In an alternative embodiment, the alkenyl group is optionally substituted. The term "Alkenyl" also encompasses cycloalkenyl groups. For example, when a term is used that includes "alken" then "cycloalkenyl" can be considered part of the definition, unless unambiguously excluded by the context. For example and without limitation, the term alkenyl, can be considered to include the cyclic forms of alkenyl, unless unambiguously excluded by context. Examples of alkenyl radicals include, but are not limited to ethenyl, propenyl, allyl, propenyl, butenyl and 4-methylbutenyl. The term "alkenyl" also embodies "cis" and "trans" alkenyl geometry, or alternatively, "E" and "Z" alkenyl geometry. In an alternative embodiment, the alkenyl group is optionally substituted. The term "Alkenyl" also encompasses cycloalkyl or carbocyclic groups possessing at least one point of unsaturation.

"Alkynyl" is a branched or straight chain aliphatic hydrocarbon group having one or more carbon-carbon triple bonds that may occur at any stable point along the chain. In several non-limiting embodiments, the alkynyl group contains from 2 to about 12 carbon atoms, more generally from 2 to about 6 carbon atoms, from 2 to about 4 carbon atoms, or 2 to 3 carbon atoms. In one non-limiting embodiment, the alkynyl contains from 2 to about 8 carbon atoms. In certain embodiments, the alkynyl is $C_2$, $C_2$-$C_3$, $C_2$-$C_4$, $C_2$-$C_5$, or $C_2$-$C_6$. The specified ranges as used herein indicate an alkynyl group having each member of the range described as an independent species. For example, the term $C_2$-$C_6$ alkynyl as used herein indicates a straight or branched alkynyl group having 1, 2, 3, 4, 5, or 6 carbon atoms and is intended to mean that each of these is described as an independent species. For example, the term $C_2$-$C_4$ alkynyl as used herein indicates a straight or branched alkynyl group having from 2, 3, or 4 carbon atoms and is intended to mean that each of these is described as an independent species. In an alternative embodiment, the alkynyl group is optionally substituted. The specified ranges as used herein indicate an alkynyl group having each member of the range described as an independent species, as described above for the alkyl moiety. Examples of alkynyl include, but are not limited to, ethynyl, propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl and 5-hexynyl. In an alternative embodiment, the alkynyl group is optionally substituted. The term "Alkynyl" also encompasses cycloalkyl or carbocyclic groups possessing at least one point of unsaturation.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("$C_6$ aryl"; e.g., phenyl). In some embodiments, an aryl group has 10 ring carbon atoms ("$C_{10}$ aryl"; e.g., naphthyl such as 1-naphthyl and 2-naphthyl). In some embodiments, an aryl group has 14 ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. The one or more fused carbocyclyl or heterocyclyl groups can be 4 to 7 or 5 to 7-membered saturated or partially unsaturated carbocyclyl or heterocyclyl groups that optionally contain 1, 2 or 3 heteroatoms independently selected from nitrogen, oxygen, phosphorus, sulfur, silicon and boron, to form, for example, a 3,4-methylenedioxyphenyl group. In one non-limiting embodiment, aryl groups are pendant. An example of a pendant ring is a phenyl group substituted with a phenyl group. In an alternative embodiment, the aryl group is optionally substituted as described above. In certain embodiments, the aryl group is an unsubstituted $C_6$-14 aryl. In certain embodiments, the aryl group is a substituted $C_6$-14 aryl. An aryl group may be optionally substituted with one or more functional groups that include but are not limited to, halo, hydroxy, nitro, amino, cyano, haloalkyl, aryl, heteroaryl, and heterocyclo.

"Cyano" and "nitrile" mean a —CN group.

"Halo" or "halogen" means —Cl, —Br, —I or —F. In certain embodiments, "halo" or "halogen" refers to —Cl or —F.

"Haloalkyl" is a branched or straight-chain alkyl groups substituted with 1 or more halo atoms described above, up to the maximum allowable number of halogen atoms. In several non-limiting embodiments, the haloalkyl group contains from 1 to about 12 carbon atoms, more generally from 1 to about 6 carbon atoms, from 1 to about 4 carbon atoms, or 1 to 3 carbon atoms. In one non-limiting embodiment, the haloalkyl contains from 1 to about 8 carbon atoms. In certain embodiments, the haloalkyl is $C_1$-$C_2$, $C_2$-$C_3$, $C_2$-$C_4$, $C_2$-$C_5$, or $C_2$-$C_6$. The specified ranges as used herein indicate a haloalkyl group having each member of the range described as an independent species. For example, the term $C_1$-$C_6$ haloalkyl as used herein indicates a straight or branched haloalkyl group having 1, 2, 3, 4, 5, or 6 carbon atoms and is intended to mean that each of these is described as an independent species. For example, the term $C_1$-$C_4$ haloalkyl as used herein indicates a straight or branched alkynyl group having from 1, 2, 3, or 4 carbon atoms and is intended to mean that each of these is described as an independent species. In an alternative embodiment, the haloalkyl group is optionally substituted. Examples of haloalkyl groups include, but are not limited to, fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. "Perhaloalkyl" means an alkyl group having all hydrogen atoms replaced with halogen atoms. Examples include but are not limited to, trifluoromethyl and pentafluoroethyl.

The term "heteroaryl" denotes aryl ring systems that contain one or more heteroatoms selected from O, N and S, wherein the ring nitrogen and sulfur atom(s) are optionally oxidized, and nitrogen atom(s) are optionally quarternized.

Examples include but are not limited to, unsaturated 5 to 6 membered heteromonocyclyl groups containing 1 to 4 nitrogen atoms, such as pyrrolyl, imidazolyl, pyrazolyl, 2-pyridyl, 3-pyridyl, 4-pyridyl, pyrimidyl, pyrazinyl, pyridazinyl, triazolyl [e.g., 4H-1,2,4-triazolyl, IH-1,2,3-triazolyl, 2H-1,2,3-triazolyl]; unsaturated 5- to 6-membered heteromonocyclic groups containing an oxygen atom, for example, pyranyl, 2-furyl, 3-furyl, etc.; unsaturated 5 to 6-membered heteromonocyclic groups containing a sulfur atom, for example, 2-thienyl, 3-thienyl, etc.; unsaturated 5- to 6-membered heteromonocyclic groups containing 1 to 2 oxygen atoms and 1 to 3 nitrogen atoms, for example, oxazolyl, isoxazolyl, oxadiazolyl [e.g., 1,2,4-oxadiazolyl, 1,3,4-oxadiazolyl, 1,2,5-oxadiazolyl]; unsaturated 5 to 6-membered heteromonocyclic groups containing 1 to 2 sulfur atoms and 1 to 3 nitrogen atoms, for example, thiazolyl, thiadiazolyl [e.g., 1,2,4-thiadiazolyl, 1,3,4-thiadiazolyl, 1,2,5-thiadiazolyl].

The term "heterocyclyl" (or "heterocyclo") includes saturated, and partially saturated heteroatom-containing ring radicals, where the heteroatoms may be selected from nitrogen, sulfur and oxygen. Heterocyclic rings comprise monocyclic 6-8 membered rings, as well as 5-16 membered bicyclic ring systems (which can include bridged fused and spiro-fused bicyclic ring systems). It does not include rings containing —O—O—, —O—S— or —S—S— portions. Said "heterocyclyl" group may be optionally substituted with 1 to 3 substituents that include but are not limited to, hydroxyl, Boc, halo, haloalkyl, cyano, alkyl, aralkyl, oxo, alkoxy, and amino. Examples of saturated heterocyclo groups include saturated 3- to 6-membered heteromonocyclic groups containing 1 to 4 nitrogen atoms [e.g. pyrrolidinyl, imidazolidinyl, piperidinyl, pyrrolinyl, piperazinyl]; saturated 3 to 6-membered heteromonocyclic group containing 1 to 2 oxygen atoms and 1 to 3 nitrogen atoms [e.g. morpholinyl]; saturated 3 to 6-membered heteromonocyclic group containing 1 to 2 sulfur atoms and 1 to 3 nitrogen atoms [e.g., thiazolidinyl]. Examples of partially saturated heterocyclyl radicals include but are not limited to, dihydrothienyl, dihydropyranyl, dihydrofuryl, and dihydrothiazolyl. Examples of partially saturated and saturated heterocyclo groups include but are not limited to, pyrrolidinyl, imidazolidinyl, piperidinyl, pyrrolinyl, pyrazolidinyl, piperazinyl, morpholinyl, tetrahydropyranyl, thiazolidinyl, dihydrothienyl, 2,3-dihydro-benzo[1,4]dioxanyl, indolinyl, isoindolinyl, dihydrobenzothienyl, dihydrobenzofuryl, isochromanyl, chromanyl, 1,2-dihydroquinolyl, 1,2,3,4-tetrahydro-isoquinolyl, 1,2,3,4-tetrahydro-quinolyl, 2,3,4,4a,9,9a-hexahydro-1H-3-aza-fluorenyl, 5,6,7-trihydro-1,2,4-triazolo[3,4-a]isoquinolyl, 3,4-dihydro-2H-benzo[1,4]oxazinyl, benzo[1,4]dioxanyl, 2,3-dihydro-1H-1λ'-benzo[d]isothiazol-6-yl, dihydropyranyl, dihydrofuryl and dihydrothiazolyl.

Heterocyclo groups also include radicals where heterocyclic radicals are fused/condensed with aryl radicals: such as unsaturated condensed heterocyclic group containing 1 to 5 nitrogen atoms, for example, indoline, isoindoline, unsaturated condensed heterocyclic group containing 1 to 2 oxygen atoms and 1 to 3 nitrogen atoms, unsaturated condensed heterocyclic group containing 1 to 2 sulfur atoms and 1 to 3 nitrogen atoms, and saturated, partially unsaturated and unsaturated condensed heterocyclic group containing 1 to 2 oxygen or sulfur atoms.

"Saturated" means the referenced chemical structure does not contain any multiple carbon-carbon bonds. For example, a saturated cycloalkyl group as defined herein includes cyclohexyl, cyclopropyl, and the like.

"Unsaturated" means the referenced chemical structure contains at least one multiple carbon-carbon bond. For example, an unsaturated cycloalkyl group as defined herein includes cyclohexenyl, cyclopentenyl, cyclohexadienyl, and the like.

"Pharmaceutically acceptable salt" refers to both acid and base addition salts.

"Modulating" or "modulate" refers to the treating, prevention, suppression, enhancement or induction of a function, condition or disorder.

"Treating" or "treatment" refer to the treatment of a disease or disorder described herein, in a subject, preferably a human, and includes:
  i. inhibiting a disease or disorder, i.e., arresting its development;
  ii. relieving a disease or disorder, i.e., causing regression of the disorder;
  iii. slowing progression of the disorder; and/or
  iv. inhibiting, relieving, or slowing progression of one or more symptoms of the disease or disorder "Subject" or "Patient" refers to a warm blooded animal such as a mammal, preferably a human, or a human child, which is afflicted with, or has the potential to be afflicted with one or more diseases and disorders described herein.

A "prodrug" as used herein, means a compound which when administered to a host in vivo is converted into a parent drug. As used herein, the term "parent drug" means any of the presently described chemical compounds described herein. Prodrugs can be used to achieve any desired effect, including to enhance properties of the parent drug or to improve the pharmaceutic or pharmacokinetic properties of the parent. Prodrug strategies exist which provide choices in modulating the conditions for in vivo generation of the parent drug, all of which are deemed included herein. Nonlimiting examples of prodrug strategies include covalent attachment of removable groups, or removable portions of groups, for example, but not limited to acylation, phosphorylation, phosphonylation, phosphoramidate derivatives, amidation, reduction, oxidation, esterification, alkylation, other carboxy derivatives, sulfoxy or sulfone derivatives, carbonylation or anhydride, among others.

The present invention includes compounds of Formula A, Formula B, Formula C, and Formula D with at least one desired isotopic substitution of an atom, at an amount above the natural abundance of the isotope, i.e., enriched. Isotopes are atoms having the same atomic number but different mass numbers, i.e., the same number of protons but a different number of neutrons.

Examples of isotopes that can be incorporated into compounds of the invention include isotopes of hydrogen, carbon, nitrogen, oxygen, phosphorous, fluorine, chlorine and iodine such as $^2H$, $^3H$, $^{11}C$, $^{13}C$, $^{14}C$, $^{15}N$, $^{18}F$ $^{31}P$, $^{32}P$, $^{35}S$, $^{36}Cl$, and $^{125}I$ respectively. In one non-limiting embodiment, isotopically labelled compounds can be used in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

By way of general example and without limitation, isotopes of hydrogen, for example, deuterium ($^2H$) and tritium ($^3H$) may be used anywhere in described structures that achieves the desired result. Alternatively or in addition, isotopes of carbon, e.g., $^{13}C$ and $^{14}C$, may be used.

Isotopic substitutions, for example deuterium substitutions, can be partial or complete. Partial deuterium substitution means that at least one hydrogen is substituted with deuterium. In certain embodiments, the isotope is 90, 95 or 99% or more enriched in an isotope at any location of interest. In one non-limiting embodiment, deuterium is 90, 95 or 99% enriched at a desired location.

In one non-limiting embodiment, the substitution of a hydrogen atom for a deuterium atom can be provided in any of Formula A, Formula B, Formula C, and Formula D. In one non-limiting embodiment, the substitution of a hydrogen atom for a deuterium atom occurs within a group selected from any of $X_4$, B, C, $R_1$, $R_2$, $R_3$, and $R_4$. For example, when any of the groups are, or contain for example through substitution, methyl, ethyl, or methoxy, the alkyl residue may be deuterated (in non-limiting embodiments, $CDH_2$, $CD_2H$, $CD_3$, $CH_2CD_3$, $CD_2CD_3$, $CHDCH_2D$, $CH_2CD_3$, $CHDCHD_2$, $OCDH_2$, $OCD_2H$, or $OCD_3$ etc.). In certain other embodiments, when two substituents are combined to form a cycle the unsubstituted carbons may be deuterated.

The term "combination" is meant that the two selected compounds as described herein are administered in a single dosage form, or in two separate dosage forms given either simultaneously or consecutively, as long as they are provided in a manner that they can act in a concerted fashion to achieve the desired results. In one embodiment, a pharmaceutical composition is provided that includes at least the selected SERD and the selected CDK 4/6 inhibitor, either of which can be in the form of a pharmaceutically acceptable salt, in a pharmaceutically acceptable carrier.

As used herein the term "fulvestrant analog" is RU 58668 which has structure

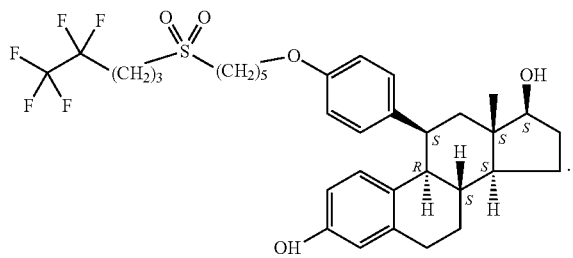

As used herein the term "GDC-0810" refers to the compound of structure

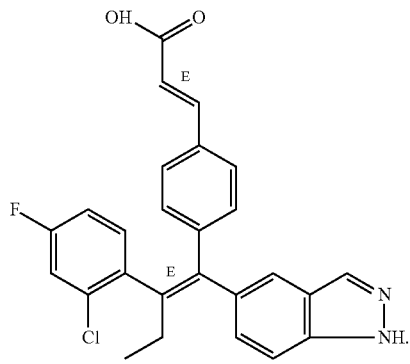 [SMILES: CC/C(=C(/c1ccc(/C=C/C(=O)O)cc1)c1ccc2[nH]ncc2c1)c1ccc(F)cc1Cl]

As used herein the term "AZD9496" refers to an estrogen receptor modulator developed by AstraZeneca that has the compound structure:

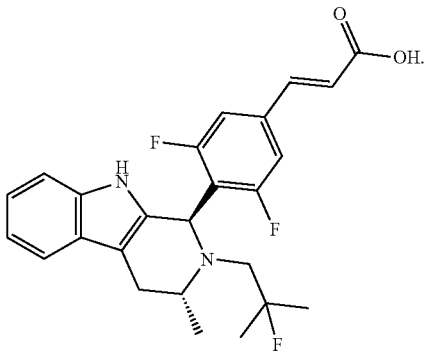 [SMILES: C[C@@H]1Cc2c([nH]c3ccccc23)[C@@H](c2c(F)cc(/C=C/C(=O)O)cc2F)N1CC(C)(C)F]

As used herein the term "PD-0332991" which is used interchangeably with "PD" is palbociclib, a drug for the treatment of breast cancer developed and marketed by Pfizer that has the structure:

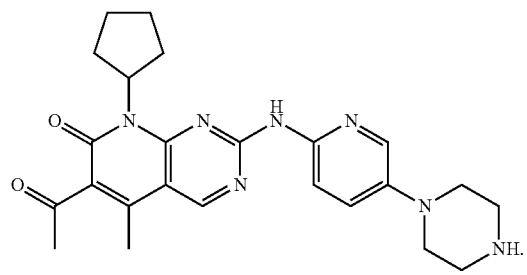 [SMILES: CC(=O)c1c(C)c2cnc(Nc3ccc(N4CCNCC4)cn3)nc2n(C2CCCC2)c1=O]

As used herein the term "Lasofoxifene" or "Laso" refers to the compound marketed under the brand name Fabyln by Pfizer that has the structure:

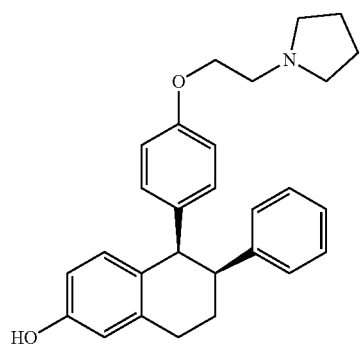 [SMILES: Oc1ccc2c(c1)CC[C@H](c1ccccc1)[C@@H]2c1ccc(OCCN2CCCC2)cc1]

As used herein the term "Fulvestrant" refers to the compound marketed under the brand name Faslodex by AstraZeneca that has the structure:

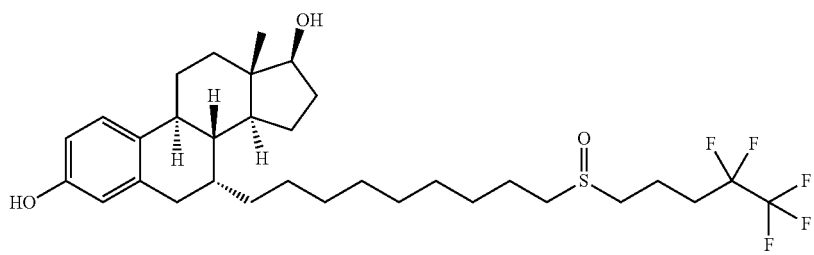

As used herein the term "Tamoxifen" as used interchangeably with "Tamoxifene" refers to the compound marketed under the brand name Nolvadex and has the structure:

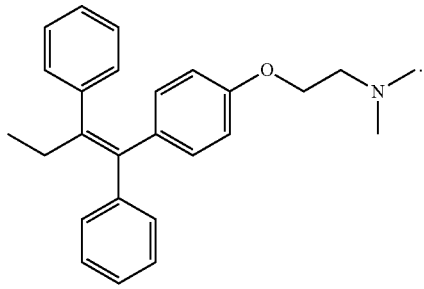 [SMILES: CC/C(=C(\c1ccccc1)c1ccc(OCCN(C)C)cc1)c1ccccc1]

The term "4-hydroxytamoxifen" or "4-hydroxytamoxifene" refers to the compound known as Afimoxifene which is being developed by Ascend Therapeutics and has the structure:

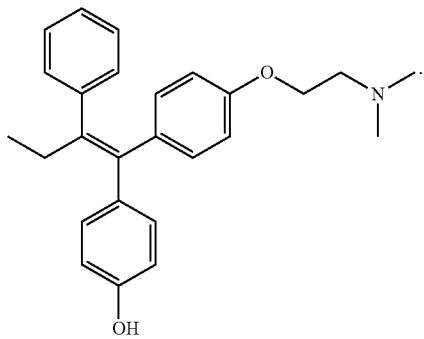 [SMILES: CC/C(=C(\c1ccc(O)cc1)c1ccc(OCCN(C)C)cc1)c1ccccc1]

The term "GW-5638" refers to Etacstil. Etacsil, which has antiestrogen properties, is converted in the body to "GW-7604", the hydroxylated derivative. Etacsil has the structure:

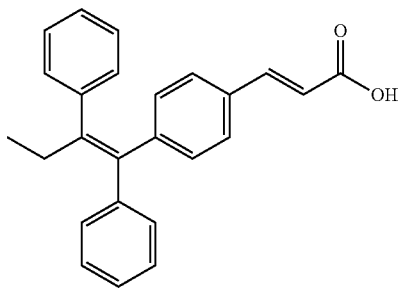 [SMILES: CC/C(=C(\c1ccccc1)c1ccc(/C=C/C(=O)O)cc1)c1ccccc1]

The term "GW-7604" refers to the bioavailable metabolite of prodrug GW-5638 which has the structure:

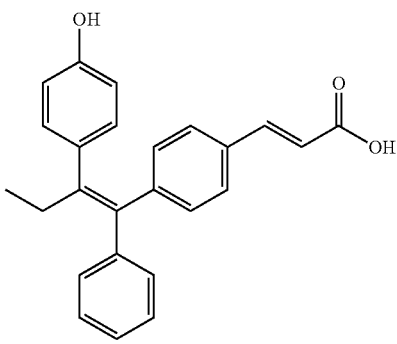 [SMILES: CC/C(=C(\c1ccccc1)c1ccc(/C=C/C(=O)O)cc1)c1ccc(O)cc1]

The term "raloxifene" refers to the compound marketed as Evista by Eli Lilly and Company which has the structure:

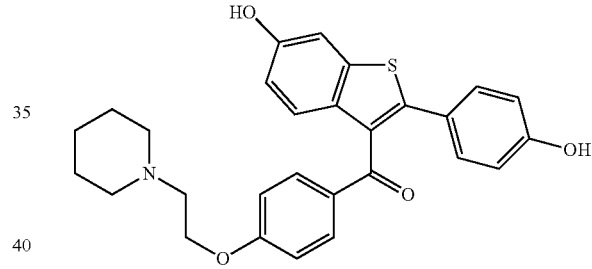

The term "bazedoxifene" refers to the SERM developed by developed and marketed by Pfizer which has the structure:

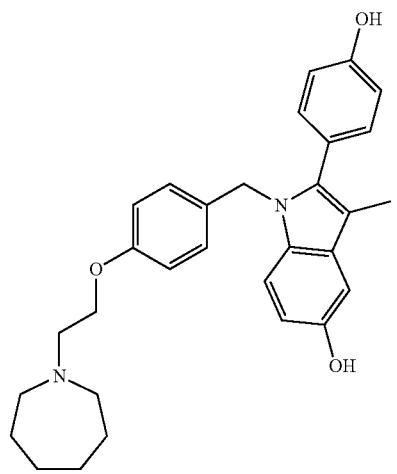 [SMILES: Cc1c(-c2ccc(O)cc2)n(Cc2ccc(OCCN3CCCCCC3)cc2)c2ccc(O)cc12]

The term "ribociclib" refers to the selective CDK4/6 inhibitor that has the structure:

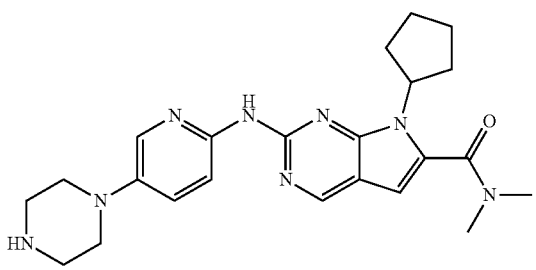 [SMILES: CN(C)C(=O)c1cc2cnc(Nc3ccc(N4CCNCC4)cn3)nc2n1C1CCCC1]

The term "abemaciclib" refers to the selective CDK4/6 inhibitor that has the structure:

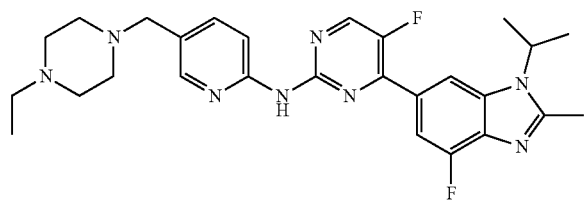 [SMILES: CCN1CCN(Cc2ccc(Nc3ncc(F)c(-c4cc(F)c5nc(C)n(C(C)C)c5c4)n3)nc2)CC1]

Palbociclib developed by Pfizer, ribociclib developed by Novartis and Astex Pharmaceuticals, and abemaciclib developed by Eli Lilly are three selective CDK4/6 inhibitors that have been studied in combination with aromatase inhibitors for the treatment of breast cancer. Palbociclib in combination with letrozole was granted accelerated approval by the FDA for the treatment of postmenopausal women with ER+/HER2− metastatic breast cancer who have not undergone endocrine-based therapy. Palbociclib in combination with fulvestrant is also FDA-approved as a second-line treatment for HR+/HER2− metastatic breast cancer following progression on endocrine therapy.

Ribociclib is FDA-approved for use in combination with an aromatase inhibitor for postmenopausal women with HR+/HER2− advanced breast cancer.

Abemaciclib (Lily) is in clinical trials with fulvestrant for the treatment of advanced HR+/HER2− breast cancer.

Pharmaceutical Compositions

This invention includes pharmaceutical compositions that include a therapeutically effective amount of an estrogen receptor downregulator compound as described herein (selected from Formula A, B, and C) or its pharmaceutically acceptable salt or prodrug, a CDK4/6 inhibitor as described herein (selected from Formula D) or its pharmaceutically acceptable salt or prodrug, and one or more of a pharmaceutically acceptable vehicles such as a diluent, preservative, solubilizer, emulsifier, adjuvant, excipient, or carrier. Excipients include, but are not limited to, liquids such as water, saline, glycerol, polyethylene glycol, hyaluronic acid, ethanol, and the like.

In some embodiments, the invention provides a "combination" (selected from Formula A, B, and C) or its pharmaceutically acceptable salt or prodrug, a CDK4/6 inhibitor as described herein (selected from Formula D) or its pharmaceutically acceptable salt or prodrug, wherein the selected compounds are administered in a single dosage form, or in two separate dosage forms given either simultaneously or consecutively, as long as they are provided in a manner that they can act in a concerted fashion to achieve the desired results. In one embodiment, a pharmaceutical composition is provided that includes at least the selected SERD and the selected CDK 4/6 inhibitor, either of which can be in the form of a pharmaceutically acceptable salt, optionally in a pharmaceutically acceptable carrier.

In one embodiment the pharmaceutical composition or combination comprises a compound of Formula A and a compound of Formula D. In one embodiment the pharmaceutical composition or combination comprises a compound of Formula B and a compound of Formula D. In one embodiment the pharmaceutical composition or combination comprises a compound of Formula C and a compound of Formula D. In another embodiment the pharmaceutical composition or combination comprises Compound 20 and Compound 23. In another embodiment the pharmaceutical composition or combination comprises Compound 21 and Compound 23.

To prepare the pharmaceutical compositions or combinations according to the present invention, a therapeutically effective amount of a compound of Formula A, Formula B, or Formula C and a compound of Formula D can be mixed with a pharmaceutically acceptable carrier according to conventional pharmaceutical compounding techniques to produce a fixed dosage form. A carrier may take a wide variety of forms depending on the form of preparation desired for administration, e.g., oral or parenteral. In preparing pharmaceutical compositions in oral dosage form, any of the usual pharmaceutical media may be used. For solid oral preparations such as powders, tablets, capsules, and for solid preparations such as suppositories, suitable carriers and additives including starches, sugar carriers, such as dextrose, manifold, lactose, and related carriers, diluents, granulating agents, lubricants, binders, disintegrating agents, and the like may be used. If desired, the tablets or capsules may be enteric-coated or sustained release by standard techniques. The use of these dosage forms may significantly enhance the bioavailability of the compounds in the patient. Thus, for liquid oral preparations such as suspensions, elixirs, and solutions, suitable carriers and additives including water, glycols, oils, alcohols, flavoring agents, preservatives, coloring agents, and the like may be used.

The term "pharmaceutically acceptable carrier" refers to a diluent, adjuvant, excipient or carrier with which a compound of the disclosure is administered. The terms "effective amount" or "pharmaceutically effective amount" refer to a nontoxic but sufficient amount of the agent to provide the desired biological result. That result can be reduction and/or alleviation of the signs, symptoms, or causes of a disease, or any other desired alteration of a biological system. An appropriate "effective" amount in any individual case can be determined by one of ordinary skill in the art using routine experimentation. "Pharmaceutically acceptable carriers" for therapeutic use are well known in the pharmaceutical art, and are described, for example, in Remington's Pharmaceutical Sciences, 18th Edition (Easton, Pa.: Mack Publishing Company, 1990). For example, sterile saline and phosphate-buffered saline at physiological pH can be used. Preservatives, stabilizers, dyes and even flavoring agents can be provided in the pharmaceutical composition. For example, sodium benzoate, sorbic acid and esters of p-hydroxybenzoic acid can be added as preservatives. Id. at 1449. In addition, antioxidants and suspending agents can be used. Id.

Suitable excipients for non-liquid formulations are also known to those of skill in the art. A thorough discussion of pharmaceutically acceptable excipients and salts is available in Remington's Pharmaceutical Sciences, 18th Edition (Easton, Pa.: Mack Publishing Company, 1990).

Additionally, auxiliary substances, such as wetting or emulsifying agents, biological buffering substances, surfactants, and the like, can be present in such vehicles. A biological buffer can be any solution which is pharmacologically acceptable and which provides the formulation with the desired pH, i.e., a pH in the physiologically acceptable range. Examples of buffer solutions include saline, phosphate buffered saline, Tris buffered saline, Hank's buffered saline, and the like.

Depending on the intended mode of administration, the pharmaceutical compositions or combinations can be in the form of solid, semi-solid or liquid dosage forms, such as, for example, tablets, suppositories, pills, capsules, powders, liquids, suspensions, creams, ointments, lotions or the like, preferably in unit dosage forms suitable for administration of a precise dosage.

In general, the compositions or combinations of the disclosure will be administered in a therapeutically effective amount by any of the accepted modes of administration. Suitable dosage ranges depend upon numerous factors such as the severity of the disease to be treated, the age and relative health of the subject, the potency of the compound used, the route and form of administration, the indication being treated, and the preferences and experience of the medical practitioner involved. One of ordinary skill in the art of treating such diseases will be able, without undue experimentation and in reliance upon personal knowledge and the disclosure of this application, to ascertain a therapeutically effective amount of the compositions of the disclosure for a given disease.

Compositions or combinations for administration of the active compound include but are not limited to those suitable for oral (including but not limited to a tablet, capsule, liquid, gel formulation), topical, rectal, nasal, pulmonary, parenteral (including intramuscular, intra-arterial, intrathecal, subcutaneous and intravenous), intramuscular, intravenous, subcutaneous, transdermal (which may include a penetration enhancement agent), vaginal and suppository administration. Enteric coated oral tablets may also be used to enhance bioavailability of the compounds for an oral route of administration. The most effective dosage form will depend upon the bioavailability/pharmacokinetics of the particular compound chosen as well as the severity of disease in the patient. Oral dosage forms are typical, because of ease of administration and prospective favorable patient compliance.

For solid compositions, conventional nontoxic solid carriers include, for example, pharmaceutical grades of mannitol, lactose, starch, magnesium stearate, sodium saccharin, talc, cellulose, glucose, sucrose, magnesium carbonate, and the like. Liquid pharmaceutically administrable compositions can, for example, be prepared by dissolving, dispersing, and the like, an active compound as described herein and optional pharmaceutical adjuvants in an excipient, such as, for example, water, saline, aqueous dextrose, glycerol, ethanol, and the like, to thereby form a solution or suspension. If desired, the pharmaceutical composition to be administered can also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, and the like. Actual methods of preparing such dosage forms are known, or will be apparent, to those skilled in this art; for example, see Remington's Pharmaceutical Sciences, referenced above.

Yet another embodiment is the use of permeation enhancer excipients including polymers such as: polycations (for example chitosan and its quaternary ammonium derivatives, poly-L-arginine, and aminated gelatin); polyanions (for example N-carboxymethyl chitosan and poly-acrylic acid); and, thiolated polymers (for example carboxymethyl cellulose-cysteine, polycarbophil-cysteine, chitosan-thiobutylamidine, chitosan-thioglycolic acid, and chitosan-glutathione conjugates).

For oral administration, the composition or combination will generally take the form of one or more tablets, capsules, softgel capsules or can be an aqueous or nonaqueous solution, suspension or syrup. Tablets and capsules are typical oral administration forms. Tablets and capsules for oral use can include one or more commonly used carriers such as lactose and corn starch. Lubricating agents, such as magnesium stearate, are also typically added. Typically, the compositions of the disclosure can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

When liquid suspensions are used, the pharmaceutical composition or combinations can be combined with any oral, non-toxic, pharmaceutically acceptable inert carrier such as ethanol, glycerol, water, and the like and with emulsifying and suspending agents. If desired, flavoring, coloring and/or sweetening agents can be added as well. Other optional components for incorporation into an oral formulation herein include, but are not limited to, preservatives, suspending agents, thickening agents, and the like.

Parenteral formulations can be prepared in conventional forms, either as liquid solutions or suspensions, solid forms suitable for solubilization or suspension in liquid prior to injection, or as emulsions. Preferably, sterile injectable suspensions are formulated according to techniques known in the art using suitable carriers, dispersing or wetting agents and suspending agents. The sterile injectable formulation can also be a sterile injectable solution or a suspension in an acceptable nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Parenteral administration includes intraarticular, intravenous, intramuscular, intradermal, intraperitoneal, and subcutaneous routes, and include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Administration via certain parenteral routes can involve introducing the formulations of the disclosure into the body of a patient through a needle or a catheter, propelled by a sterile syringe or some other mechanical device such as a continuous infusion system. A formulation provided by the disclosure can be administered using a syringe, injector, pump, or any other device recognized in the art for parenteral administration.

Preferably, sterile injectable suspensions are formulated according to techniques known in the art using suitable carriers, dispersing or wetting agents and suspending agents. The sterile injectable formulation can also be a sterile injectable solution or a suspension in a nontoxic parenterally acceptable diluent or solvent. Among the acceptable vehicles and solvents that can be employed are water, Ringer's solution and isotonic sodium chloride solution. In addition, sterile, fixed oils, fatty esters or polyols are conventionally employed as solvents or suspending media. In addition, parenteral administration can involve the use of a slow release or sustained release system such that a constant level of dosage is maintained.

Preparations according to the disclosure for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms can also contain adjuvants such as preserving, wetting, emulsifying, and dispersing agents. They can be sterilized by, for example, filtration through a bacteria retaining filter, by incorporating sterilizing agents into the compositions, by irradiating the compositions, or by heating the compositions. They can also be manufactured using sterile water, or some other sterile injectable medium, immediately before use.

Sterile injectable solutions are prepared by incorporating one or more of the compounds of the disclosure in the required amount in the appropriate solvent with various of the other ingredients enumerated above, as required, followed by filtered sterilization. Generally, dispersions are prepared using a combination of the compound of Formula A, Formula B, or Formula C, and the compound of Formula D into one or more sterile vehicles which contain the basic dispersion medium and the required other ingredients from those enumerated above. In the case of sterile powders for the preparation of sterile injectable solutions, examples of methods of preparation are vacuum-drying and freeze-drying techniques which yield a powder of the compound of Formula A, Formula B, or Formula C, and the compound of Formula D plus any additional desired ingredient from a previously sterile-filtered solution thereof. Thus, for example, a parenteral composition suitable for administration by injection is prepared by stirring 1.5% by weight of the compound of Formula A, Formula B, or Formula C, and the compound of Formula D in 10% by volume propylene glycol and water. Or the selected compounds can be administered separated but for concerted effect. The solution is made isotonic with sodium chloride and sterilized.

Alternatively, the pharmaceutical compositions or combinations of the disclosure can be administered in the form of suppositories for rectal administration. These can be prepared by mixing the agent with a suitable nonirritating excipient which is solid at room temperature but liquid at the rectal temperature and therefore will melt in the rectum to release the compounds. Such materials include cocoa butter, beeswax and polyethylene glycols.

The pharmaceutical compositions of the disclosure can also be administered by nasal aerosol or inhalation. Such compositions are prepared according to techniques well-known in the art of pharmaceutical formulation and can be prepared as solutions in saline, employing benzyl alcohol or other suitable preservatives, absorption promoters to enhance bioavailability, propellants such as fluorocarbons or nitrogen, and/or other conventional solubilizing or dispersing agents.

Preferred formulations for topical delivery are ointments and creams. Ointments are semisolid preparations which are typically based on petrolatum or other petroleum derivatives. Creams containing the selected pharmaceutical composition, are, as known in the art, viscous liquid or semisolid emulsions, either oil-in-water or water-in-oil. Cream bases are water-washable, and contain an oil phase, an emulsifier and an aqueous phase. The oil phase, also sometimes called the "internal" phase, is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation is generally a nonionic, anionic, cationic or amphoteric surfactant. The specific ointment or cream base to be used, as will be appreciated by those skilled in the art, is one that will provide for optimum drug delivery. As with other carriers or vehicles, an ointment base should be inert, stable, nonirritating and nonsensitizing.

Formulations for buccal administration include tablets, lozenges, gels and the like. Alternatively, buccal administration can be effected using a transmucosal delivery system as known to those skilled in the art. The compounds of the disclosure can also be delivered through the skin or mucosal tissue using conventional transdermal drug delivery systems, i.e., transdermal "patches" wherein the agent is typically contained within a laminated structure that serves as a drug delivery device to be affixed to the body surface. In such a structure, the drug composition is typically contained in a layer, or "reservoir," underlying an upper backing layer. The laminated device can contain a single reservoir, or it can contain multiple reservoirs. In one embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, can be either a polymeric matrix as described above, or it can be a liquid or gel reservoir, or can take some other form. The backing layer in these laminates, which serves as the upper surface of the device, functions as the primary structural element of the laminated structure and provides the device with much of its flexibility. The material selected for the backing layer should be substantially impermeable to the pharmaceutical composition and any other materials that are present.

The compositions or combinations of the disclosure can be formulated for aerosol administration, particularly to the respiratory tract and including intranasal administration. The compound may, for example generally have a small particle size, for example of the order of 5 microns or less. Such a particle size can be obtained by means known in the art, for example by micronization. The compound of Formula A, Formula B, or Formula C, and the compound of Formula D is provided in a pressurized pack with a suitable propellant such as a chlorofluorocarbon (CFC) for example dichlorodifluoromethane, trichlorofluoromethane, or dichlorotetrafluoroethane, carbon dioxide or other suitable gas. The aerosol can conveniently also contain a surfactant such as lecithin. The dose of drug can be controlled by a metered valve.

Alternatively, the compound of Formula A, Formula B, or Formula C, and the compound of Formula D can be provided in a form of a dry powder, for example a powder mix of the compound in a suitable powder base such as lactose, starch, starch derivatives such as hydroxypropylmethyl cellulose and polyvinylpyrrolidine (PVP). The powder carrier will form a gel in the nasal cavity. The powder composition can be presented in unit dose form for example in capsules or cartridges of e.g., gelatin or blister packs from which the powder can be administered by means of an inhaler.

A pharmaceutically or therapeutically effective amount of the composition or combination should be delivered to the subject to achieve the desired result. The precise effective amount will vary from subject to subject and will depend upon the species, age, the subject's size and health, the nature and extent of the condition being treated, recommendations of the treating physician, and the therapeutics or combination of therapeutics selected for administration. The effective amount for a given situation can be determined by routine experimentation. For purposes of the disclosure, a therapeutic amount may for example be in the range of about 0.01 mg/kg to about 250 mg/kg body weight, more preferably about 0.1 mg/kg to about 10 mg/kg, in at least one dose. In some non-limiting embodiments, the daily dosage may be from about 1 mg to 300 mg, one or more times per day, more preferably in the range of about 10 mg to 200 mg. The subject can be administered in as many doses as is required to reduce and/or alleviate the signs, symptoms, or causes of the disorder in question, or bring about any other desired alteration of a biological system. When desired, formulations can be prepared with enteric coatings adapted for sustained or controlled release administration of the compound of Formula A, Formula B, or Formula C, and the compound of Formula D.

In some embodiments, for example, the dosage may be the amount of a compound of the combination needed to provide a serum concentration of the active compound of up to about 10 nM, 50 nM, 100 nM, 200 nM, 300 nM, 400 nM, 500 nM, 600 nM, 700 nM, 800 nM, 900 nM, 1 µM, 5 µM, 10 µM, 20 µM, 30 µM, or 40 µM.

In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of at least one of the active compounds of the combination and optionally from about 0.1 mg to about 2000 mg, from about 10 mg to about 1000 mg, from about 100 mg to about 800 mg, or from about 200 mg to about 600 mg of an additional active agent in a unit dosage form. Examples of dosage forms are those with at least, or no greater than, 1, 2, 5, 10, 15, 20, 25, 50, 75, 100, 150, 200, 250, 300, 350, 400, 450, 500, 550, 600, 650, 700, or 750 mg of active compound, or its salt or prodrug. The pharmaceutical composition or combination may also include a molar ratio of the active compound and an additional active agent, in a ratio that achieves the desired results.

The unit dosage form can be for example, a packaged preparation containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Methods of Treatment

The compounds of the invention in combination as taught herein may be used in methods for treatment or prevention of abnormal cellular proliferation, including a cancer or tumor that is sensitive to such treatment. The cancer may be for example a breast cancer, a uterine cancer, an ovarian cancer, endometrial, a prostate cancer, or a lung cancer. Particularly, the breast cancer may be a tamoxifen resistant breast cancer or a triple negative breast cancer.

In one embodiment the cancer or tumor has one or more endocrine resistant ER mutations. In one embodiment the endocrine resistant ER mutation is ER-Y535S. In another embodiment the endocrine resistant ER mutation is ER-D538G.

In an embodiment the method of treatment comprises administering to a patient in need thereof an effective amount of a CDK4/6 inhibitor of Formula D in combination with an estrogen receptor downregulator selected from Formula A, B or C.

In some aspects, the combination described herein may prevent or reduce the risk of cancer or a tumor. The method of treatment may cause partial or complete regression of cancer or a tumor in a subject.

The method of treatment may cause partial or complete regression of a tamoxifen resistant cancer or tumor. The method of treatment may cause partial or complete regression of a triple negative breast cancer.

In other embodiments, the compound or its pharmaceutically acceptable salt or prodrug or a pharmaceutical composition or combination thereof can be used to prevent recurrence of a cancer or tumor after treatment, as adjunctive therapy. In one example, the compound or its pharmaceutically acceptable salt or prodrug or a pharmaceutical composition thereof can be used to prevent further breast cancer after breast cancer treatment or to treat node-positive breast cancer in women following mastectomy and/or radiation.

If desired, multiple doses of the compounds described herein can be administered to the subject. Alternatively, the subject can be given a single dose of a combination described herein.

In one aspect of the invention, the method of treatment disclosed herein can be beneficially administered in combination with any therapeutic regimen entailing radiotherapy, chemotherapy, or other therapeutic agents.

In some embodiments, the method of treatment disclosed herein is used to treat or prevent cancer or a tumor in a mammal such as a human. In some embodiments, the cancer is breast cancer, ovarian cancer, endometrial cancer, prostate cancer, or uterine cancer. In some embodiments, the cancer is breast cancer, lung cancer, ovarian cancer, endometrial cancer, prostate cancer, or uterine cancer. In some embodiments, the cancer is breast cancer. In some embodiments, the cancer is a hormone dependent cancer. In some embodiments, the cancer is an estrogen receptor dependent cancer. In some embodiments, the cancer is an estrogen-sensitive cancer. In some embodiments, the cancer is resistant to anti-hormonal treatment. In some embodiments, the cancer is an estrogen-sensitive cancer or an estrogen receptor dependent cancer that is resistant to anti-hormonal treatment. In some embodiments, the cancer is a hormone-sensitive cancer or a hormone receptor dependent cancer that is resistant to anti-hormonal treatment. In some embodiments, anti-hormonal treatment includes treatment with at least one agent selected from tamoxifen, fulvestrant, steroidal aromatase inhibitors, and non-steroidal aromatase inhibitors.

In some embodiments, the method of treatment disclosed herein is used to treat hormone receptor positive metastatic breast cancer in a postmenopausal woman with disease progression following anti-estrogen therapy.

In some embodiments, the method of treatment disclosed herein are used to treat a hormonal dependent benign or malignant disease of the breast or reproductive tract in a mammal. In some embodiments, the benign or malignant disease is breast cancer.

The foregoing may be better understood by reference to the following Examples, which are presented for purposes of illustration and are not intended to limit the scope of the invention.

In one aspect, the method of treatment of the present invention or its pharmaceutically acceptable salt or prodrug, can be used to treat a hormone-related cancer or tumor that has metastasized to the brain, bone or other organ. In one embodiment of this aspect, the hormone-related cancer is estrogen mediated. In another embodiment, the estrogen mediated cancer is selected from breast, uterine, ovarian and endometrial. In other embodiments, the method of treatment can be used to prevent a hormone-related cancer or tumor from metastasizing to the brain, bone or other organ, including a hormone-related cancer that is estrogen mediated, for example, breast, uterine, ovarian or endometrial.

Synthetic Methods

The compounds described herein can be prepared by methods known by those skilled in the art. In one non-limiting example the disclosed compounds can be prepared using the schemes.

As used herein alkenylene can encompass both cis and trans isomers of alkenes, unless indicated otherwise. In one embodiment the isomer is cis. In a preferred embodiment the isomer is trans. In one embodiment $R_2$ is $—C_2$-$C_6$alkenylene-$COOR_{17}$ and the alkene group is cis. In a preferred embodiment $R_2$ is $—C_2$-$C_6$alkenylene-$COOR_{17}$ and the alkene group is trans.

Some of the compounds described herein can have a chiral center, and the compound can exist in isomeric or diastereomeric form. When multiple chiral variables are present on formulas of the present invention, the formula further encompasses every possible diastereomer unless indicated otherwise, or otherwise clear from the context. For example (R,R), (S,R), (S,S), and (R,S) for a molecule with two chiral centers. One skilled in the art will recognize that pure enantiomers, diastereomers, and cis/trans isomers can be prepared by methods known in the art. Examples of methods to obtain optically active materials include at least the following.

i) Physical separation of crystals—a technique whereby macroscopic crystals of the individual enantiomers are manually separated. This technique can be used if crystals of the separate enantiomers exist, i.e., the material is a conglomerate, and the crystals are visually distinct;

ii) Simultaneous crystallization—a technique whereby individual enantiomers are separately crystallized from a solution of the racemate, possible only if the latter is a conglomerate in the solid state;

iii) Enzymatic resolutions—a technique whereby partial or complete separation of a racemate by virtue of differing rates of reaction for the enantiomers with an enzyme;

iv) Enzymatic asymmetric synthesis—a synthetic technique whereby at least one step of the synthesis uses an enzymatic reaction to obtain an enantiomerically pure or enriched synthetic precursor of the desired enantiomer;

v) Chemical asymmetric synthesis—a synthetic technique whereby the desired enantiomer is synthesized from an achiral precursor under conditions that produce asymmetry (i.e., chirality) in the product, which may be achieved using chiral catalysts or chiral auxiliaries;

vi) Diastereomer separations—a technique whereby a racemic compound is reacted with an enantiomerically pure reagent (the chiral auxiliary) that converts the individual enantiomers to diastereomers. The resulting diastereomers are then separated by chromatography or crystallization by virtue of their now more distinct structural differences and the chiral auxiliary later removed to obtain the desired enantiomer;

vii) First- and second-order asymmetric transformations—a technique whereby diastereomers from the racemate equilibrate to yield a preponderance in solution of the diastereomer from the desired enantiomer or where preferential crystallization of the diastereomer from the desired enantiomer perturbs the equilibrium such that eventually in principle all the material is converted to the crystalline diastereomer from the desired enantiomer. The desired enantiomer is then released from the diastereomer;

viii) Kinetic resolutions—this technique refers to the achievement of partial or complete resolution of a racemate (or of a further resolution of a partially resolved compound) by virtue of unequal reaction rates of the enantiomers with a chiral, non-racemic reagent or catalyst under kinetic conditions;

ix) Enantiospecific synthesis from non-racemic precursors—a synthetic technique whereby the desired enantiomer is obtained from non-chiral starting materials and where the stereochemical integrity is not or is only minimally compromised over the course of the synthesis;

x) Chiral liquid chromatography—a technique whereby the enantiomers of a racemate are separated in a liquid mobile phase by virtue of their differing interactions with a stationary phase (including via chiral HPLC). The stationary phase can be made of chiral material or the mobile phase can contain an additional chiral material to provoke the differing interactions;

xi) Chiral gas chromatography—a technique whereby the racemate is volatilized and enantiomers are separated by virtue of their differing interactions in the gaseous mobile phase with a column containing a fixed non-racemic chiral adsorbent phase;

xii) Extraction with chiral solvents—a technique whereby the enantiomers are separated by virtue of preferential dissolution of one enantiomer into a particular chiral solvent;

xiii) Transport across chiral membranes—a technique whereby a racemate is placed in contact with a thin membrane barrier. The barrier typically separates two miscible fluids, one containing the racemate, and a driving force such as concentration or pressure differential causes preferential transport across the membrane barrier. Separation occurs as a result of the non-racemic chiral nature of the membrane that allows only one enantiomer of the racemate to pass through.

xiv) Simulated moving bed chromatography, is used in one embodiment. A wide variety of chiral stationary phases are commercially available.

EXAMPLES

Example 1. General Synthetic Routes

General Synthetic Route 1 (Formula A):

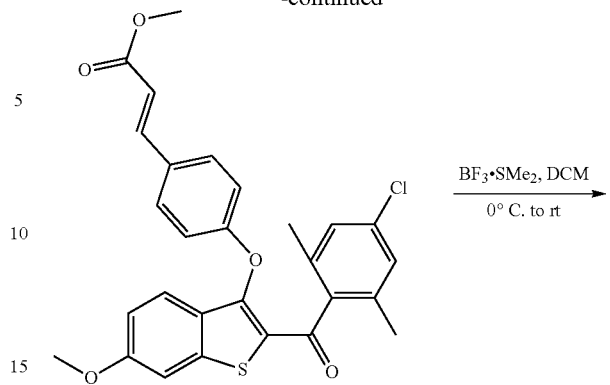

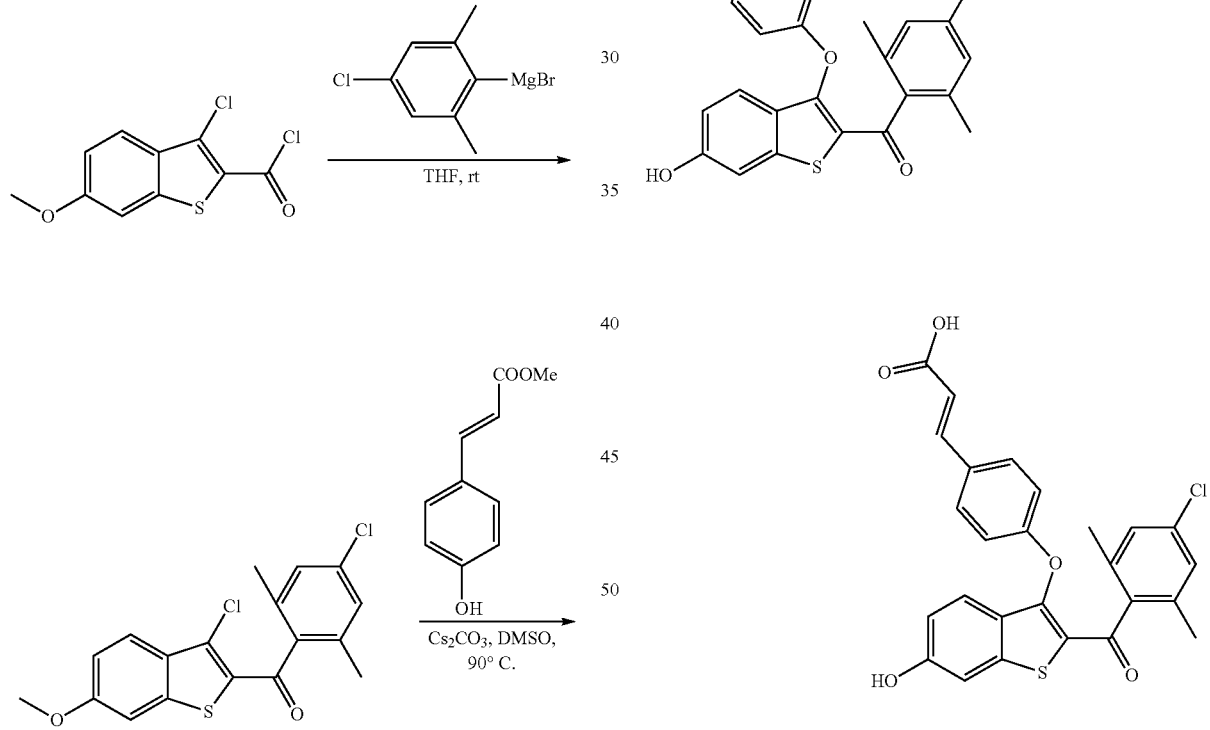

General Synthetic Route 2 (Formula B):

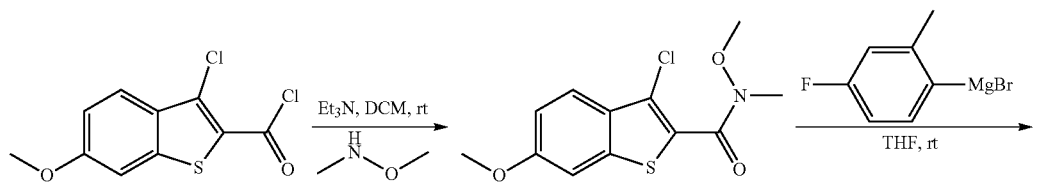

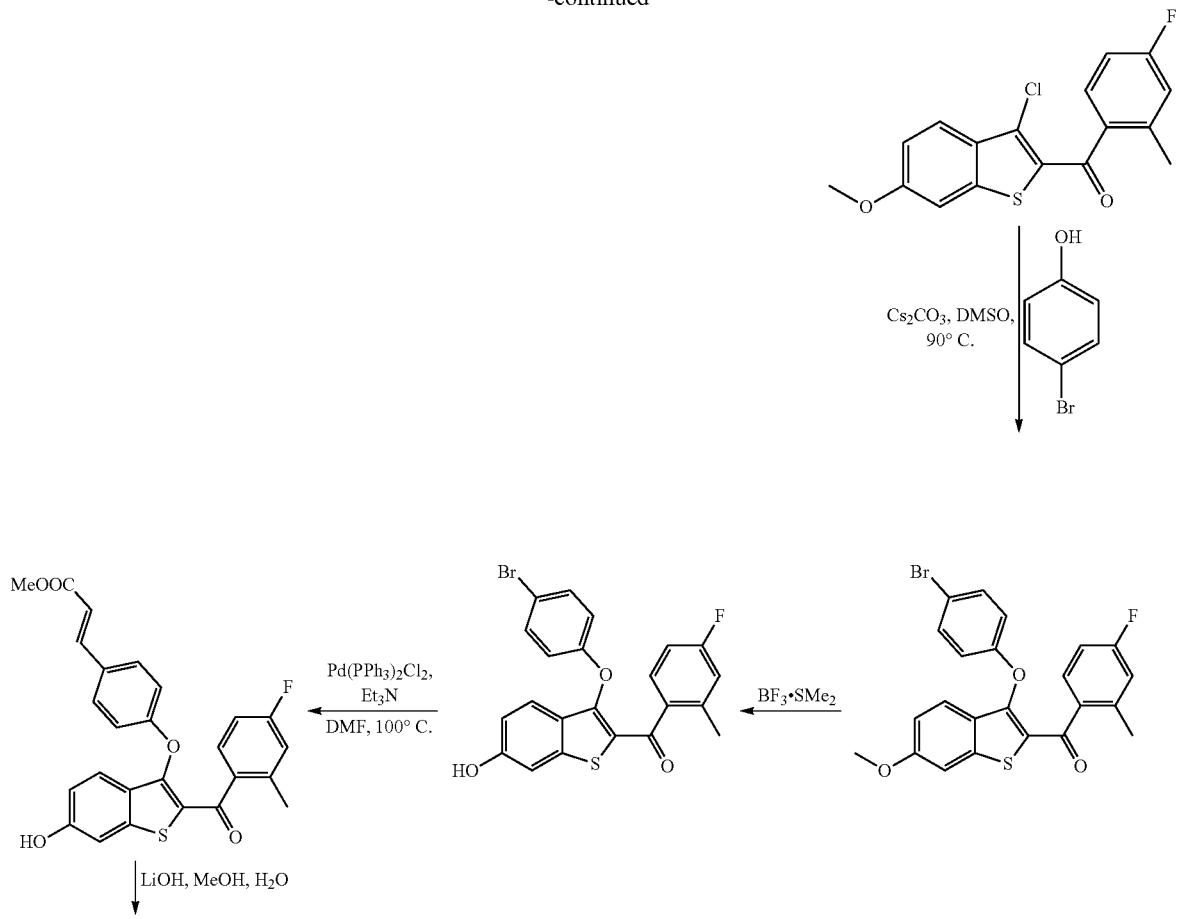
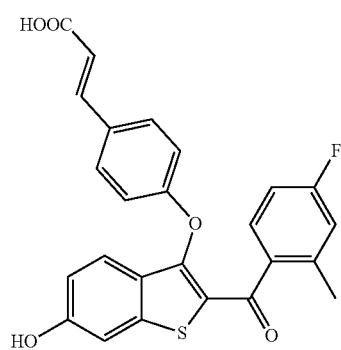
General Synthetic Route 3 (Formula B):
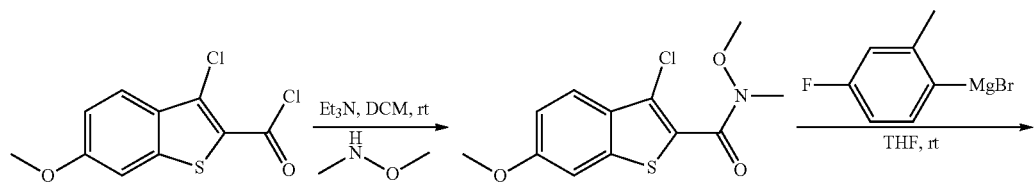

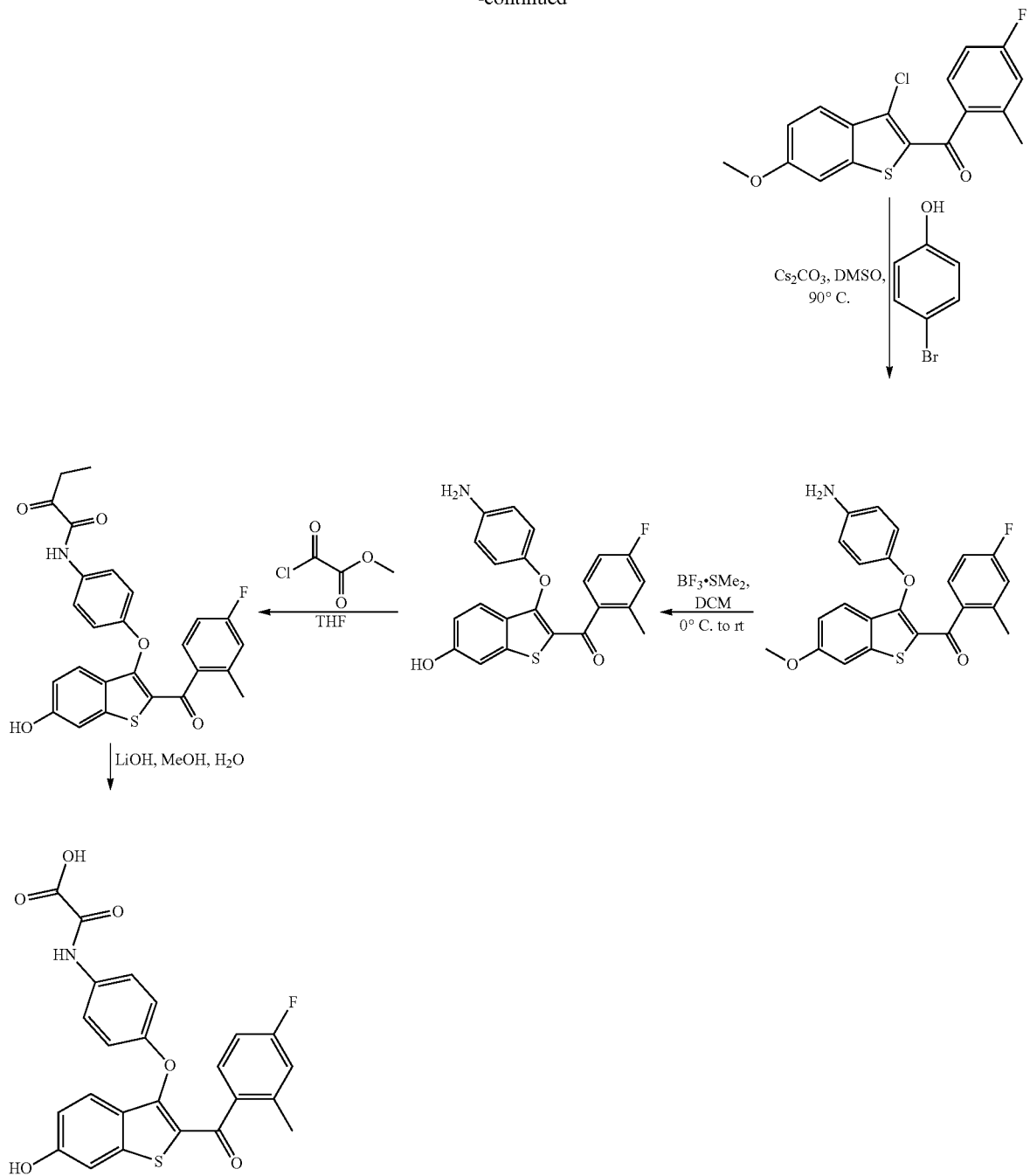
General Synthetic Route 4 (Formula B):
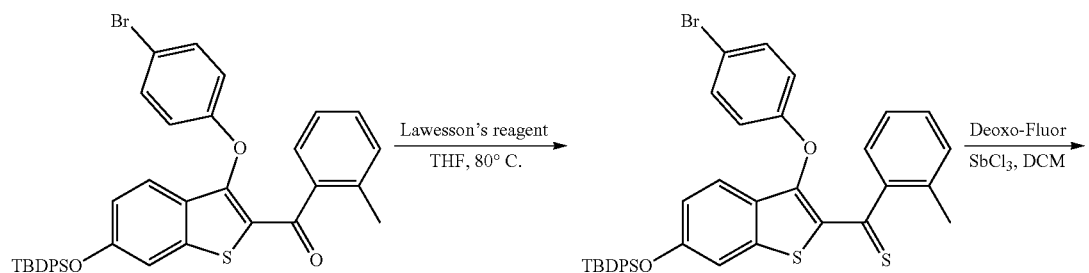

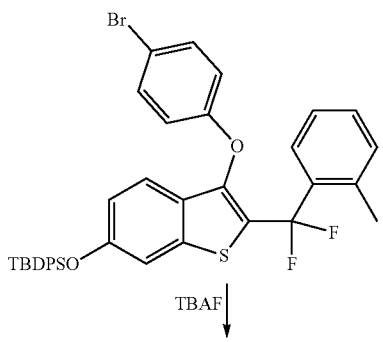
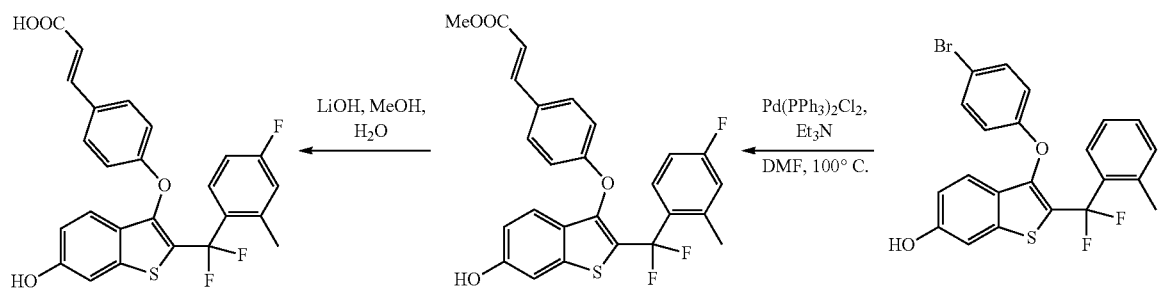
General Synthetic Route 5 (Formula B):
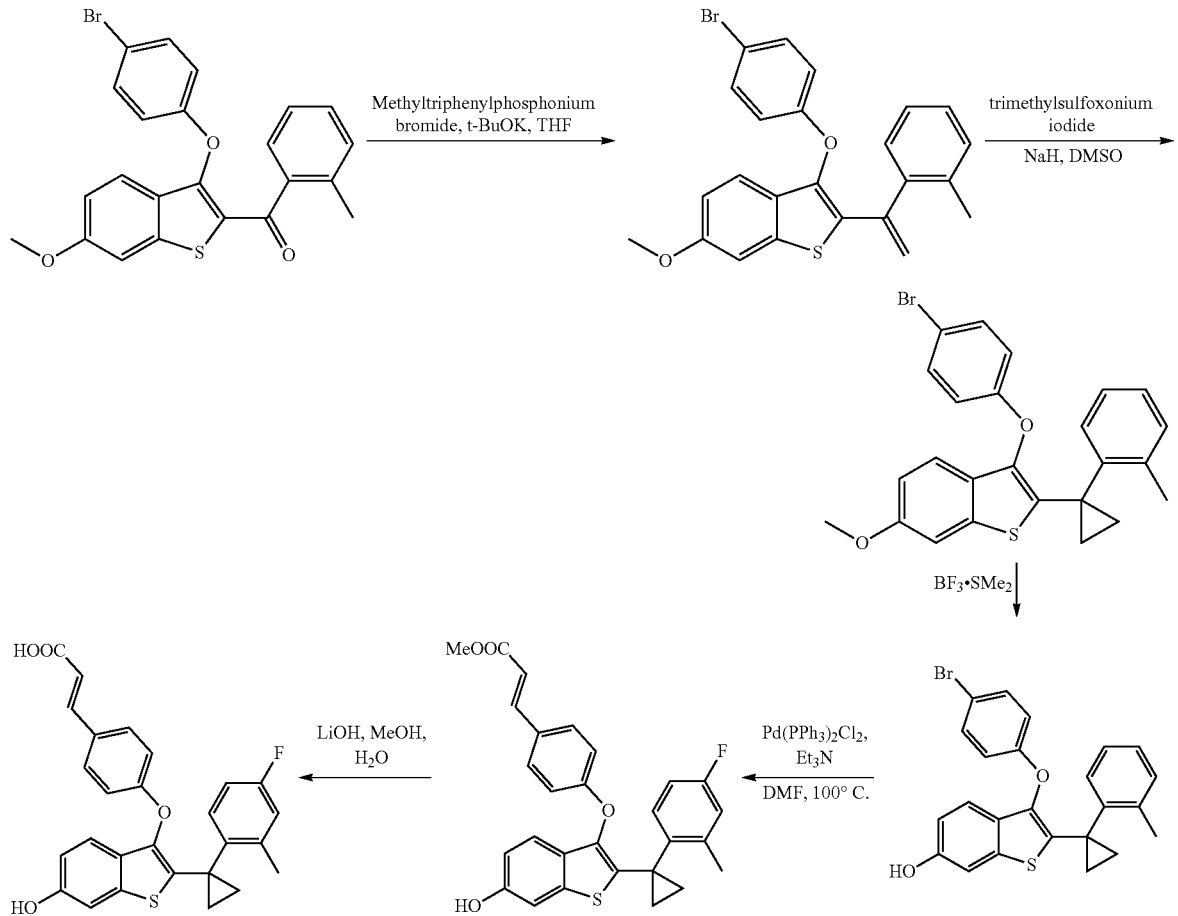

Example 2. Synthesis and Characterization of Synthetic Intermediates

Scheme 1: Synthesis of (3-Chloro-6-methoxybenzo[b]thiophen-2-yl)(4-fluoro-2-methylphenyl)methanone (I-3)

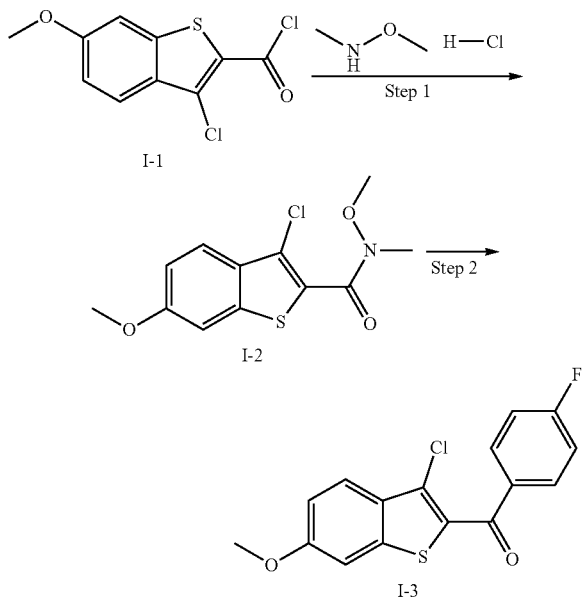

Step 1: Synthesis of 3-Chloro-N,6-dimethoxy-N-methylbenzo[b]thiophene-2-carboxamide (I-2)

In an oven-dried round-bottom flask, 3-chloro-6-methoxybenzo[b]thiophene-2-carbonyl chloride (I-2, 8.9 g, 34.9 mmol) was dissolved in 50 mL of anhydrous dichloromethane under argon atmosphere and N,O-dimethylhydroxylamine hydrochloride (3.75 g, 38.4 mmol) was added in one portion. After stirring for 10 minutes, Et$_3$N (17.6 g, 174.5 mmol) was added drop-wise. The reaction mixture was stirred overnight until TLC indicated consumption of all starting materials. The reaction was quenched by ice water, the solution was extracted with ethyl acetate, and washed with brine. The organic extracts were combined, dried over anhydrous Na$_2$SO$_4$, concentrated in vacuum, and purified by flash chromatography (5%-50% ethyl acetate in hexane) to afford 7.6 g I-3 as a white solid (76%). $^1$H NMR (400 MHz, CDCl$_3$) δ 7.82 (d, J=8.9 Hz, 1H), 7.23 (s, 1H), 7.10 (dd, J=8.9, 2.3 Hz, 1H), 3.90 (s, 3H), 3.73 (s, 3H), 3.39 (s, 3H). $^{13}$C NMR (100 MHz, CDCl$_3$) δ 162.04, 159.88, 140.35, 130.23, 124.19, 116.09, 104.29, 62.04, 55.87, 33.75.

Step 2: Synthesis of (3-Chloro-6-methoxybenzo[b]thiophen-2-yl)(4-fluoro-2-methylphenyl)methanone (I-3)

To a solution of intermediate (1) (500 mg, 1.75 mmol) in THF under argon atmosphere was added a 0.5 M solution of (4-fluoro-2-methylphenyl)magnesium bromide (4 mL, 2 mmol) drop-wise. The reaction mixture was stirred overnight and quenched by 1 N HCl/ice water. The solution was extracted with ethyl acetate and washed with brine. The organic extracts were combined, dried over anhydrous Na$_2$SO$_4$, concentrated in vacuum, and purified by flash chromatography (1%-15% ethyl acetate in hexane) to afford 550 mg of a white solid (94%).

Intermediates shown below in Table 1 were synthesized by an analogous procedure to the synthesis of compound I-3 utilizing the appropriate Grignard reagent. The characterization of each intermediate is shown along with the name and structure.

TABLE 1

Compound structure and characterization of intermediates synthesized analogously to compound I-3

| Structure | Name | Characterization |
|---|---|---|
| (3-Chloro-6-methoxybenzo[b]thiophen-2-yl) with 4-methoxyphenyl methanone structure | (3-Chloro-6-methoxybenzo[b]thiophen-2-yl)(4-methoxyphenyl)methanone | $^1$H NMR (400 MHz, CDCl$_3$) δ 7.93-7.86 (m, 2H), 7.81 (d, J = 8.9 Hz, 1H), 7.25 (d, J = 1.5 Hz, 1H), 7.11 (dd, J = 8.9, 2.2 Hz, 1H), 7.00-6.88 (m, 2H), 3.90 (s, 3H), 3.89 (s, 3H). $^{13}$C NMR (100 MHz, CDCl$_3$) δ 187.57, 163.95, 160.22, 140.70, 132.50, 132.12, 131.07, 130.63, 124.64, 123.70, 116.54, 113.83, 104.54, 55.91, 55.67. |
| (3-Chloro-6-methoxybenzo[b]thiophen-2-yl) with 2-ethylphenyl methanone structure | (3-Chloro-6-methoxybenzo[b]thiophen-2-yl)(2-ethylphenyl)methanone | $^1$H NMR (400 MHz, CDCl$_3$) δ 7.80 (d, J = 9.0 Hz, 1H), 7.45 (td, J = 7.6, 1.3 Hz, 1H), 7.40-7.32 (m, 2H), 7.30-7.26 (m, 1H), 7.24 (d, J = 2.2 Hz, 1H), 7.09 (dd, J = 9.0, 2.3 Hz, 1H), 3.91 (s, 3H), 2.74 (q, J = 7.5 Hz, 2H), 1.21 (t, J = 7.6 Hz, 3H). $^{13}$C NMR (100 MHz, CDCl$_3$) δ 191.07, 160.96, 142.52, 141.85, 139.10, 134.02, 131.67, 130.80, 129.48, 127.86, 125.73, 125.36, 116.86, 104.50, 55.92, 26.38, 15.81. |

TABLE 1-continued

Compound structure and characterization of intermediates synthesized analogously to compound I-3

| Structure | Name | Characterization |
|---|---|---|
| 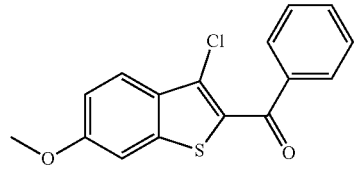 [SMILES: COc1ccc2c(Cl)c(C(=O)c3ccccc3)sc2c1] | (3-Chloro-6-methoxybenzo[b]thiophen-2-yl)(phenyl)methanone | ¹H NMR (400 MHz, CDCl₃) δ 7.92-7.78 (m, 3H), 7.61 (t, J = 7.4 Hz, 1H), 7.49 (t, J = 7.6 Hz, 2H), 7.26 (d, J = 2.3 Hz, 1H), 7.12 (dd, J = 9.0, 2.3 Hz, 1H), 3.92 (s, 3H). ¹³C NMR (100 MHz, CDCl₃) δ 188.94, 160.37, 140.96, 138.08, 132.88, 131.76, 131.05, 129.56, 128.34, 124.86, 124.77, 116.59, 104.31, 55.76. |
| 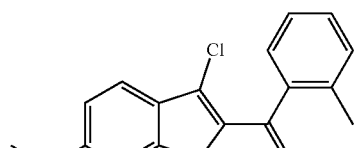 | (3-Chloro-6-methoxybenzo[b]thiophen-2-yl)(o-tolyl)methanone | ¹H NMR (400 MHz, CDCl₃) δ 7.80 (d, J = 9.0 Hz, 1H), 7.45-7.35 (m, 2H), 7.34-7.19 (m, 3H), 7.09 (dd, J = 9.0, 2.3 Hz, 1H), 3.91 (s, 3H), 2.39 (s, 3H). ¹³C NMR (100 MHz, CDCl₃) δ 191.06, 160.90, 141.81, 139.41, 136.21, 133.86, 131.59, 131.03, 130.72, 127.93, 126.44, 125.77, 125.32, 116.86, 104.45, 55.91, 19.70. |
| 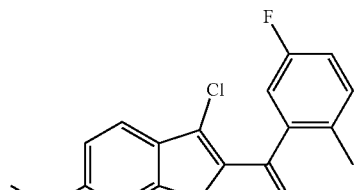 | (3-chloro-6-methoxybenzo[b]thiophen-2-yl)(5-fluoro-2-methylphenyl)methanone | ¹H NMR (400 MHz, CDCl₃) δ 7.81 (d, J = 9.0 Hz, 1H), 7.26-7.23 (m, 2H), 7.13-7.08 (m, 3H), 3.92 (s, 3H), 2.32 (s, 3H). ¹³C NMR (100 MHz, CDCl₃) δ 189.59, 161.17, 160.92 (d, J = 245.5 Hz), 142.07, 140.77 (d, J = 6.3 Hz), 133.30, 132.55 (d, J = 7.4 Hz), 131.64 (d, J = 3.5 Hz), 131.58, 127.03, 125.48, 117.45 (d, J = 21.0 Hz), 117.06, 114.61 (d, J = 23.0 Hz), 104.52, 55.95, 18.84. |
| 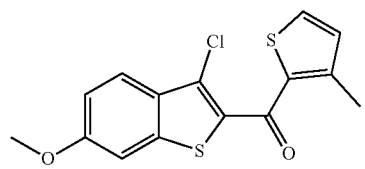 | (3-chloro-6-methoxybenzo[b]thiophen-2-yl)(3-methylthiophen-2-yl)methanone | ¹H NMR (400 MHz, CDCl₃) δ 7.82 (d, J = 8.9 Hz, 1H), 7.54 (d, J = 4.9 Hz, 1H), 7.26 (d, J = 2.2 Hz, 1H), 7.12 (dd, J = 8.9, 2.2 Hz, 1H), 6.99 (d, J = 4.9 Hz, 1H), 3.91 (s, 3H), 2.50 (s, 3H). ¹³C NMR (100 MHz, CDCl₃) δ 181.18, 160.26, 146.19, 140.41, 135.96, 132.23, 132.15, 131.81, 130.83, 124.63, 124.02, 116.64, 104.52, 55.89, 16.40. |
| 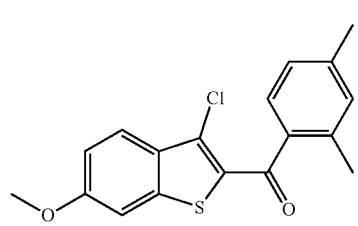 | (3-chloro-6-methoxybenzo[b]thiophen-2-yl)(2,4-dimethylphenyl)methanone | ¹H NMR (400 MHz, CDCl₃) δ 7.76 (d, J = 9.0 Hz, 1H), 7.33 (d, J = 7.7 Hz, 1H), 7.20 (d, J = 2.0 Hz, 1H), 7.10-7.00 (m, 3H), 3.87 (s, 3H), 2.37 (s, 6H). |

Scheme 2: Synthesis of 3-Chloro-6-methoxybenzo[b]thiophen-2-yl)(2-(trifluoromethyl)phenyl)methanone (I-4)

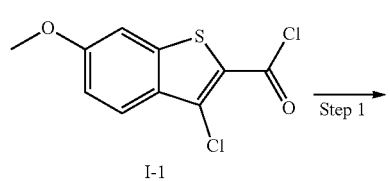

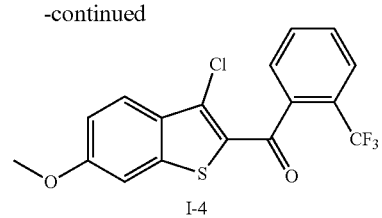

To a solution of 3-chloro-6-methoxybenzo[b]thiophene-2-carbonyl chloride (I-1, 1.04 g, 4 mmol) in THF under argon atmosphere was added a freshly prepared solution of (2-(trifluoromethyl)phenyl)magnesium bromide (5 mmol) drop-wise. The reaction mixture was stirred overnight and quenched by 1 N HCl/ice water. The solution was extracted with ethyl acetate and washed with brine. The organic extracts were combined, dried over anhydrous Na₂SO₄, concentrated in vacuum, and purified by flash chromatography (1%-15% ethyl acetate in hexane) to afford 350 mg of a white solid (19%). ¹H NMR (400 MHz, CDCl₃) δ 7.77 (t, J=8.3 Hz, 2H), 7.70-7.57 (m, 2H), 7.47 (d, J=6.4 Hz, 1H), 7.24 (s, 1H), 7.07 (dd, J=9.0, 1.9 Hz, 1H), 3.90 (s, 3H). ¹³C NMR (100 MHz, CDCl₃) δ 187.86, 161.27, 142.29, 138.58 (q, J=2.1 Hz), 133.23, 131.99, 131.49, 130.20, 127.88, 127.75, 127.69 (q, J=32.3 Hz), 126.89 (q, J=4.5 Hz), 125.49, 123.70 (q, J=274.0 Hz), 117.07, 104.41, 55.91. ¹⁹F NMR (400 MHz, CDCl₃) δ −58.46.

Intermediates shown below in Table 2 were synthesized by an analogous procedure to the synthesis of compound I-4 utilizing the appropriate Grignard reagent. The characterization of each intermediate is shown along with the name and structure.

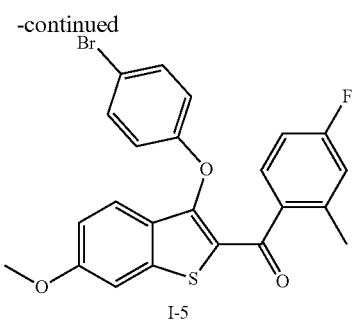

I-5

Cs₂CO₃ (1.52 g, 4.67 mmol) was added in one portion to a solution of compound I-3 (520 mg, 1.56 mmol) and 4-bromophenol in 5 mL DMF. The reaction mixture was raised to 50° C. and after stirring overnight, the reaction mixture was quenched with ice water, extracted with ethyl acetate, and washed with brine. The organic extracts were combined, dried over anhydrous Na₂SO₄, concentrated in vacuum, and purified by flash chromatography (1%-15%

TABLE 2

Compound structure and characterization of intermediates synthesized analogously to compound I-4

| Structure | Name | Characterization |
|---|---|---|
| 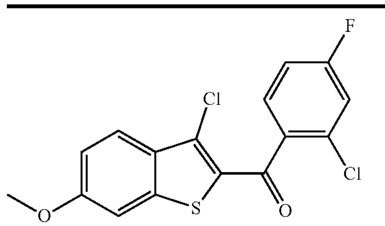 | (2-Chloro-4-fluorophenyl)(3-chloro-6-methoxybenzo[b]thiophen-2-yl)methanone | ¹H NMR (400 MHz, CDCl₃) δ 7.76 (d, J = 9.0 Hz, 1H), 7.43 (dd, J = 8.5, 5.9 Hz, 1H), 7.24-7.16 (m, 2H), 7.13-7.02 (m, 2H), 3.90 (s, 3H). ¹³C NMR (100 MHz, CDCl₃) δ 186.58, 163.57 (d, J = 253.9 Hz), 161.19, 142.19, 135.45 (d, J = 3.7 Hz), 133.24, 132.81 (d, J = 10.6 Hz), 131.39, 130.35 (d, J = 9.4 Hz), 127.28, 125.42, 117.63 (d, J = 24.9 Hz), 117.03, 114.63 (d, J = 21.6 Hz), 104.40, 55.87. |
| 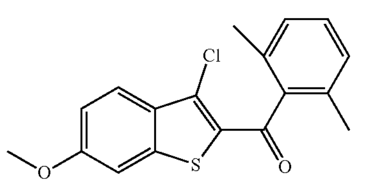 | (3-Chloro-6-methoxybenzo[b]thiophen-2-yl)(2,6-dimethylphenyl)methanone | ¹H NMR (400 MHz, CDCl₃) δ 7.79 (d, J = 9.0 Hz, 1H), 7.26-7.18 (m, 2H), 7.12-7.02 (m, 3H), 3.90 (s, 3H), 2.22 (s, 6H). ¹³C NMR (100 MHz, CDCl₃) δ 192.58, 161.14, 142.18, 140.22, 134.18, 131.75, 129.31, 127.84, 126.81, 125.55, 116.91, 104.53, 55.91, 19.31. |

Scheme 3: Synthesis of (3-(4-Bromophenoxy)-6-methoxybenzo[b]thiophen-2-yl)(4-fluoro-2-methylphenyl)methanone (I-5)

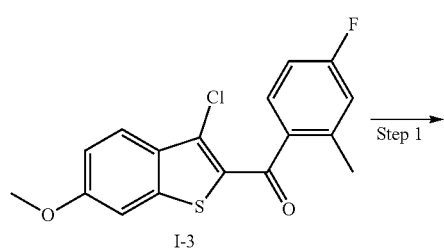

I-3 ethyl acetate in hexane) to afford 490 mg of compound I-5 as a white solid (67%). ¹H NMR (400 MHz, CDCl₃) δ 7.43 (d, J=8.9 Hz, 1H), 7.34-7.27 (m, 2H), 7.22-7.17 (m, 2H), 6.96 (dd, J=8.9, 2.2 Hz, 1H), 6.80-6.76 (m, 2H), 6.40-6.33 (m, 2H), 3.91 (s, 3H), 2.16 (s, 3H). ¹³C NMR (100 MHz, CDCl₃) δ 189.34, 163.72 (d, J=250.2 Hz), 161.07, 157.45, 148.25, 142.21, 139.63 (d, J=8.6 Hz), 135.29 (d, J=3.1 Hz), 132.38, 130.24 (d, J=9.2 Hz), 126.82, 127.48, 124.57, 117.45 (d, J=21.4 Hz), 116.74, 116.55, 115.09, 112.19 (d, J=21.7 Hz), 105.19, 55.89, 19.53 (d, J=1.3 Hz).

Intermediates shown below in Table 3 were synthesized by an analogous procedure to the synthesis of compound I-5 utilizing the appropriate starting materials. The characterization of each intermediate is shown along with the name and structure.

TABLE 3

Compound structure and characterization of intermediates synthesized analogously to compound I-5

| Structure | Name | NMR Data |
|---|---|---|
| 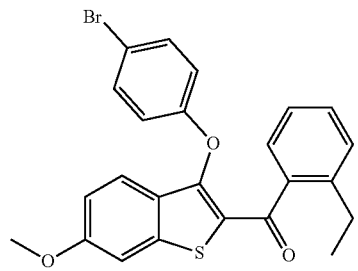 [SMILES: CCc1ccccc1C(=O)c1sc2cc(OC)ccc2c1Oc1ccc(Br)cc1] | (3-(4-Bromophenoxy)-6-methoxybenzo[b]thiophen-2-yl)(4-methoxyphenyl)methanone | $^1$H NMR (400 MHz, CDCl$_3$) δ 7.76 (d, J = 8.9 Hz, 2H), 7.47 (d, J = 8.9 Hz, 1H), 7.28 (d, J = 2.1 Hz, 1H), 7.21 (d, J = 9.0 Hz, 2H), 6.98 (dd, J = 8.9, 2.2 Hz, 1H), 6.86 (d, J = 8.9 Hz, 2H), 6.54 (d, J = 9.0 Hz, 2H), 3.91 (s, 3H), 3.86 (s, 3H). $^{13}$C NMR (100 MHz, CDCl$_3$) $^{13}$C NMR (100 MHz, CDCl$_3$) δ 187.33, 163.49, 160.43, 157.45, 146.58, 141.29, 132.47, 131.84, 130.92, 126.71, 125.99, 124.18, 117.46, 116.23, 115.05, 113.43, 105.08, 55.87, 55.64. |
| 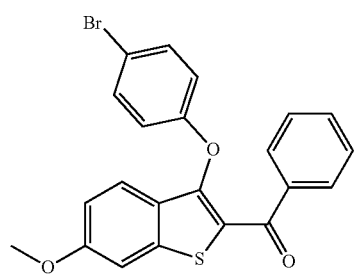 [SMILES: COc1ccc2c(Oc3ccc(Br)cc3)c(C(=O)c3ccccc3)sc2c1] | (3-(4-Bromophenoxy)-6-methoxybenzo[b]thiophen-2-yl)(2-ethylphenyl)methanone | $^1$H NMR (400 MHz, CDCl$_3$) δ 7.39 (d, J = 8.9 Hz, 1H), 7.29-7.24 (m, 3H), 7.17-7.13 (m, 3H), 7.07 (t, J = 7.5 Hz, 1H), 6.94 (dd, J = 8.9, 2.2 Hz, 1H), 6.35-6.29 (m, 2H), 3.91 (s, 3H), 2.50 (q, J = 7.5 Hz, 2H), 1.06 (t, J = 7.6 Hz, 3H). $^{13}$C NMR (100 MHz, CDCl$_3$) δ 190.68, 160.98, 157.30, 148.30, 142.19, 142.15, 138.95, 132.27, 130.35, 128.91, 128.06, 127.55, 126.90, 125.21, 124.66, 116.93, 116.46, 114.91, 105.22, 55.89, 26.21, 15.62. |
| 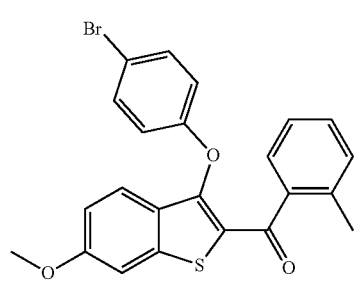 | (3-(4-Bromophenoxy)-6-methoxybenzo[b]thiophen-2-yl)(phenyl)methanone | $^1$H NMR (400 MHz, CDCl$_3$) δ 7.72-7.65 (m, 2H), 7.52-7.44 (m, 2H), 7.34 (t, J = 7.7 Hz, 2H), 7.28 (d, J = 2.1 Hz, 1H), 7.21-7.15 (m, 2H), 6.97 (dd, J = 8.9, 2.2 Hz, 1H), 6.49-6.43 (m, 2H), 3.92 (s, 3H). $^{13}$C NMR (100 MHz, CDCl$_3$) δ 188.95, 160.72, 157.40, 147.59, 141.76, 138.49, 132.47, 132.40, 129.02, 128.09, 126.72, 125.92, 124.44, 117.33, 116.40, 115.07, 105.10, 55.88. |
| 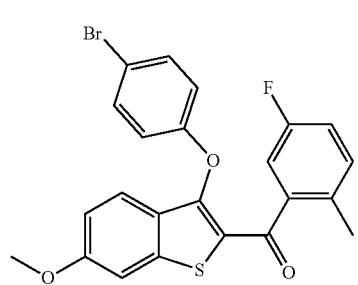 | (3-(4-Bromophenoxy)-6-methoxybenzo[b]thiophen-2-yl)(o-tolyl)methanone | $^1$H NMR (400 MHz, CDCl$_3$) δ 7.42 (d, J = 8.9 Hz, 1H), 7.29-7.20 (m, 3H), 7.18-7.12 (m, 2H), 7.11-7.04 (m, 2H), 6.95 (dd, J = 8.9, 2.2 Hz, 1H), 6.37-6.26 (m, 2H), 3.91 (s, 3H), 2.16 (s, 3H). $^{13}$C NMR (100 MHz, CDCl$_3$) δ 190.66, 160.99, 157.45, 148.38, 142.20, 139.30, 135.92, 132.27, 130.63, 130.28, 127.74, 127.63, 126.92, 125.25, 124.60, 116.86, 116.48, 114.92, 105.20, 55.89, 19.36. |
| 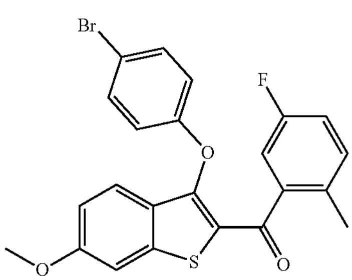 | (3-(4-Bromophenoxy)-6-methoxybenzo[b]thiophen-2-yl)(5-fluoro-2-methylphenyl)methanone | $^1$H NMR (400 MHz, CDCl$_3$) δ 7.41 (d, J = 8.9 Hz, 1H), 7.28 (d, J = 2.1 Hz, 1H), 7.19 (d, J = 9.0 Hz, 2H), 7.04-6.91 (m, 4H), 6.38 (d, J = 9.0 Hz, 2H), 3.91 (s, 3H), 2.11 (s, 3H). $^{13}$C NMR (100 MHz, CDCl$_3$) δ 189.11, 161.19, 160.60 (d, J = 245.3 Hz), 157.28, 148.76, 142.47, 140.60 (d, J = 6.3 Hz), 132.42, 132.06 (d, J = 7.4 Hz), 131.36 (d, J = 3.5 Hz), 127.15, 126.70, 124.75, 116.90 (d, J = 20.9 Hz), 116.76, 116.64, 115.15, 114.34 (d, J = 23.0 Hz), 105.22, 55.90, 18.56. |

TABLE 3-continued

Compound structure and characterization of intermediates synthesized analogously to compound I-5

| Structure | Name | Characterization |
|---|---|---|
| 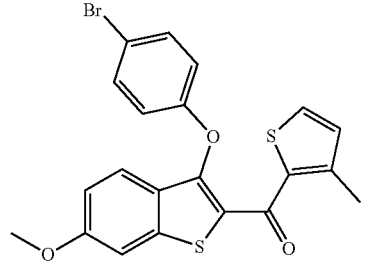 | (3-(4-Bromophenoxy)-6-methoxybenzo[b]thiophen-2-yl)(3-methylthiophen-2-yl)methanone | $^1$H NMR (400 MHz, CDCl$_3$) δ 7.52 (d, J = 8.9 Hz, 1H), 7.42 (d, J = 4.9 Hz, 1H), 7.28-7.23 (m, 3H), 6.99 (dd, J = 8.9, 2.2 Hz, 1H), 6.87 (d, J = 4.9 Hz, 1H), 6.67-6.59 (m, 2H), 3.91 (s, 3H), 2.34 (s, 3H). $^{13}$C NMR (101 MHz, DMSO) δ 181.10, 160.50, 157.62, 147.31, 145.02, 140.99, 135.76, 132.50, 131.63, 130.84, 126.58, 125.44, 124.19, 117.62, 116.31, 115.25, 104.96, 55.87, 15.94. |
| 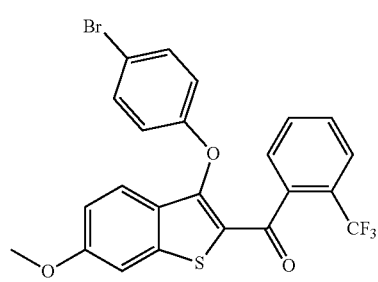 [SMILES: COc1ccc2c(Oc3ccc(Br)cc3)c(C(=O)c3ccccc3C(F)(F)F)sc2c1] | (3-(4-Bromophenoxy)-6-methoxybenzo[b]thiophen-2-yl)(2-(trifluoromethyl)phenyl)methanone | $^1$H NMR (400 MHz, CDCl$_3$) δ 7.59 (d, J = 7.7 Hz, 1H), 7.43 (t, J = 7.5 Hz, 1H), 7.37 (t, J = 7.3 Hz, 1H), 7.33-7.28 (m, 1H), 7.27-7.21 (m, 2H), 7.18 (d, J = 8.9 Hz, 2H), 6.89 (dd, J = 8.9, 2.2 Hz, 1H), 6.33 (d, J = 8.9 Hz, 2H), 3.89 (s, 3H). |
| 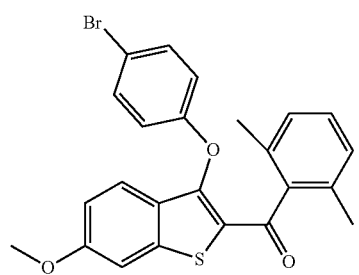 | (3-(4-Bromophenoxy)-6-methoxybenzo[b]thiophen-2-yl)(2,6-dimethylphenyl)methanone | $^1$H NMR (400 MHz, CDCl$_3$) δ 7.34 (d, J = 8.9 Hz, 1H), 7.28 (d, J = 2.1 Hz, 1H), 7.17 (d, J = 8.9 Hz, 2H), 7.04 (t, J = 7.6 Hz, 1H), 6.92 (dd, J = 8.9, 2.2 Hz, 1H), 6.86 (d, J = 7.7 Hz, 2H), 6.34 (d, J = 8.9 Hz, 2H), 3.88 (s, 3H), 2.11 (s, 6H). $^{13}$C NMR (100 MHz, CDCl$_3$) δ 192.08, 160.94, 156.72, 148.28, 142.22, 140.16, 133.71, 131.95, 128.73, 128.49, 127.35, 126.59, 124.67, 116.52, 116.40, 114.74, 105.22, 55.75, 19.18. |
| 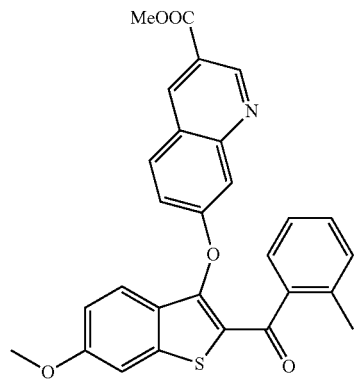 | Methyl 7-((6-methoxy-2-(2-methylbenzoyl)benzo[b]thiophen-3-yl)oxy)quinoline-3-carboxylate | $^1$H NMR (400 MHz, CDCl$_3$) δ 9.29 (d, J = 1.7 Hz, 1H), 8.71 (s, 1H), 7.64 (d, J = 9.0 Hz, 1H), 7.45 (d, J = 8.9 Hz, 1H), 7.30 (d, J = 1.8 Hz, 1H), 7.25 (d, J = 7.3 Hz, 1H), 7.16 (t, J = 7.3 Hz, 1H), 7.08 (d, J = 1.9 Hz, 1H), 6.99-6.88 (m, 3H), 6.83 (dd, J = 8.9, 2.3 Hz, 1H), 3.98 (s, 3H), 3.91 (s, 3H), 2.04 (s, 3H). $^{13}$C NMR (100 MHz, CDCl$_3$) δ 190.40, 165.93, 161.07, 160.98, 150.88, 150.81, 147.66, 142.34, 139.30, 138.37, 135.65, 130.48, 130.41, 130.14, 128.07, 127.33, 126.64, 125.14, 124.40, 122.83, 121.83, 118.87, 116.73, 111.31, 105.15, 55.89, 52.53, 19.22. |
| 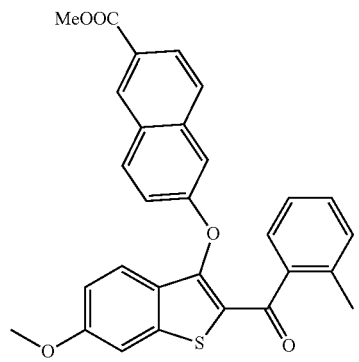 | Methyl 6-((6-methoxy-2-(2-methylbenzoyl)benzo[b]thiophen-3-yl)oxy)-2-naphthoate | $^1$H NMR (400 MHz, CDCl$_3$) δ 8.48 (s, 1H), 7.96 (dd, J = 8.6, 1.5 Hz, 1H), 7.64 (d, J = 9.0 Hz, 1H), 7.50 (d, J = 8.7 Hz, 1H), 7.47 (d, J = 8.9 Hz, 1H), 7.32-7.27 (m, 2H), 7.16 (t, J = 7.5 Hz, 1H), 6.98 (t, J = 7.5 Hz, 1H), 6.95-6.86 (m, 2H), 6.77 (d, J = 2.2 Hz, 1H), 6.73 (dd, J = 8.9, 2.5 Hz, 1H), 3.93 (s, 3H), 3.86 (s, 3H), 1.99 (s, 3H). $^{13}$C NMR (100 MHz, CDCl$_3$) δ 190.43, 167.05, 160.88, 158.00, 148.20, 142.08, 139.06, 136.21, 135.72, 131.02, 130.70, 130.36, 130.05, 128.52, 127.67, 127.47, 127.05, 126.85, 126.09, 126.02, 125.04, 124.43, 117.70, 116.38, 109.49, 105.09, 55.69, 52.11, 19.06. |

TABLE 3-continued

Compound structure and characterization of intermediates synthesized analogously to compound I-5

| Structure | Name | Characterization |
|---|---|---|
| 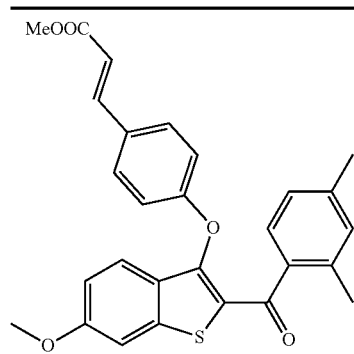 | Methyl (E)-3-(4-((2-(2,4-dimethylbenzoyl)-6-methoxybenzo[b]thiophen-3-yl)oxy)phenyl)acrylate | $^1$H NMR (400 MHz, CDCl$_3$) δ 7.57 (d, J = 16.0 Hz, 1H), 7.46 (d, J = 8.9 Hz, 1H), 7.28 (d, J = 2.1 Hz, 1H), 7.23 (t, J = 8.9 Hz, 3H), 6.96 (dd, J = 8.9, 2.2 Hz, 1H), 6.85 (d, J = 11.2 Hz, 2H), 6.47 (d, J = 8.8 Hz, 2H), 6.27 (d, J = 16.0 Hz, 1H), 3.91 (s, 3H), 3.79 (s, 3H), 2.29 (s, 3H), 2.09 (s, 3H). $^{13}$C NMR (100 MHz, CDCl$_3$) δ 190.48, 167.65, 160.87, 160.01, 147.81, 144.09, 141.92, 140.64, 136.30, 136.22, 131.40, 129.33, 128.91, 128.29, 127.79, 127.05, 125.79, 124.43, 116.48, 116.43, 115.58, 105.11, 55.87, 51.79, 21.47, 19.38. |
| 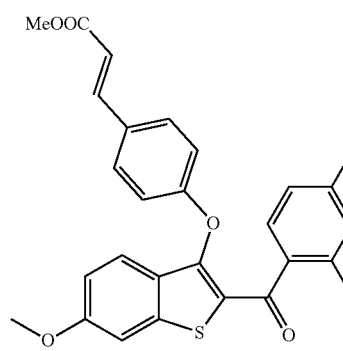 | Methyl (E)-3-(4-((2-(2-chloro-4-fluorobenzoyl)-6-methoxybenzo[b]thiophen-3-yl)oxy)phenyl)acrylate | $^1$H NMR (400 MHz, CDCl$_3$) δ 7.58 (d, J = 16.0 Hz, 1H), 7.37 (d, J = 9.0 Hz, 1H), 7.28 (t, J = 8.8 Hz, 3H), 7.20 (dd, J = 8.5, 5.9 Hz, 1H), 7.00 (dd, J = 8.6, 2.3 Hz, 1H), 6.93 (dd, J = 9.0, 2.2 Hz, 1H), 6.81 (td, J = 8.3, 2.4 Hz, 1H), 6.55 (d, J = 8.7 Hz, 2H), 6.29 (d, J = 16.0 Hz, 1H), 3.91 (s, 3H), 3.79 (s, 3H). $^{13}$C NMR (100 MHz, CDCl$_3$) δ 186.10, 167.53, 163.16 (d, J = 253.1 Hz), 161.27, 159.30, 148.85, 143.81, 142.73, 135.48 (d, J = 3.7 Hz), 132.49 (d, J = 10.6 Hz), 129.79 (d, J = 9.3 Hz), 129.56, 129.36, 127.18, 126.36, 124.83, 117.18 (d, J = 24.9 Hz), 116.91, 116.72, 115.45, 113.83 (d, J = 21.6 Hz), 105.22, 55.91, 51.82. |

Scheme 4: Synthesis of (3-(4-Bromophenoxy)-6-hydroxybenzo[b]thiophen-2-yl)(4-fluoro-2-methylphenyl)methanone (I-6)

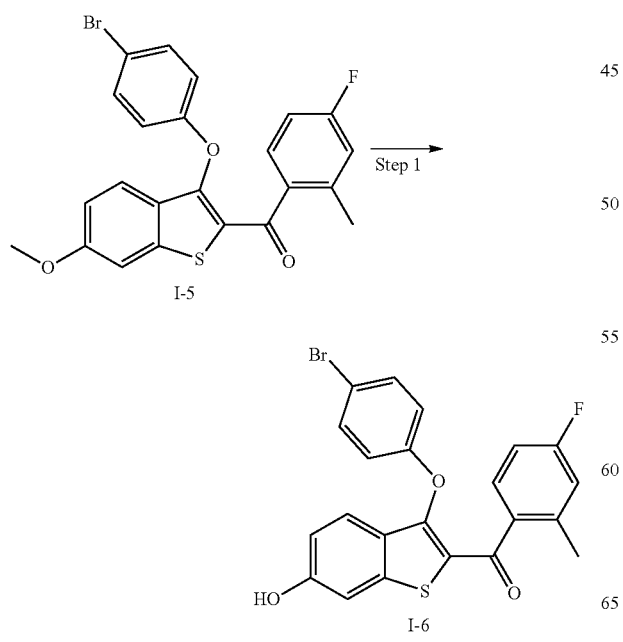

Compound I-5 (480 mg, 1 mmol) was dissolved in 10 mL of anhydrous dichloromethane at room temperature and BF$_3$.SMe$_2$ (1.2 ml, 5 mmol) was added dropwise to this solution. The reaction mixture was stirred until starting material, as monitored by TLC, was consumed. The reaction was then quenched with saturated NaHCO$_3$/ice water, extracted with ethyl acetate, and washed with brine. The organic extracts were combined, dried over anhydrous Na$_2$SO$_4$, concentrated in vacuum, and purified by flash chromatography (5%-60% ethyl acetate in hexane) to afford 390 mg of compound I-6 as a white powder (85%). $^1$H NMR (400 MHz, MeOD) δ 7.38 (d, J=8.8 Hz, 1H), 7.35-7.28 (m, 1H), 7.28-7.20 (m, 3H), 6.90 (dd, J=8.8, 2.1 Hz, 1H), 6.87-6.80 (m, 2H), 6.46-6.38 (m, 2H), 2.13 (s, 3H).

Intermediates shown below in Table 4 were synthesized by an analogous procedure to the synthesis of compound I-6 utilizing the appropriate starting materials. The characterization of each intermediate is shown along with the name and structure.

TABLE 4

Compound structure and characterization of intermediates synthesized analogously to compound I-6

| Structure | Name | Characterization |
|---|---|---|
| | (3-(4-Bromophenoxy)-6-hydroxybenzo[b]thiophen-2-yl) (4-hydroxyphenyl)methanone | $^1$H NMR (400 MHz, Acetone) δ 7.71 (d, J = 8.7 Hz, 2H), 7.47 (d, J = 8.7 Hz, 1H), 7.41 (d, J = 2.0 Hz, 1H), 7.35 (d, J = 9.0 Hz, 2H), 7.02 (dd, J = 8.8, 2.1 Hz, 1H), 6.86 (d, J = 8.7 Hz, 2H), 6.68 (d, J = 9.0 Hz, 2H). |
| | (3-(4-Bromophenoxy)-6-hydroxybenzo[b]thiophen-2-yl) (2-ethylphenyl)methanone | $^1$H NMR (400 MHz, Acetone) δ 9.25 (s, 1H), 7.44-7.38 (m, 2H), 7.35-7.26 (m, 4H), 7.19 (d, J = 7.5 Hz, 1H), 7.12 (t, J = 7.5 Hz, 1H), 6.99 (dd, J = 8.8, 2.2 Hz, 1H), 6.52-6.44 (m, 2H), 2.49 (q, J = 7.5 Hz, 2H), 1.04 (t, J = 7.6 Hz, 3H). $^{13}$C NMR (101 MHz, CDCl$_3$) δ 190.58, 159.88, 158.26, 149.03, 142.77, 142.50, 140.15, 133.10, 130.97, 129.63, 128.13, 128.05, 126.79, 126.01, 125.59, 118.04, 117.20, 115.18, 108.98, 26.72, 15.95. |
| | (3-(4-Bromophenoxy)-6-hydroxybenzo[b]thiophen-2-yl) (phenyl)methanone | $^1$H NMR (400 MHz, MeOD) δ 7.62 (d, J = 7.2 Hz, 2H), 7.51 (t, J = 7.5 Hz, 1H), 7.44-7.32 (m, 3H), 7.25-7.21 (m, 3H), 6.91 (dd, J = 8.8, 2.1 Hz, 1H), 6.49 (d, J = 9.0 Hz, 2H). $^{13}$C NMR (101 MHz, MeOD) δ 190.76, 160.50, 158.77, 149.54, 143.24, 139.95, 133.47, 133.38, 129.69, 129.14, 126.80, 125.81, 125.53, 118.42, 117.39, 115.88, 108.74. |
| | (3-(4-Bromophenoxy)-6-hydroxybenzo[b]thiophen-2-yl) (o-tolyl)methanone | $^1$H NMR (400 MHz, MeOD) δ 7.36 (d, J = 8.8 Hz, 1H), 7.30-7.17 (m, 5H), 7.09 (t, J = 7.4 Hz, 2H), 6.89 (dd, J = 8.8, 2.1 Hz, 1H), 6.41-6.32 (m, 2H), 2.11 (s, 3H). $^{13}$C NMR (100 MHz, MeOD) δ 192.45, 160.86, 158.79, 150.45, 143.73, 140.77, 136.58, 133.33, 131.53, 131.27, 128.38, 127.60, 126.95, 126.34, 125.74, 117.99, 117.49, 115.77, 108.88, 19.29. |
| | (3-(4-Bromophenoxy)-6-hydroxybenzo[b]thiophen-2-yl) (5-fluoro-2-methylphenyl)methanone | $^1$H NMR (400 MHz, Acetone) δ 7.44-7.41 (m, 2H), 7.33 (d, J = 9.0 Hz, 2H), 7.18-7.13 (m, 1H), 7.09 (dd, J = 8.9, 2.7 Hz, 1H), 7.05-6.99 (m, 2H), 6.54 (d, J = 9.0 Hz, 2H), 2.11 (s, 3H). $^{13}$C NMR (101 MHz, CDCl$_3$) δ 189.08, 161.39 (d, J = 243.4 Hz), 160.11, 158.23, 149.48, 143.09, 142.07 (d, J = 6.4 Hz), 133.24, 132.96 (d, J = 7.6 Hz), 131.83 (d, J = 3.4 Hz), 127.43, 126.60, 125.72, 117.91, 117.34, 117.29 (d, J = 21.3 Hz), 115.39, 114.60 (d, J = 23.2 Hz), 109.04, 18.45. |

TABLE 4-continued

Compound structure and characterization of intermediates synthesized analogously to compound I-6

| Structure | Name | Characterization |
|---|---|---|
| 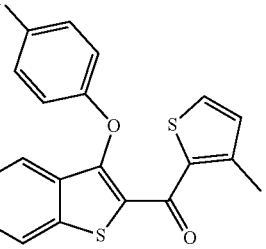 | (3-(4-Bromophenoxy)-6-hydroxybenzo[b]thiophen-2-yl)(3-methylthiophen-2-yl)Methanone | $^1$H NMR (400 MHz, Acetone-d6) δ 9.19 (s, 1H), 7.65 (d, J = 4.9 Hz, 1H), 7.54 (d, J = 8.8 Hz, 1H), 7.42 (d, J = 2.1 Hz, 1H), 7.39-7.32 (m, 2H), 7.04 (dd, J = 8.8, 2.1 Hz, 1H), 6.97 (d, J = 4.9 Hz, 1H), 6.74-6.65 (m, 2H), 2.29 (s, 3H). $^{13}$C NMR (100 MHz, Acetone-d6) δ 181.07, 159.40, 158.68, 147.89, 144.79, 141.57, 136.57, 133.26, 132.38, 131.63, 126.53, 125.63, 124.95, 118.55, 117.13, 115.47, 108.7, 15.70. |
| 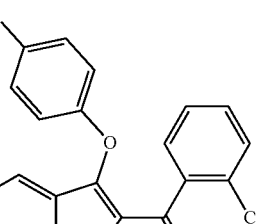 | (3-(4-Bromophenoxy)-6-hydroxybenzo[b]thiophen-2-yl) (2-(trifluoromethyl)phenyl)Methanone | $^1$H NMR (400 MHz, MeOD) δ 7.58 (d, J = 7.8 Hz, 1H), 7.43 (t, J = 7.5 Hz, 1H), 7.36 (t, J = 7.3 Hz, 1H), 7.31 (d, J = 7.2 Hz, 1H), 7.23 (d, J = 2.0 Hz, 1H), 7.19-7.09 (m, 3H), 6.80 (dd, J = 8.9, 2.1 Hz, 1H), 6.31 (d, J = 9.0 Hz, 2H). |
| 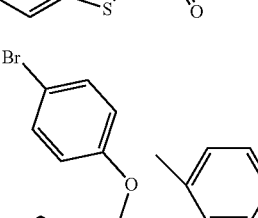 | (3-(4-Bromophenoxy)-6-hydroxybenzo[b]thiophen-2-yl)(2,6-dimethylphenyl)Methanone | $^1$H NMR (400 MHz, Acetone) δ 9.29 (s, 1H), 7.43 (d, J = 2.1 Hz, 1H), 7.35 (d, J = 8.8 Hz, 1H), 7.29 (d, J = 9.0 Hz, 2H), 7.06 (t, J = 7.6 Hz, 1H), 6.98 (dd, J = 8.8, 2.1 Hz, 1H), 6.90 (d, J = 7.5 Hz, 2H), 6.46 (d, J = 8.9 Hz, 2H), 2.08 (s, 6H). $^{13}$C NMR (100 MHz, Acetone) δ 191.96, 159.98, 157.87, 149.06, 142.90, 141.45, 134.37, 132.90, 129.46, 128.64, 128.13, 126.65, 125.75, 117.72, 117.26, 115.12, 109.12, 19.29. |

Scheme 5: Synthesis of Methyl (E)-3-(4-((2-(4-fluoro-2-methylbenzoyl)-6-hydroxybenzo[b]thiophen-3-yl)oxy)phenyl)acrylate (I-7)

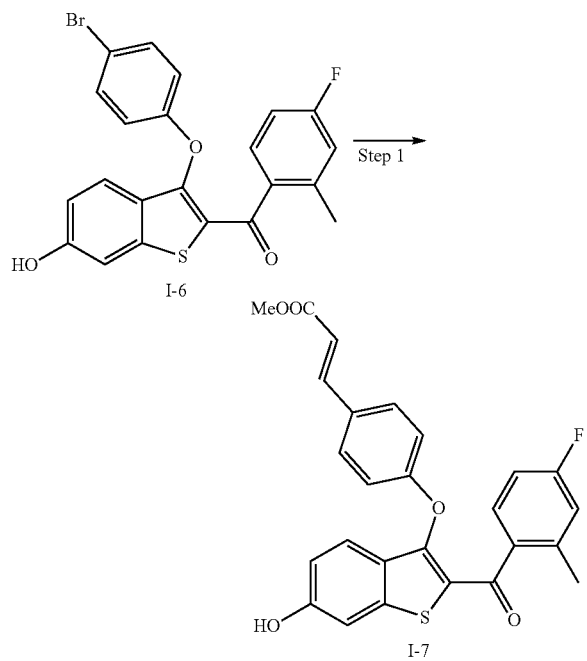

In a sealed tube, compound I-6 (200 mg, 0.46 mmol), methyl acrylate (240 mg, 2.76 mmol), and Pd(PPh$_3$)$_2$C$_{12}$ were suspended in DMF (2 ml) and triethylamine (235 mg, 2.3 mmol). The reaction was heated at 110° C. for 6 hours. The reaction mixture was quenched by water and extracted with ethyl acetate. The organic layers was collected and purified by flash chromatography (5%-60% ethyl acetate in hexane) to afford 170 mg of compound I-7 as a white powder (85%). $^1$H NMR (400 MHz, MeOD) δ 7.57 (d, J=16.0 Hz, 1H), 7.40-7.36 (m, 3H), 7.32 (dd, J=8.8, 6.0 Hz, 1H), 7.27 (d, J=1.8 Hz, 1H), 6.89 (m J=8.9, 1.9 Hz, 1H), 6.83-6.78 (m, 2H), 6.52 (d, J=8.7 Hz, 2H), 6.37 (d, J=16.0 Hz, 1H), 3.76 (s, 3H), 2.10 (s, 3H). $^{13}$C NMR (100 MHz, MeOD) δ 191.09, 169.17, 164.95 (d, J=248.7 Hz), 161.19, 160.91, 150.13, 145.22, 143.71, 140.41 (d, J=8.6 Hz), 136.86 (d, J=3.0 Hz), 131.11 (d, J=9.2 Hz), 130.77, 130.47, 127.59, 126.92, 125.70, 118.13 (d, J=21.8 Hz), 117.55, 117.48, 116.47, 113.11 (d, J=21.9 Hz), 108.89, 52.09, 19.41.

Intermediates shown below in Table 5 were synthesized by an analogous procedure to the synthesis of compound I-7 utilizing the appropriate starting materials. The characterization of each intermediate is shown along with the name and structure.

TABLE 5

Compound structure and characterization of intermediates synthesized analogously to compound I-7

| Structure | Name | NMR |
|---|---|---|
| 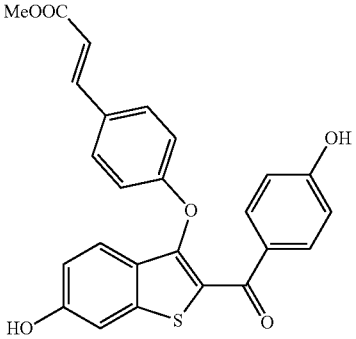 | Methyl (E)-3-(4-((6-hydroxy-2-(4-hydroxybenzoyl)benzo[b]thiophen-3-yl)oxy)phenyl)acrylate | $^1$H NMR (400 MHz, MeOD) δ 7.61 (d, J = 8.7 Hz, 2H), 7.55 (d, J = 16.0 Hz, 1H), 7.42 (d, J = 8.8 Hz, 1H), 7.39 (d, J = 8.8 Hz, 2H), 7.26 (d, J = 2.0 Hz, 1H), 6.91 (dd, J = 8.8, 2.1 Hz, 1H), 6.74 (d, J = 8.7 Hz, 2H), 6.66 (d, J = 8.8 Hz, 2H), 6.35 (d, J = 16.0 Hz, 1H), 3.74 (s, 3H). |
| 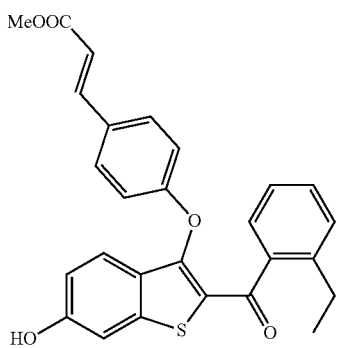 [SMILES: CCc1ccccc1C(=O)c1sc2cc(O)ccc2c1Oc1ccc(/C=C/C(=O)OC)cc1] | Methyl (E)-3-(4-((2-(2-ethylbenzoyl)-6-hydroxybenzo[b]thiophen-3-yl)oxy)phenyl)acrylate | $^1$H NMR (400 MHz, MeOD) δ 7.57 (d, J = 16.0 Hz, 1H), 7.40-7.20 (m, 6H), 7.14 (d, J = 7.7 Hz, 1H), 7.06 (t, J = 7.5 Hz, 1H), 6.88 (dd, J = 8.8, 2.1 Hz, 1H), 6.47 (d, J = 8.8 Hz, 2H), 6.36 (d, J = 16.0 Hz, 1H), 3.76 (s, 3H), 2.46 (q, J = 7.5 Hz, 2H), 1.02 (t, J = 7.6 Hz, 3H). $^{13}$C NMR (101 MHz, CDCl$_3$) δ 192.46, 169.17, 161.00, 160.81, 150.20, 145.31, 143.66, 142.87, 140.35, 131.30, 130.70, 130.29, 129.89, 128.29, 127.97, 126.89, 126.30, 125.79, 117.47, 117.31, 116.67, 108.90, 52.09, 27.10, 15.96. |
| 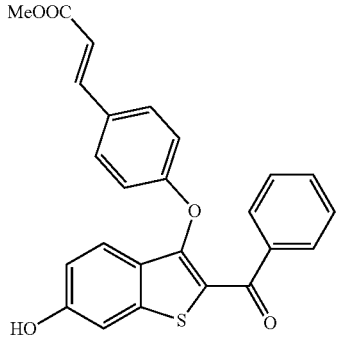 [SMILES: COC(=O)/C=C/c1ccc(Oc2c(C(=O)c3ccccc3)sc3cc(O)ccc23)cc1] | Methyl (E)-3-(4-((2-benzoyl-6-hydroxybenzo[b]thiophen-3-yl)oxy)phenyl)acrylate | $^1$H NMR (400 MHz, DMSO) δ 10.39 (s, 1H), 7.65 (d, J = 7.9 Hz, 2H), 7.56-7.52 (m, 4H), 7.39-7.34 (m, 4H), 6.93 (d, J = 8.8 Hz, 1H), 6.66 (d, J = 8.5 Hz, 2H), 6.47 (d, J = 16.1 Hz, 1H), 3.69 (s, 3H). $^{13}$C NMR (101 MHz, DMSO) δ 187.95, 166.69, 159.08, 158.90, 147.19, 143.62, 141.00, 138.11, 132.27, 130.10, 128.67, 128.32, 128.03, 124.63, 124.32, 124.29, 116.55, 116.51, 115.66, 108.03, 51.37. |
| 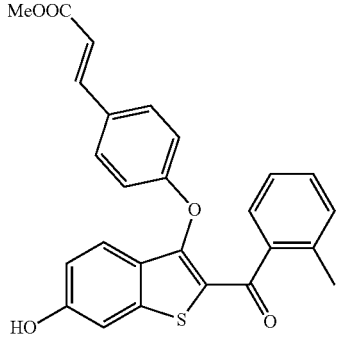 [SMILES: COC(=O)/C=C/c1ccc(Oc2c(C(=O)c3ccccc3C)sc3cc(O)ccc23)cc1] | Methyl (E)-3-(4-((6-hydroxy-2-(2-methylbenzoyl)benzo[b]thiophen-3-yl)oxy)phenyl)acrylate | $^1$H NMR (400 MHz, MeOD) δ 7.56 (d, J = 16.0 Hz, 1H), 7.35 (d, J = 8.6 Hz, 3H), 7.28-7.21 (m, 3H), 7.10-7.01 (m, 2H), 6.88 (dd, J = 8.8, 2.1 Hz, 1H), 6.46 (d, J = 8.7 Hz, 2H), 6.35 (d, J = 16.0 Hz, 1H), 3.76 (s, 3H), 2.09 (s, 3H). $^{13}$C NMR (100 MHz, MeOD) δ 192.43, 169.18, 161.17, 160.84, 150.28, 145.31, 143.69, 140.72, 136.56, 131.51, 131.25, 130.70, 130.31, 128.36, 127.69, 126.95, 126.32, 125.73, 117.49, 117.33, 116.58, 108.90, 52.09, 19.31. |

TABLE 5-continued

Compound structure and characterization of intermediates synthesized analogously to compound I-7

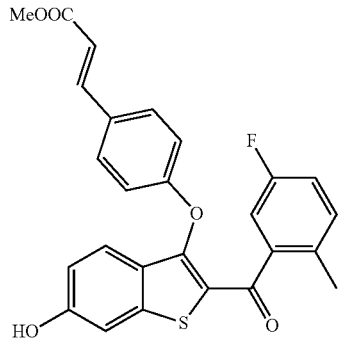 [SMILES: COC(=O)/C=C/c1ccc(Oc2c(C(=O)c3cc(F)ccc3C)sc3cc(O)ccc23)cc1]

Methyl (E)-3-(4-((2-(5-fluoro-2-methylbenzoyl)-6-hydroxybenzo[b]thiophen-3-yl)oxy)phenyl)acrylate ¹H NMR (400 MHz, MeOD) δ 7.55 (d, J = 16.0 Hz, 1H), 7.38-7.31 (m, 3H), 7.26 (d, J = 2.1 Hz, 1H), 7.09-7.00 (m, 1H), 6.99-6.92 (m, 2H), 6.87 (dd, J = 8.9, 2.1 Hz, 1H), 6.50 (d, J = 8.7 Hz, 2H), 6.35 (d, J = 16.0 Hz, 1H), 3.75 (s, 3H), 2.06 (s, 3H). ¹³C NMR (100 MHz, MeOD) δ 190.64, 169.15, 161.89 (d, J = 244.5 Hz), 161.01, 160.96, 150.54, 145.21, 143.94, 142.19 (d, J = 6.4 Hz), 133.17 (d, J = 7.5 Hz), 132.14 (d, J = 3.4 Hz), 130.80, 130.47, 127.31, 126.75, 125.87, 117.62 (d, J = 21.3 Hz), 117.60, 117.45, 116.49, 114.83 (d, J = 23.3 Hz), 108.94, 52.09, 18.49.

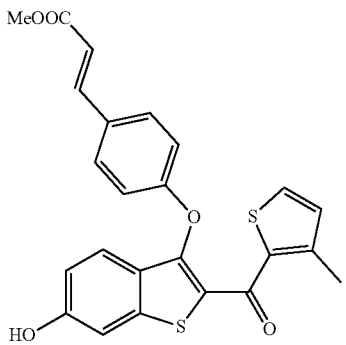 [SMILES: COC(=O)/C=C/c1ccc(Oc2c(C(=O)c3sccc3C)sc3cc(O)ccc23)cc1]

Methyl (E)-3-(4-((6-hydroxy-2-(3-methylthiophene-2-carbonyl)benzo[b]thiophen-3-yl)oxy)phenyl)acrylate ¹H NMR (400 MHz, MeOD) δ 7.61-7.55 (m, 2H), 7.50 (d, J = 8.8 Hz, 1H), 7.42 (d, J = 8.7 Hz, 2H), 7.28 (d, J = 2.1 Hz, 1H), 6.98-6.87 (m, 2H), 6.71 (d, J = 8.7 Hz, 2H), 6.38 (d, J = 16.0 Hz, 1H), 3.77 (s, 3H), 2.24 (s, 3H). ¹³C NMR (100 MHz, MeOD) δ 182.78, 169.15, 161.50, 160.27, 148.90, 145.52, 145.28, 142.40, 136.89, 132.55, 132.19, 130.85, 130.50, 126.82, 125.53, 125.13, 117.39, 117.09, 108.64, 52.09, 15.67.

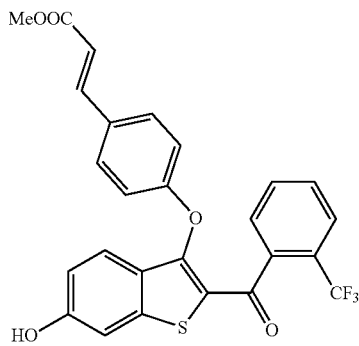 [SMILES: COC(=O)/C=C/c1ccc(Oc2c(C(=O)c3ccccc3C(F)(F)F)sc3cc(O)ccc23)cc1]

Methyl (E)-3-(4-((6-hydroxy-2-(2-(trifluoromethyl)benzoyl)benzo[b]thiophen-3-yl)oxy)phenyl)acrylate ¹H NMR (400 MHz, MeOD) δ 7.58 (d, J = 7.8 Hz, 1H), 7.52 (d, J = 16.0 Hz, 1H), 7.43 (t, J = 7.3 Hz, 1H), 7.38-7.21 (m, 5H), 7.17 (d, J = 8.8 Hz, 1H), 6.80 (dd, J = 8.8, 2.0 Hz, 1H), 6.42 (d, J = 8.7 Hz, 2H), 6.30 (d, J = 16.0 Hz, 1H), 3.71 (s, 3H). ¹³C NMR (100 MHz, MeOD) δ 188.88, 169.00, 160.87, 160.11, 150.85, 145.06, 143.97, 139.62 (q, J = 1.9 Hz), 132.62, 130.84, 130.65, 130.39, 128.51, 127.81 (q, J = 32.0 Hz), 127.29, 127.26 (q, J = 4.5 Hz), 126.13, 126.02, 125.02 (q, J = 273.4 Hz), 117.48, 117.42, 116.64, 109.01, 52.10. ¹⁹F NMR (400 MHz, MeOD) δ -57.84.

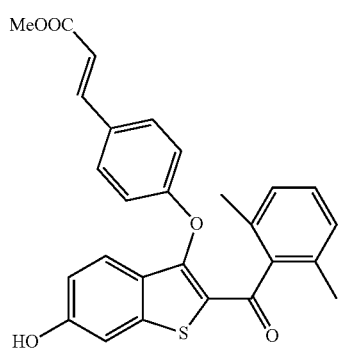 [SMILES: COC(=O)/C=C/c1ccc(Oc2c(C(=O)c3c(C)cccc3C)sc3cc(O)ccc23)cc1]

Methyl (E)-3-(4-((2-(2,6-dimethylbenzoyl)-6-hydroxybenzo[b]thiophen-3-yl)oxy)phenyl)acrylate ¹H NMR (400 MHz, MeOD) δ 7.57 (d, J = 16.0 Hz, 1H), 7.35 (d, J = 8.7 Hz, 2H), 7.30-7.24 (m, 2H), 7.03 (t, J = 7.6 Hz, 1H), 6.88-6.80 (m, 3H), 6.45 (d, J = 8.7 Hz, 2H), 6.36 (d, J = 16.0 Hz, 1H), 3.75 (s, 3H), 2.06 (s, 6H). ¹³C NMR (100 MHz, MeOD) δ 194.05, 169.17, 160.99, 160.62, 150.45, 145.33, 143.89, 141.52, 134.80, 130.57, 130.30, 129.92, 128.47, 126.75, 125.99, 117.57, 117.27, 116.42, 109.04, 52.10, 19.34.

Example 3: Synthetic Procedures for Representative Compounds and Characterization of Compounds 1-22

Scheme 6: Synthesis of (E)-3-(4-((2-(4-Fluoro-2-methylbenzoyl)-6-hydroxybenzo[b]thiophen-3-yl)oxy)phenyl)acrylic acid (Compound 1)

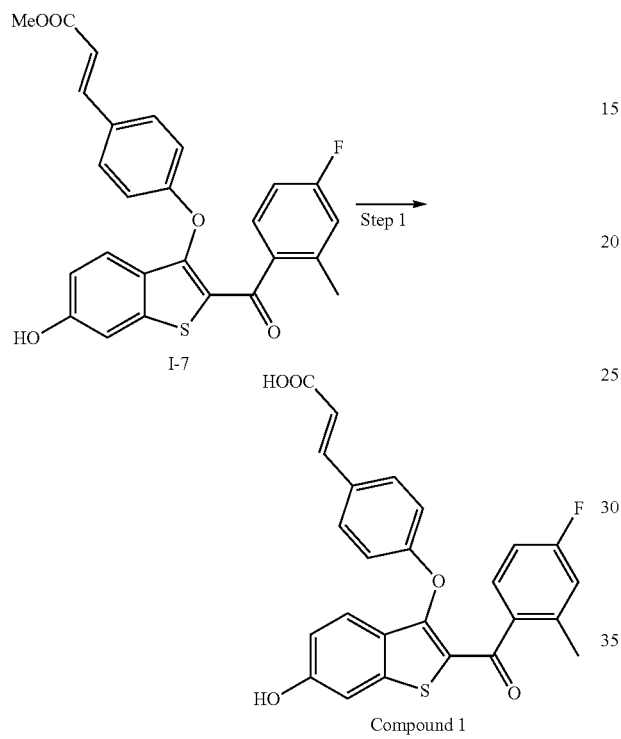

Scheme 7: Synthesis of 5-((6-Hydroxy-2-(2-methylbenzoyl)benzo[b]thiophen-3-yl)oxy)-2-naphthoic acid (Compound 9)

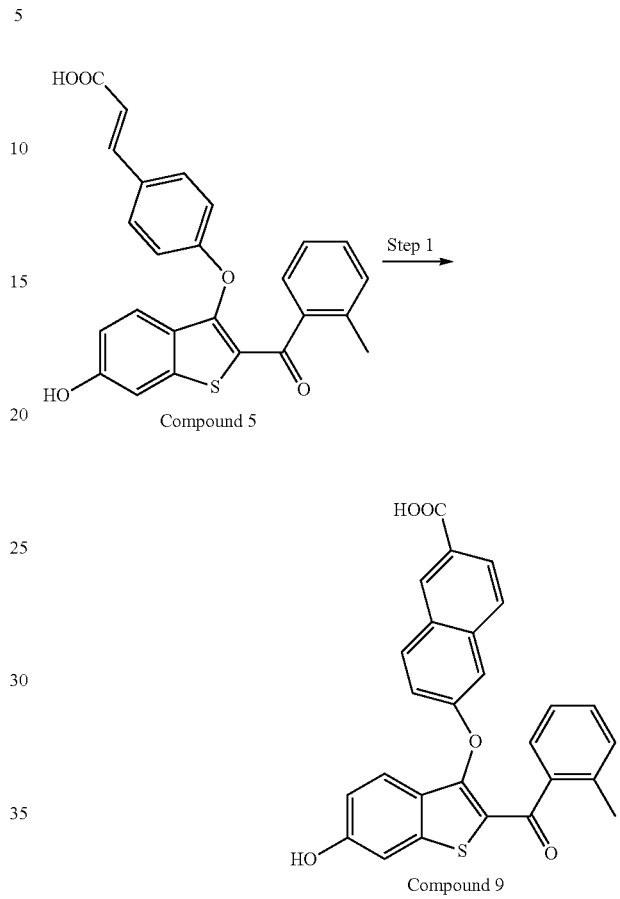

To a solution of Compound I-7 (75 mg, 0.16 mmol) in methanol (2 ml) was added 10% LiOH solution (2 ml) drop-wise. The reaction was monitored by TLC and once TLC indicated consumption of starting materials, the reaction was quenched by 1 N HCl/ice water. After stirring for 10 minutes, the mixture was extracted with ethyl acetate. The organic layers were collected and purified by C18 chromatography (5%-60% ethyl methanol in water) to afford 71 mg as a white powder (99%). $^1$H NMR (400 MHz, CDCl$_3$) δ 7.58 (d, J=16.0 Hz, 1H), 7.37 (d, J=9.0 Hz, 1H), 7.28 (t, J=8.8 Hz, 3H), 7.20 (dd, J=8.5, 5.9 Hz, 1H), 7.00 (dd, J=8.6, 2.3 Hz, 1H), 6.93 (dd, J=9.0, 2.2 Hz, 1H), 6.81 (td, J=8.3, 2.4 Hz, 1H), 6.55 (d, J=8.7 Hz, 2H), 6.29 (d, J=16.0 Hz, 1H), 3.91 (s, 3H), 3.79 (s, 3H). $^{13}$C NMR (100 MHz, CDCl$_3$) δ 186.10, 167.53, 163.16 (d, J=253.1 Hz), 161.27, 159.30, 148.85, 143.81, 142.73, 135.48 (d, J=3.7 Hz), 132.49 (d, J=10.6 Hz), 129.79 (d, J=9.3 Hz), 129.56, 129.36, 127.18, 126.36, 124.83, 117.18 (d, J=24.9 Hz), 116.91, 116.72, 115.45, 113.83 (d, J=21.6 Hz), 105.22, 55.91, 51.82.

Compounds 2-8 and 11-22 were made via an analogous procedure for the synthesis of Compound 1 utilizing appropriate starting materials. Characterization for these compounds is shown below in Table 6.

Compound 5 (100 mg, 0.21 mmol) was dissolved in 3 mL of anhydrous dichloromethane at room temperature under argon atmosphere. The solution was cooled using an ice water bath and BF$_3$.SMe$_2$ (1 ml, 4.2 mmol) was added drop-wise. After stirring for 30 minutes, the solution was allowed to warm to 35° C. The reaction mixture was stirred until starting material was consumed, as monitored by TLC, and then quenched by saturated NaHCO$_3$/ice water. The reaction mixture was extracted with ethyl acetate and washed with brine. The organic extracts were combined, dried over anhydrous Na$_2$SO$_4$, concentrated in vacuum, and purified by flash chromatography (5%-60% ethyl acetate in hexane) to afford 37 mg white powder (38%). $^1$H NMR (400 MHz, MeOD) δ 8.47 (s, 1H), 7.93 (d, J=8.4 Hz, 1H), 7.72 (d, J=8.9 Hz, 1H), 7.56 (d, J=8.4 Hz, 1H), 7.40 (d, J=8.8 Hz, 1H), 7.30 (d, J=1.9 Hz, 1H), 7.28-7.08 (m, 2H), 7.01 (t, J=7.4 Hz, 1H), 6.94 (d, J=7.6 Hz, 1H), 6.88 (dd, J=8.8, 2.1 Hz, 1H), 6.79 (s, 1H), 6.74 (dd, J=8.9, 2.4 Hz, 1H), 1.95 (s, 3H). $^{13}$C NMR (100 MHz, MeOD) δ 192.50, 169.84, 160.87, 159.24, 150.50, 143.78, 140.65, 137.54, 136.54, 132.21, 131.70, 131.42, 131.18, 130.09, 128.34, 128.08, 127.69, 127.38, 127.05, 126.27, 125.78, 118.69, 117.51, 110.58, 108.92, 19.19. ESI-HRMS (m/z): [M+H]$^+$ calcd. for C$_{27}$H$_{18}$O$_5$S: 455.0953; observed, 455.0939.

Scheme 8: Synthesis of 8-((6-Hydroxy-2-(2-methyl-benzoyl)benzo[b]thiophen-3-yl)oxy)quinoline-3-carboxylic Acid (Compound 10)

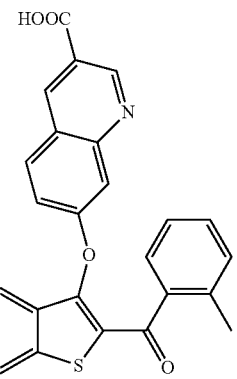

Compound 10 was prepared following the procedure for the synthesis of Compound 9 to afford 33 mg (57%). $^1$H NMR (400 MHz, MeOD) δ 9.20 (s, 1H), 8.85 (s, 1H), 7.83 (d, J=9.0 Hz, 1H), 7.44 (d, J=8.8 Hz, 1H), 7.31 (s, 1H), 7.27-7.13 (m, 2H), 7.04-6.81 (m, 5H), 1.97 (s, 3H). $^{13}$C NMR (100 MHz, MeOD with TFA vapor) δ 192.08, 165.75, 162.47, 161.00, 151.79, 151.11, 149.43, 143.78, 140.53, 140.32, 136.47, 132.26, 131.43, 131.32, 128.29, 127.90, 126.64, 126.32, 125.56, 124.53, 119.98, 117.75, 110.96, 108.96, 19.21. ESI-HRMS (m/z): [M+H]$^+$ calcd. for $C_{26}H_{17}NO_5S$: 456.0906; observed, 456.0893.

TABLE 6

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 1 | 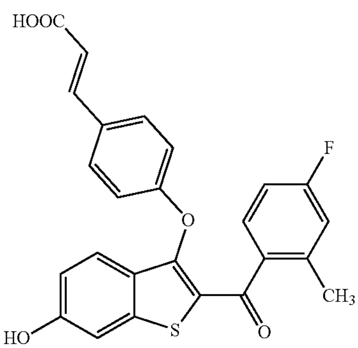 [SMILES: Cc1cc(F)ccc1C(=O)c1sc2cc(O)ccc2c1Oc1ccc(/C=C/C(=O)O)cc1] | $^1$H NMR (400 MHz, CDCl$_3$) δ 7.58 (d, J = 16.0 Hz, 1H), 7.37 (d, J = 9.0 Hz, 1H), 7.28 (t, J = 8.8 Hz, 3H), 7.20 (dd, J = 8.5, 5.9 Hz, 1H), 7.00 (dd, J = 8.6, 2.3 Hz, 1H), 6.93 (dd, J = 9.0, 2.2 Hz, 1H), 6.81 (td, J = 8.3, 2.4 Hz, 1H), 6.55 (d, J = 8.7 Hz, 2H), 6.29 (d, J = 16.0 Hz, 1H), 3.91 (s, 3H), 3.79 (s, 3H). $^{13}$C NMR (100 MHz, CDCl$_3$) δ 186.10, 167.53, 163.16 (d, J = 253.1 Hz), 161.27, 159.30, 148.85, 143.81, 142.73, 135.48 (d, J = 3.7 Hz), 132.49 (d, J = 10.6 Hz), 129.79 (d, J = 9.3 Hz), 129.56, 129.36, 127.18, 126.36, 124.83, 117.18 (d, J = 24.9 Hz), 116.91, 116.72, 115.45, 113.83 (d, J = 21.6 Hz), 105.22, 55.91, 51.82. | 1.0 +/- 0.05 | 0.4 +/- 0.07 |
| 2 | 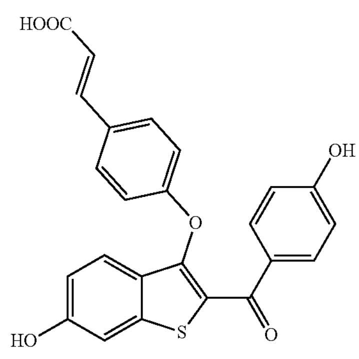 [SMILES: O=C(O)/C=C/c1ccc(Oc2c(C(=O)c3ccc(O)cc3)sc3cc(O)ccc23)cc1] | (E)-3-(4-((6-Hydroxy-2-(4-hydroxybenzoyl)benzo[b]thiophen-3-yl)oxy)phenyl)acrylic acid $^1$H NMR (400 MHz, MeOD) δ 7.61 (d, J = 8.7 Hz, 2H), 7.55 (d, J = 16.0 Hz, 1H), 7.43 (d, J = 8.8 Hz, 1H), 7.39 (d, J = 8.7 Hz, 2H), 7.26 (d, J = 2.1 Hz, 1H), 6.92 (dd, J = 8.8, 2.1 Hz, 1H), 6.74 (d, J = 8.7 Hz, 2H), 6.67 (d, J = 8.7 Hz, 2H), 6.31 (d, J = 16.0 Hz, 1H). $^{13}$C NMR (100 MHz, MeOD) δ 189.36, 170.39, 163.61, 161.20, 160.04, 148.16, 145.39, 142.57, 132.95, 130.77, 130.74, 130.42, 126.91, 125.84, 125.15, 118.03, 117.20, 117.05, 115.87, 108.68.24 | 3.9 +/- 0.06 (54% Emax) | No Inhiibition |

TABLE 6-continued

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 3 | 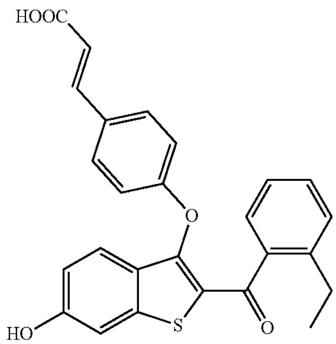 [SMILES: CCc1ccccc1C(=O)c1sc2cc(O)ccc2c1Oc1ccc(/C=C/C(=O)O)cc1] | (E)-3-(4-((2-(2-Ethylbenzoyl)-6-hydroxybenzo[b]thiophen-3-yl)oxy)phenyl) acrylic acid $^1$H NMR (400 MHz, MeOD) δ 7.55 (d, J = 16.0 Hz, 1H), 7.42-7.26 (m, 5H), 7.24 (d, J = 7.6 Hz, 1H), 7.15 (d, J = 7.7 Hz, 1H), 7.07 (t, J = 7.5 Hz, 1H), 6.88 (dd, J = 8.8, 2.1 Hz, 1H), 6.47 (d, J = 8.7 Hz, 2H), 6.32 (d, J = 16.0 Hz, 1H), 2.47 (q, J = 7.6 Hz, 2H), 1.02 (t, J = 7.6 Hz, 3H). $^{13}$C NMR (101 MHz, MeOD) δ 192.52, 170.42, 160.94, 160.82, 150.26, 145.35, 143.68, 142.88, 140.37, 131.31, 130.64, 130.43, 129.91, 128.29, 127.98, 126.92, 126.31, 125.81, 118.08, 117.47, 116.67, 108.91, 27.10, 15.95. | 1.2 +/− 0.04 | 0.9 +/− 0.04 |
| 4 | 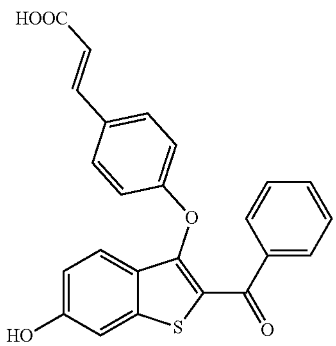 [SMILES: O=C(O)/C=C/c1ccc(Oc2c(C(=O)c3ccccc3)sc3cc(O)ccc23)cc1] | (E)-3-(4-((2-Benzoyl-6-hydroxybenzo[b]thiophen-3-yl)oxy)phenyl) acrylic acid $^1$H NMR (400 MHz, MeOD) δ 7.66-7.58 (m, 2H), 7.55 (d, J = 16.0 Hz, 1H), 7.50 (d, J = 7.4 Hz, 1H), 7.43-7.34 (m, 5H), 7.28 (d, J = 2.0 Hz, 1H), 6.92 (dd, J = 8.8, 2.1 Hz, 1H), 6.61 (d, J = 8.8 Hz, 2H), 6.32 (d, J = 16.0 Hz, 1H). $^{13}$C NMR (100 MHz, MeOD) δ 190.76, 170.39, 161.08, 160.51, 149.38, 145.33, 143.23, 139.90, 133.38, 130.77, 130.47, 129.70, 129.13, 126.82, 125.95, 125.55, 118.13, 117.38, 116.96, 108.75 | 13 +/− 0.08 | 2.2 +/− 0.1 |
| 5 | 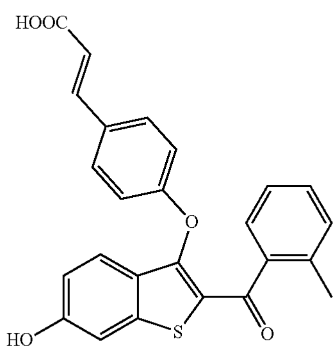 [SMILES: Cc1ccccc1C(=O)c1sc2cc(O)ccc2c1Oc1ccc(/C=C/C(=O)O)cc1] | (E)-3-(4-((6-Hydroxy-2-(2-methylbenzoyl)benzo[b]thiophen-3-yl)oxy)phenyl) acrylic acid $^1$H NMR (400 MHz, MeOD) δ 7.54 (d, J = 16.0 Hz, 1H), 7.32 (dd, J = 8.7, 6.0 Hz, 3H), 7.28-7.2 (m, 3H), 7.06-7.03 (m, 2H), 6.87 (dd, J = 8.8, 2.0 Hz, 1H), 6.44 (d, J = 8.7 Hz, 2H), 6.30 (d, J = 16.0 Hz, 1H), 2.07 (s, 3H). $^{13}$C NMR (100 MHz, MeOD) δ 192.43, 170.39, 161.05, 160.78, 150.29, 145.35, 143.66, 140.66, 136.53, 131.49, 131.22, 130.61, 130.37, 128.35, 127.64, 126.93, 126.29, 125.73, 118.02, 117.47, 116.54, 108.90, 19.32. | 1.3 +/− .06 | 0.9 +/− .09 |
| 6 | 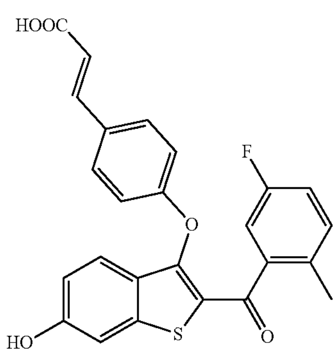 [SMILES: Cc1ccc(F)cc1C(=O)c1sc2cc(O)ccc2c1Oc1ccc(/C=C/C(=O)O)cc1] | (E)-3-(4-((2-(5-Fluoro-2-methylbenzoyl)-6-hydroxybenzo[b]thiophen-3-yl)oxy)phenyl) acrylic acid $^1$H NMR (400 MHz, MeOD) δ 7.56 (d, J = 16.0 Hz, 1H), 7.41-7.34 (m, 3H), 7.27 (d, J = 2.0 Hz, 1H), 7.10-7.06 (m, 1H), 7.02-6.93 (m, 2H), 6.89 (dd, J = 8.9, 2.1 Hz, 1H), 6.53 (d, J = 8.8 Hz, 2H), 6.33 (d, J = 16.0 Hz, 1H), 2.08 (s, 3H). $^{13}$C NMR (100 MHz, MeOD) δ 190.69, 170.37, 161.92 (d, J = 244.8 Hz), 161.03, 160.90, 150.60, 145.27, 143.95, 142.21 (d, J = 6.5 Hz), 133.18 (d, J = 7.5 Hz), 132.15 (d, J = 3.4 Hz), 130.74, 130.62, 127.31, 126.78, 125.88, 118.21, 117.63 (d, J = 21.3 Hz), 117.59, 116.48, 114.82 (d, J = 23.3 Hz), 108.93, 18.48. | 4.7 +/− 0.04 | 0.7 +/− 0.3 |

TABLE 6-continued

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 7 | 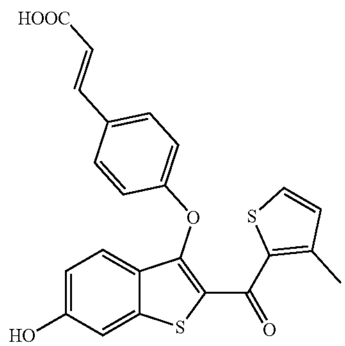 [SMILES: Cc1ccsc1C(=O)c1sc2cc(O)ccc2c1Oc1ccc(/C=C/C(=O)O)cc1] | (E)-3-(4-((6-Hydroxy-2-(3-methylthiophene-2-carbonyl)benzo[b]thiophen-3-yl)oxy)phenyl) acrylic acid<br>$^1$H NMR (400 MHz, MeOD) δ 7.59-7.51 (m, 2H), 7.49 (d, J = 8.8 Hz, 1H), 7.40 (d, J = 8.7 Hz, 2H), 7.26 (d, J = 2.1 Hz, 1H), 6.93 (dd, J = 8.8, 2.1 Hz, 1H), 6.90 (d, J = 4.9 Hz, 1H), 6.70 (d, J = 8.7 Hz, 2H), 6.32 (d, J = 16.0 Hz, 1H), 2.23 (s, 3H). $^{13}$C NMR (100 MHz, MeOD) δ 182.84, 170.46, 161.42, 160.27, 148.95, 145.51, 145.27, 142.41, 136.91, 132.55, 132.20, 130.78, 130.65, 126.84, 125.52, 125.14, 118.24, 117.38, 117.08, 108.63, 15.66. | 12.5 +/− 0.01 | 2.8 +/− 0.16 |
| 8 | 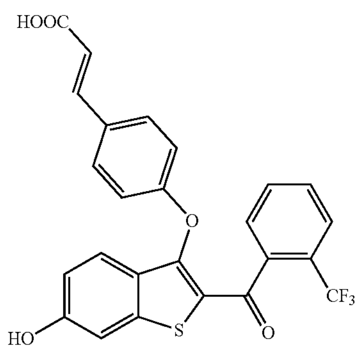 [SMILES: O=C(O)/C=C/c1ccc(Oc2c(C(=O)c3ccccc3C(F)(F)F)sc3cc(O)ccc23)cc1] | (E)-3-(4-((6-Hydroxy-2-(2-(trifluoromethyl)benzoyl)benzo[b]thiophen-3-yl)oxy)phenyl) acrylic acid<br>$^1$H NMR (400 MHz, Acetone) δ 7.69 (d, J = 7.9 Hz, 1H), 7.62-7.53 (m, 2H), 7.53-7.46 (m, 4H), 7.45 (d, J = 1.9 Hz, 1H), 7.31 (d, J = 8.8 Hz, 1H), 6.97 (dd, J = 8.9, 2.1 Hz, 1H), 6.57 (d, J = 8.8 Hz, 2H), 6.39 (d, J = 16.0 Hz, 1H). $^{13}$C NMR (100 MHz, Acetone) $^{13}$C NMR (101 MHz, CDCl$_3$) δ 187.60, 167.78, 160.17, 159.68, 149.95, 144.51, 143.23, 139.58, 132.63, 130.73, 130.49, 130.33, 128.38, 127.45, 127.24 (q, J = 31.9 Hz), 127.11 (q, J = 4.6 Hz), 126.14, 125.91, 124.85 (q, J = 273.3 Hz), 118.10, 117.32, 116.51, 109.12. | 2.7 +/− 0.11 (61% Emax) | 1.2 +/− 0.08 (65% Emax) |
| 9 | 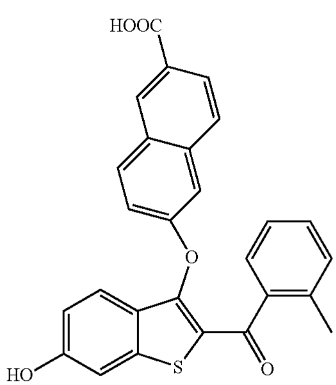 [SMILES: Cc1ccccc1C(=O)c1sc2cc(O)ccc2c1Oc1ccc2cc(C(=O)O)ccc2c1] | $^1$H NMR (400 MHz, MeOD) δ 8.47 (s, 1H), 7.93 (d, J = 8.4 Hz, 1H), 7.72 (d, J = 8.9 Hz, 1H), 7.56 (d, J = 8.4 Hz, 1H), 7.40 (d, J = 8.8 Hz, 1H), 7.30 (d, J = 1.9 Hz, 1H), 7.28-7.08 (m, 2H), 7.01 (t, J = 7.4 Hz, 1H), 6.94 (d, J = 7.6 Hz, 1H), 6.88 (dd, J = 8.8, 2.1 Hz, 1H), 6.79 (s, 1H), 6.74 (dd, J = 8.9, 2.4 Hz, 1H), 1.95 (s, 3H). $^{13}$C NMR (100 MHz, MeOD) δ 192.50, 169.84, 160.87, 159.24, 150.50, 143.78, 140.65, 137.54, 136.54, 132.21, 131.70, 131.42, 131.18, 130.09, 128.34, 128.08, 127.69, 127.38, 127.05, 126.27, 125.78, 118.69, 117.51, 110.58, 108.92, 19.19. ESI-HRMS (m/z): [M + H]$^+$ calcd. for C$_{27}$H$_{18}$O$_5$S: 455.0953; observed, 455.0939. | 4.8 +/− 0.06 | 2.4 +/− 0.12 |

TABLE 6-continued

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 10 | 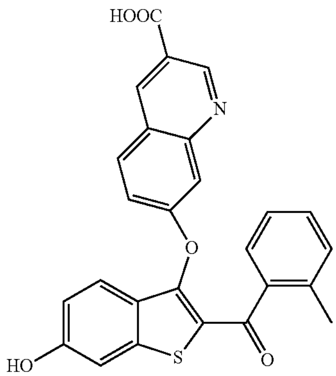 [SMILES: Cc1ccccc1C(=O)c1sc2cc(O)ccc2c1Oc1ccc2cc(C(=O)O)cnc2c1] | $^1$H NMR (400 MHz, MeOD) δ 9.20 (s, 1H), 8.85 (s, 1H), 7.83 (d, J = 9.0 Hz, 1H), 7.44 (d, J = 8.8 Hz, 1H), 7.31 (s, 1H), 7.27-7.13 (m, 2H), 7.04-6.81 (m, 5H), 1.97 (s, 3H). $^{13}$C NMR (100 MHz, MeOD with TFA vapor) δ 192.08, 165.75, 162.47, 161.00, 151.79, 151.11, 149.43, 143.78, 140.53, 140.32, 136.47, 132.26, 131.43, 131.32, 128.29, 127.90, 126.64, 126.32, 125.56, 124.53, 119.98, 117.75, 110.96, 108.96, 19.21. ESI-HRMS (m/z): [M + H]$^+$ calcd. for C$_{26}$H$_{17}$NO$_5$S: 456.0906; observed, 456.0893 | 32.3 +/− 0.19 (52% Emax) | No Inhibition |
| 11 | 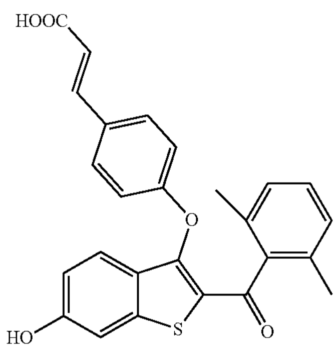 [SMILES: Cc1cccc(C)c1C(=O)c1sc2cc(O)ccc2c1Oc1ccc(/C=C/C(=O)O)cc1] | (E)-3-(4-((2-(2,6-Dimethylbenzoyl)-6-hydroxybenzo[b]thiophen-3-yl)oxy)phenyl) acrylic acid $^1$H NMR (400 MHz, MeOD) δ 7.55 (d, J = 16.0 Hz, 1H), 7.32 (d, J = 8.7 Hz, 2H), 7.27-7.19 (m, 2H), 7.01 (t, J = 7.6 Hz, 1H), 6.87-6.77 (m, 3H), 6.43 (d, J = 8.6 Hz, 2H), 6.31 (d, J = 16.0 Hz, 1H), 2.04 (s, 6H). $^{13}$C NMR (100 MHz, MeOD) δ 194.06, 170.40, 160.93, 160.50, 150.47, 145.38, 143.86, 141.47, 134.76, 130.48, 130.35, 129.90, 128.44, 126.74, 125.99, 117.97, 117.55, 116.38, 109.04, 19.35. | 0.5 +/− 0.04 | 0.1 +/− 0.07 |
| 12 | 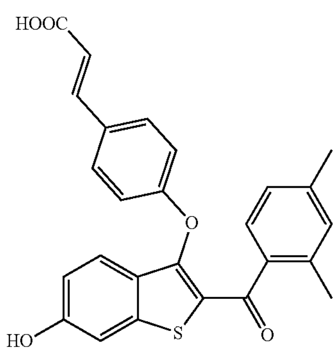 [SMILES: Cc1ccc(C(=O)c2sc3cc(O)ccc3c2Oc2ccc(/C=C/C(=O)O)cc2)c(C)c1] | (E)-3-(4-((2-(2,4-Dimethylbenzoyl)-6-hydroxybenzo[b]thiophen-3-yl)oxy)phenyl) acrylic acid $^1$H NMR (400 MHz, Acetone) δ 7.58 (d, J = 16.0 Hz, 1H), 7.50-7.38 (m, 4H), 7.25 (d, J = 7.7 Hz, 1H), 7.01 (dd, J = 8.8, 2.1 Hz, 1H)), 6.96-6.86 (m, 2H), 6.57 (d, J = 8.7 Hz, 2H), 6.38 (d, J = 16.0 Hz, 1H), 2.29 (s, 3H), 2.07 (s, 3H). $^{13}$C NMR (100 MHz, Acetone) δ 190.44, 167.80, 160.72, 159.80, 148.66, 144.67, 142.52, 141.14, 137.47, 136.47, 131.96, 130.35, 130.01, 128.72, 127.86, 126.99, 126.55, 125.39, 117.81, 117.15, 116.34, 108.90, 21.31, 19.33. | 0.4 +/− 0.04 | 0.1 +/− 0.08 |
| 13 | 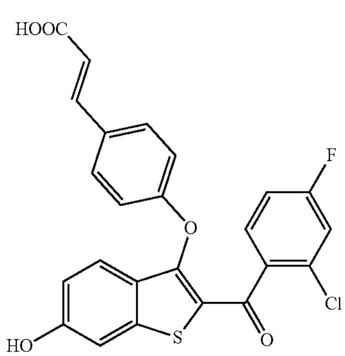 [SMILES: O=C(O)/C=C/c1ccc(Oc2c(C(=O)c3ccc(F)cc3Cl)sc3cc(O)ccc23)cc1] | (E)-3-(4-((2-(2-Chloro-4-fluorobenzoyl)-6-hydroxybenzo[b]thiophen-3-yl)oxy)phenyl) acrylic acid LC-MS M/Z (M − H)$^-$: 467.9 | 2.2 +/− 0.12 | 0.4 +/− 0.13 |

TABLE 6-continued

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 14 | 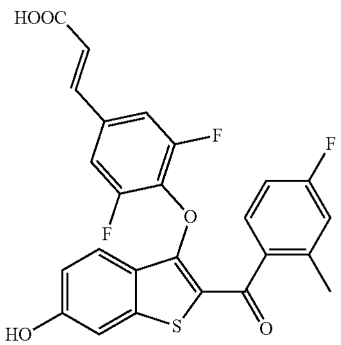 [SMILES: Cc1cc(F)ccc1C(=O)c1sc2cc(O)ccc2c1Oc1c(F)cc(/C=C/C(=O)O)cc1F] | (E)-3-(3,5-Difluoro-4-((2-(4-fluoro-2-methylbenzoyl)-6-hydroxybenzo[b]thiophen-3-yl)oxy)phenyl) acrylic acid LC-MS M/Z (M − H)$^-$: 483.4 | >10 | >10 |
| 15 | 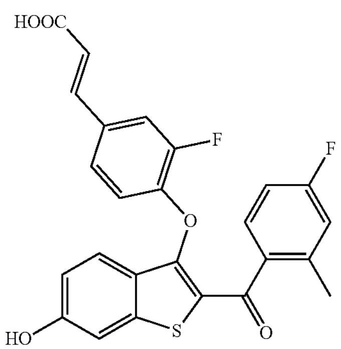 [SMILES: Cc1cc(F)ccc1C(=O)c1sc2cc(O)ccc2c1Oc1ccc(/C=C/C(=O)O)cc1F] | (E)-3-(3-Fluoro-4-((2-(4-fluoro-2-methylbenzoyl)-6-hydroxybenzo[b]thiophen-3-yl)oxy)phenyl) acrylic acid LC-MS M/Z (M − H)$^-$: 465.4 | <10 | <10 |
| 16 | 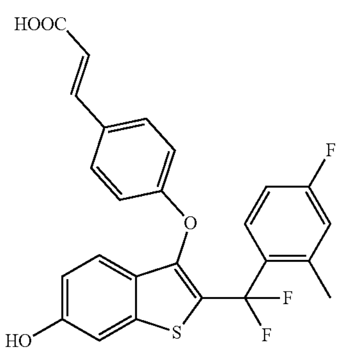 [SMILES: Cc1cc(F)ccc1C(F)(F)c1sc2cc(O)ccc2c1Oc1ccc(/C=C/C(=O)O)cc1] | (E)-3-(4-((2-(Difluoro(4-fluoro-2-methylphenyl)methyl)-6-hydroxybenzo[b]thiophen-3-yl)oxy)phenyl)acrylic acid LC-MS M/Z (M − H)$^-$: 469.5 | <100 | <100 |
| 17 | 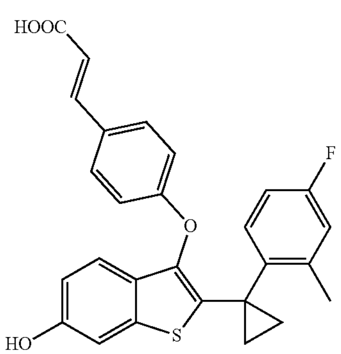 [SMILES: Cc1cc(F)ccc1C1(c2sc3cc(O)ccc3c2Oc2ccc(/C=C/C(=O)O)cc2)CC1] | (E)-3-(4-((2-(1-(4-Fluoro-2-methylphenyl)cyclopropyl)-6-hydroxybenzo[b]thiophen-3-yl)oxy)phenyl) acrylic acid LC-MS M/Z (M − H)$^-$: 459.5 | <100 | <100 |

TABLE 6-continued

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 18 | 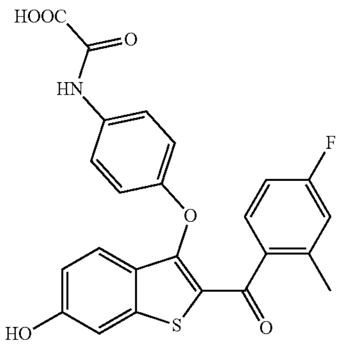 [SMILES: Cc1cc(F)ccc1C(=O)c1sc2cc(O)ccc2c1Oc1ccc(NC(=O)C(=O)O)cc1] | 2-((4-((2-(4-Fluoro-2-methylbenzoyl)-6-hydroxybenzo[b]thiophen-3-yl)oxy)phenyl) amino)-2-oxoacetic acid<br>$^{1}$H NMR (400 MHz, MeOD) δ 7.46 (d, J = 8.3 Hz, 2H), 7.38-7.27 (m, 2H), 7.24 (s, 1H), 6.90-6.77 (m, 3H), 6.46 (d, J = 8.2 Hz, 2H), 2.11 (s, 3H). $^{13}$C NMR (100 MHz, MeOD) δ 191.26, 164.87 (d, J = 248.6 Hz), 160.76, 156.78, 150.82, 143.70, 140.40 (d, J = 8.6 Hz), 136.90, 136.87, 133.35, 131.10 (d, J = 9.1 Hz), 127.30, 127.03, 125.84, 123.09, 118.11 (d, J = 21.7 Hz), 117.38, 116.16, 113.05 (d, J = 21.9 Hz), 108.85, 19.46. | 1.7 +/− 0.07 (64% Emax) | No Inhibition |
| 19 | 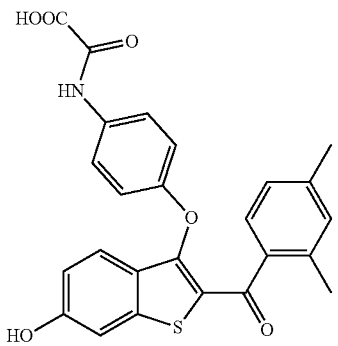 [SMILES: Cc1ccc(C(=O)c2sc3cc(O)ccc3c2Oc2ccc(NC(=O)C(=O)O)cc2)c(C)c1] | 2-((4-((2-(2,4-Dimethylbenzoyl)-6-hydroxybenzo[b]thiophen-3-yl)oxy)phenyl) amino)-2-oxoacetic acid<br>LC-MS M/Z(M − H)$^−$: 460.1 | >10 | No Inhibition |
| 20 | 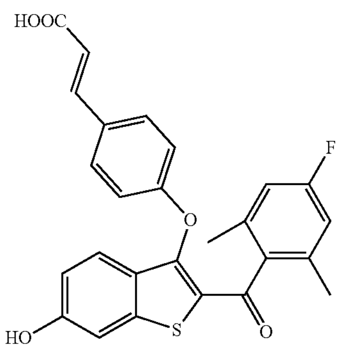 [SMILES: Cc1cc(F)cc(C)c1C(=O)c1sc2cc(O)ccc2c1Oc1ccc(/C=C/C(=O)O)cc1] | (E)-3-(4-((2-(4-Fluoro-2,6-dimethylbenzoyl)-6-hydroxybenzo[b]thiophen-3-yl)oxy)phenyl) acrylic acid<br>$^{1}$H NMR (400 MHz, Acetone-d6) δ 7.60 (d, J = 16.0 Hz, 1H), 7.51 (d, J = 8.7 Hz, 2H), 7.44 (d, J = 1.7 Hz, 1H), 7.37 (d, J = 8.8 Hz, 1H), 6.99 (dd, J = 8.8, 1.9 Hz, 1H), 6.66 (d, J = 9.8 Hz, 2H), 6.60 (d, J = 8.6 Hz, 2H), 6.40 (d, J = 16.0 Hz, 1H), 2.10 (s, 6H). $^{13}$C NMR (100 MHz, Acetone-d6) δ 191.13, 167.89, 163.21 (d, J = 244.9 Hz), 160.08, 149.15, 144.65, 142.99, 137.66, 137.58 (d, J = 8.8 Hz), 130.34, 130.13, 128.63, 126.65, 125.79, 117.89, 117.34, 115.99, 114.64 (d, J = 21.5 Hz), 109.12, 19.34, 19.32. | 0.4 +/− 0.03 | <0.1 |
| 21 | 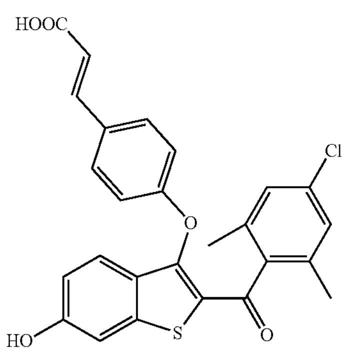 [SMILES: Cc1cc(Cl)cc(C)c1C(=O)c1sc2cc(O)ccc2c1Oc1ccc(/C=C/C(=O)O)cc1] | (E)-3-(4-((2-(4-Chloro-2,6-dimethylbenzoyl)-6-hydroxybenzo[b]thiophen-3-yl)oxy)phenyl) acrylic acid<br>$^{1}$H NMR (400 MHz, Acetone-d6) δ 7.60 (d, J = 16.0 Hz, 1H), 7.51 (d, J = 8.6 Hz, 2H), 7.45 (d, J = 1.7 Hz, 1H), 7.39 (d, J = 8.8 Hz, 1H), 7.00 (dd, J = 8.8, 1.9 Hz, 1H), 6.91 (s, 2H), 6.58 (d, J = 8.6 Hz, 2H), 6.40 (d, J = 16.0 Hz, 1H), 2.09 (s, 6H). $^{13}$C NMR (100 MHz, Acetone-d6) δ 190.91, 167.77, 160.17, 160.00, 149.30, 144.62, 143.07, 139.99, 136.85, 134.53, 130.26, 130.17, 128.40, 127.88, 126.67, 125.82, 117.94, 117.38, 115.91, 109.13, 19.12. | 0.3 +/− 0.04 | <0.1 |

TABLE 6-continued

Characterization and Biological Data of Compounds 1-22

| Cmpd # | Structure | Name/Physical Data | MCF-7:5C IC$_{50}$ (nM) | MCF-7WS8 IC$_{50}$ (nM) |
|---|---|---|---|---|
| 22 | (structure) | (E)-3-(4-((6-Hydroxy-2-(2,4,6-trimethylbenzoyl)benzo[b]thiophen-3-yl)oxy)phenyl) acrylic acid $^1$H NMR (400 MHz, MeOD) δ 7.55 (d, J = 15.9 Hz, 1H), 7.34 (d, J = 8.7 Hz, 2H), 7.29 (d, J = 8.9 Hz, 1H), 7.26 (d, J = 1.9 Hz, 1H), 6.86 (dd, J = 8.8, 2.1 Hz, 1H), 6.63 (s, 2H), 6.44 (d, J = 8.6 Hz, 2H), 6.32 (d, J = 15.9 Hz, 1H), 2.18 (s, 3H), 2.01 (s, 6H). $^{13}$C NMR (100 MHz, MeOD) δ 194.48, 160.95, 160.62, 150.30, 145.28, 143.76, 139.89, 138.64, 134.74, 130.39, 130.27, 129.13, 128.72, 126.95, 125.91, 118.20, 117.55, 116.26, 109.00, 21.13, 19.30. | 0.5 +/− 0.03 | <0.1 |

Example 4: Synthesis of Compounds 23-26

Compounds 23-26 can be prepared following the general synthetic scheme shown below (General Synthetic Route 6). To a stirred solution of chloro tricycliclactam in dioxane was added the appropriate aminopyridine intermediate followed by the addition of Pd$_2$(dba)$_3$, BINAP, and sodium-tert-butoxide. The contents were heated to reflux. The crude mixture was then purified to afford the desired compound. The structure of Compounds 23-26 are shown in Table 7 below.

General Synthetic Route 6

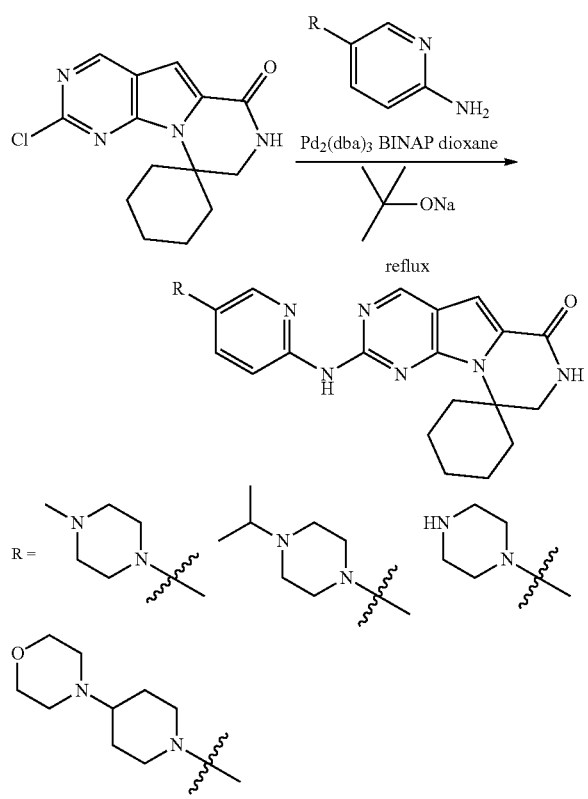

Compound 23 was synthesized using the conditions of synthetic route 6 as described in U.S. Pat. No. 8,598,197. $^1$H NMR (400 MHz, D2O) ppm 1.47 (br. s., 6H) 1.72 (br. s., 2H) 1.92 (br. s., 2H) 2.77 (br. s., 3H) 3.18 (br. s., 2H) 3.46 (br. s., 2H) 3.63 (br. s., 2H) 3.66 (d, J=6.15 Hz, 2H) 3.80 (br. s., 2H) 7.25 (s, 1H) 7.63 (br. s., 2H) 7.94 (br. s., 1H) 8.10 (br. s., 1H) 8.39 (br. s., 1H) 9.08 (br. s., 1H) 11.59 (br. s., 1H). LCMS (ESI) 447 (M+H).

Compound 24 was synthesized using synthetic route 6 as described in U.S. Pat. No. 8,598,197. 1H NMR (600 MHz, DMSO-d$_6$) ppm 1.27-1.44 (br. m., 9H) 1.79-1.87 (br. m., 5H) 2.62-2.69 (br. m., 2H) 3.16-3.36 (br. m., 4H) 3.63-3.73 (m., 5H) 3.85-3.89 (br. m., 2H) 7.11 (s, 1H) 7.31 and 7.28 (d., 1H) 7.69 and 7.70 (d., 1H) 7.86, 7.86, 7.88, 7.89 (dd., 1H) 8.81 (s., 1H) LCMS (ESI) 447 (M+H).

Compound 25 was synthesized using synthetic route 6 as described in U.S. Pat. No. 8,598,197. 1H NMR (600 MHz, DMSO-d$_6$) ppm 1.27-1.64 (m, 6H) 1.71 (br. s., 2H) 1.91 (br. s., 2H) 2.80 (br. s., 1H) 3.17-3.24 (m, 2H) 3.41 (br. s., 4H) 3.65 (br. s., 4H) 7.26 (br. s., 1H) 7.63 (br. s., 1H) 7.94 (br. s., 1H) 8.13 (br. s., 1H) 8.40 (br. s., 1H) 9.09 (br. s., 1H) 9.62 (br. s., 1H) 11.71 (br. s., 1H). LCMS (ESI) 433 (M+H).

Compound 26 was synthesized using synthetic route 6 as described in U.S. Pat. No. 8,598,197. $^1$H NMR (600 MHz, DMSO-d$_6$) δ ppm 0.84 (t, J=7.61 Hz, 2H) 1.13-1.39 (m, 4H) 1.46 (d, J=14.05 Hz, 2H) 1.64-1.99 (m, 6H) 2.21 (br. s., 1H) 2.66-2.89 (m, 2H) 3.06 (br. s., 1H) 3.24-3.36 (m, 1H) 3.37-3.50 (m, 2H) 3.56-3.72 (m, 2H) 3.77-4.00 (m, 4H) 4.02-4.19 (m, 2H) 7.25 (s, 1H) 7.50-7.75 (m, 2H) 7.89 (d, J=2.93 Hz, 1H) 8.14 (d, J=7.32 Hz, 1H) 8.38 (br. s., 1H) 9.06 (s, 1H) 11.53 (br. s., 1H). LCMS ESI (M+H) 517.

TABLE 7

Structure of Compounds 23-26

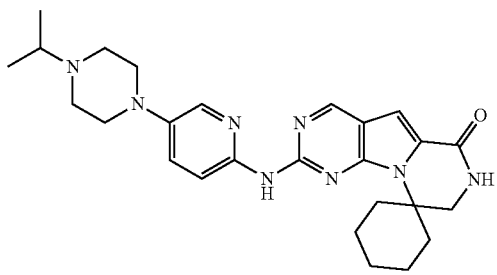 [SMILES: CC(C)N1CCN(c2ccc(Nc3ncc4cc5n(c4n3)C3(CCCCC3)CNC5=O)nc2)CC1]
23

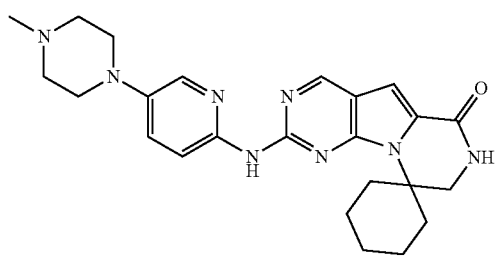 [SMILES: CN1CCN(c2ccc(Nc3ncc4cc5n(c4n3)C3(CCCCC3)CNC5=O)nc2)CC1]
24

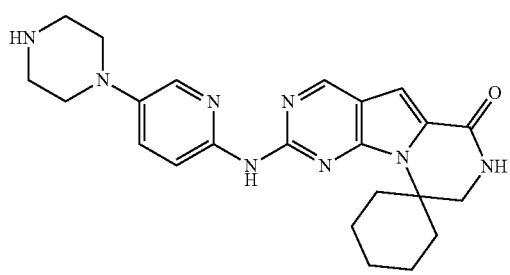 [SMILES: O=C1NCC2(CCCCC2)n2c1cc1cnc(Nc3ccc(N4CCNCC4)cn3)nc12]
25

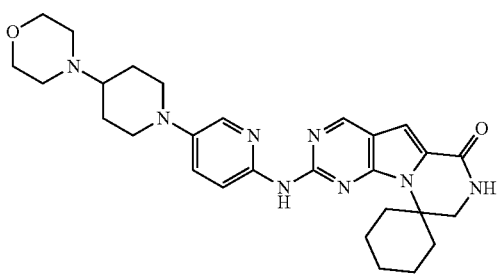 [SMILES: O=C1NCC2(CCCCC2)n2c1cc1cnc(Nc3ccc(N4CCC(N5CCOCC5)CC4)cn3)nc12]
26

Example 5. Western Blot

Whole-cell extracts of cultured cells were prepared in lysis buffer (200 mmol/L Tris, 1% Triton X-100, 5 mmol/L EDTA) with protease and phosphatase inhibitor cocktails (1:50, both from Sigma-Aldrich) after scraping from the culture plates. Protein concentration was measured using the Bradford method (Bio-Rad). Proteins were separated under denaturing conditions and blotted onto nitrocellulose membrane (Bio-Rad) using a wet transfer system (Bio-Rad). Images of blots were acquired on a Bio-Rad ChemiDoc System following incubation with SuperSignal West Dura luminol solution (Thermo Fisher Scientific). The data is shown in Table 8.

TABLE 8

| $IC_{50}$ of ER downregulation from in-cell western blot experiments | |
|---|---|
| Compound | $IC_{50}$ (nM) |
| 1 | 0.7 |
| 3 | 1.2 |
| 4 | 5.0 |
| 5 | 1.1 |
| 6 | 1.1 |
| 7 | 4.6 |

Example 6: Cell Viability of MCF7:WS8 and Cell Viability of MCF7:5C (Tamoxifen Resistant)

The DNA content of the cells was determined as previously described using a Fluorescent DNA Quantitation kit (cat. No. 170-2480; Bio-Rad Laboratories, Hercules, Calif.). Briefly, five thousand cells were plated per well in 96-well plates, and treatment with indicated concentrations of compounds was started at the same time in each well. On day 4 or 6, for MCF7:WS8 or MCF7:5C respectively, the cells in the plates were lysed and frozen at −80° C. To measure the total DNA in each well, the plates were allowed to warm to room temperature, incubated with Hoechst dye, and mixed well. The fluorescence was measured using a Synergy H4 Hybrid Multi-Mode Microplate Reader. For each analysis, six replicate wells were used and at least three independent experiments were performed.

Spheroids were plated at a concentration of 1000 cells per well in Corning® 96-well clear black round-bottom ultra-low attachment spheroid microplate and allowed to grow in the absence of treatment for 48 hours. 100 µL media was removed from each well and 100 µL 2× concentration of the treatment was added. This procedure was repeated every 2-3 days for 12 days. Analysis occurred on day 15 after plating. CellTiter-Glo® 3D Cell Viability Assay protocol was used to determine growth inhibition of the spheroids. The plates and reagent were allowed to warm to room temperature for 30 minutes. During this time, the spheroids were washed with PBS 2 times by removing 100 µL media and replacing with PBS. 100 µL from each well was then removed and replaced with 100 µL CellTiter-Glo® 3D reagent and spheroids were disrupted by pipetting. The plates were placed on a shaker for 5 minutes before allowing to equilibrate in the dark for 25 minutes. 125 µL from each well was then transferred to a white 96-well plate before recording luminescence. The data is displayed in Table 9.

TABLE 9

ERα degradation, antagonism of $E_2$ signaling, ERα relative binding affinity, and inhibition of growth of ER+ cells cultured in 3D spheroids

| Compounds | $R_1$ | ERα ICW $EC_{50}$ (nM)[a] | ERE luciferase $IC_{50}$ (nM)[b] | % growth of MCF-7:ws8 3D spheroids (rel. to vehicle)[c] | ERα binding Ki (nM)[d] | RBA % (relative to $E_2$)[e] |
|---|---|---|---|---|---|---|
| GDC-0810 | | 0.8 ± 0.07 | 11.1 ± 0.14 | 15 ± 3.00 | 0.37 ± 0.1 | 53.4 ± 15.0 |
| 5 | 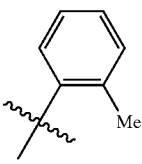 [SMILES: *c1ccccc1C] | 1.1 ± 0.05 | 16.7 ± 0.07 | 12 ± 0.02 | 1.29 ± 0.4 | 15.5 ± 4.2 |
| 1 | 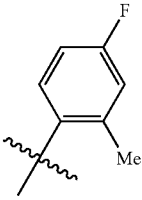 [SMILES: *c1ccc(F)cc1C] | 0.71 ± 0.05 | 8.8 ± 0.11 | 3.3 ± 0.01 | 0.65 ± 0.2 | 30.6 ± 8.7 |
| 12 | 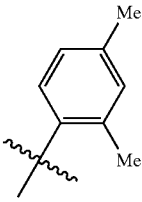 [SMILES: *c1ccc(C)cc1C] | 0.92 ± 0.05 | 4.5 ± 0.07 | 12 ± 0.01 | 0.50 ± 0.1 | 40.3 ± 4.8 |
| 11 | 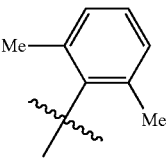 | 0.65 ± 0.06 | 4.2 ± 0.05 | 14 ± 1.00 | 2.0 ± 0.2 | 9.8 ± 0.7 |
| 21 | 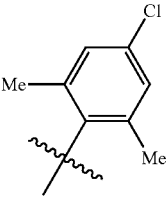 | 0.07 ± 0.13 | 2.4 ± 0.10 | 1.3 ± 0.01 | 0.57 ± 0.1 | 34.8 ± 6.2 |
| 20 | 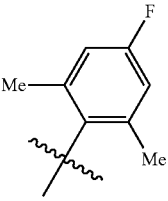 | 0.24 ± 0.16 | 3.1 ± 0.07 | 2.1 ± 0.01 | 0.73 ± 0.2 | 27.5 ± 7.0 |

[a]Potency for induction of ER degradation measured at 10 concentrations using in-cell westerns (ICW).
[b]Potency of antagonism of ERE-luciferase reporter.
[c]Spheroid growth inhibition after SERD treatment (100 nM) expressed as % of growth of DMSO vehicle control. Data show mean and s.e.m.
[d]Binding affinities calculated by the formula: Ki = (Kd[estradiol]/RBA)*100, where the Kd for estradiol is 0.2 nM.
[e]Relative binding affinity (RBA) values, determined by radioligand displacement assays expressed as $IC_{50}$ estradiol/$IC_{50}$ compound × 100 (RBA, estradiol = 100%).

Figure 1:
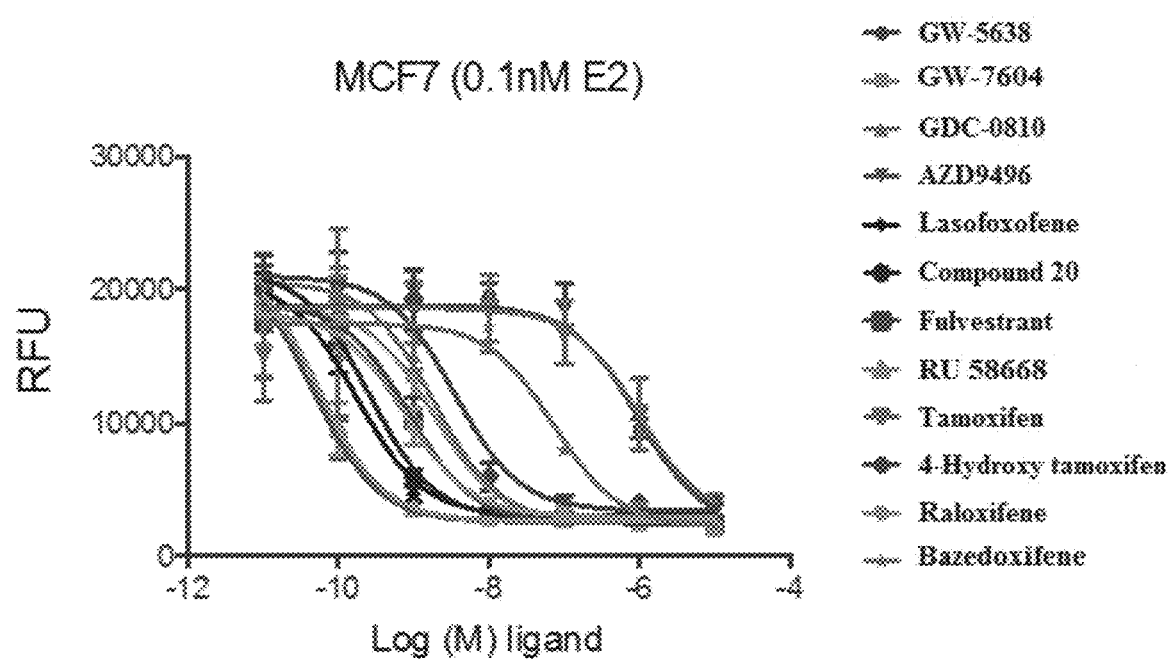
FIG. 1 is a graph of MCF-7 cell growth measured in relative fluorescent units (RFU). The graph shows cell growth in the presence of 0.1 nM of estradiol (E2) and varying concentrations of drugs which are shown in the legend to the right. The x-axis is the logarithmic concentration of drug in molarity (M). The y-axis is relative fluorescent units. The data show $IC_{50}$ curves for each compound incubated with MCF-7 cells and 0.1 nM estradiol. The $IC_{50}$ is the concentration of drug required to inhibit MCF-7 cell proliferation by 50%.

Example 7. MCF7 Cancer Cell Death in the Presence of 0.1 nM E2 and Compounds Cell death in the presence of 0.1 nM of estradiol (E2) and varying concentrations of compounds was measured in relative functional units as corrected to vehicle control. The compounds tested were Compound 20, GW-5638, GW-7604, GDC-0810, AZD9496, lasofoxofene, fulvestrant, RU 58668, tamoxifen, 4-hydroxy tamoxifen, raloxifene, and bazedoxifene. The assay was conducted 7 day proliferation assays using Hoechst dye to measure DNA content. The IC50 of GW5638 was 946 nM, the IC50 of GW-7604 was 1.81 nM, the IC50 of GDC-0810 was 1.84 nM, the IC50 of AZD949 was 0.04 nM, the IC50 of lasofoxofene was 0.17 nM, the IC50 of Compound 20 was 0.26 nM, the IC50 of fulvestrant was 0.86 nM, the IC50 of RU 58668 was 0.052 nM, the IC50 of tamoxifen was 985 nM, the IC50 of 4-hydroxytamoxifen was 3.46 nM, the IC50 of raloxifene was 0.77 nM, and the IC50 of bazedoxifene was 72 nM. As measured in this assay, Compound 20 is nearly 4 times more potent than fulvestrant. This data is shown in FIG. 1.

Figure 2A:
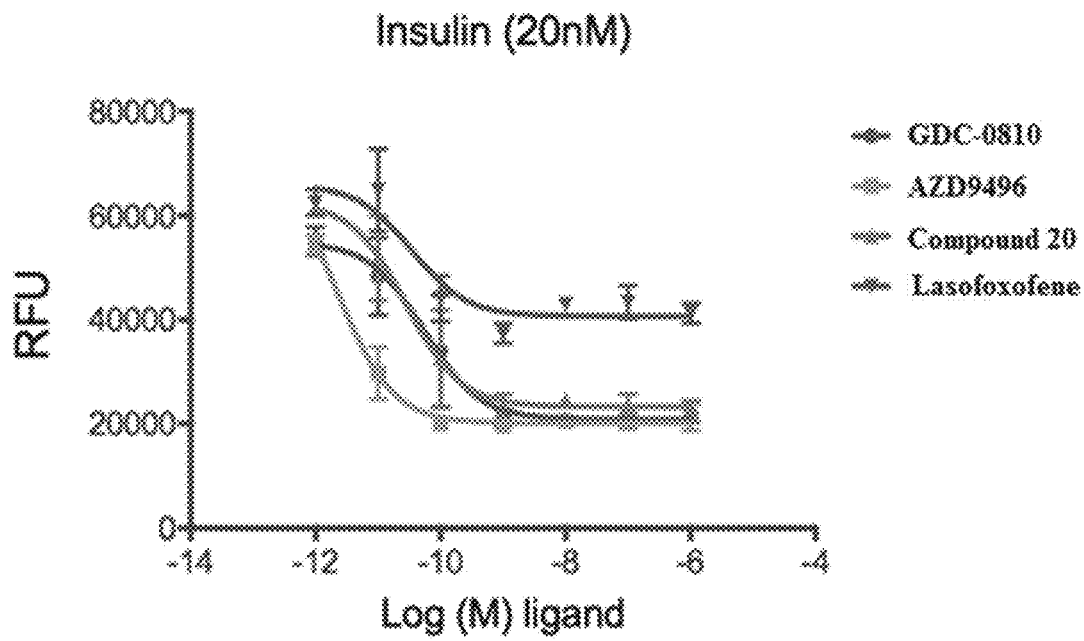
FIG. 2A is a graph of MCF-7 cell growth measured in relative fluorescent units (RFU). The graph shows cell growth in the presence of 20 nM insulin and varying concentrations of GDC-0810, AZD9496, Compound 20, and lasofoxofene (LASO). The legend to the right identifies these drugs. The x-axis is the logarithmic concentration of drug in molarity (M). The y-axis is relative fluorescent units. The data show $IC_{50}$ curves for each compound incubated with MCF-7 cells and 20 nM insulin. The $IC_{50}$ is the concentration of drug required to inhibit MCF-7 cell proliferation by 50%.
Figure 2B:
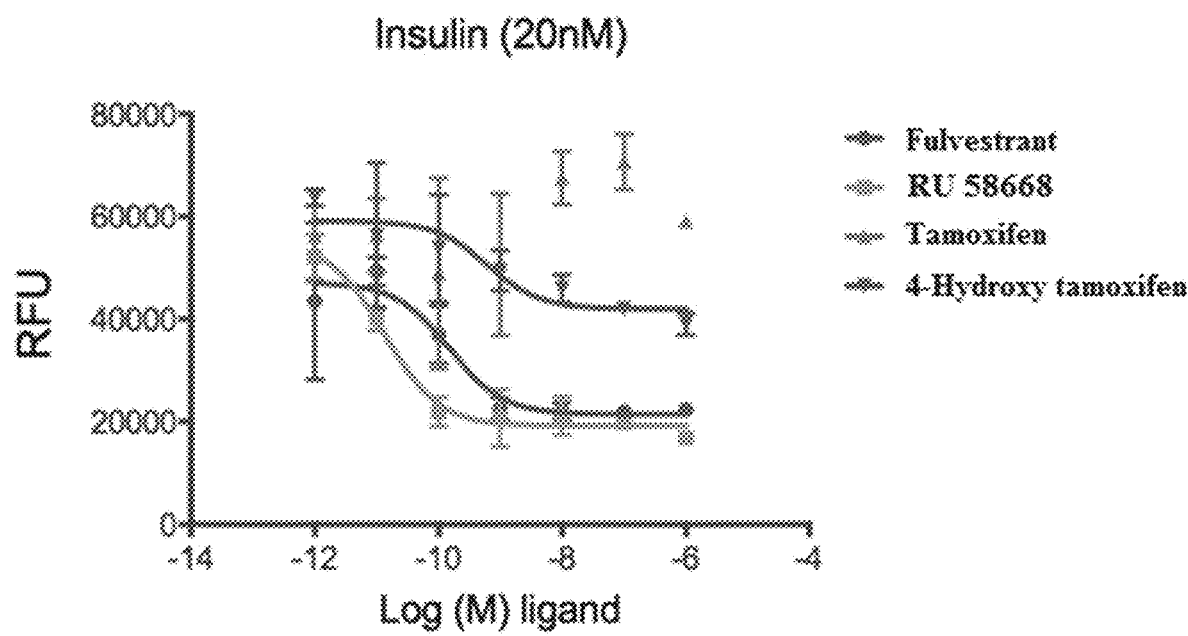
FIG. 2B is a graph of MCF-7 cell growth measured in relative fluorescent units (RFU). The graph shows cell growth in the presence of 20 nM insulin and varying concentrations of fulvestrant, a fulvestrant analog, tamoxifen, and 4-hydroxytamoxifene (4OHT). The legend to the right identifies these drugs. The x-axis is the logarithmic concentration of drug in molarity (M). The y-axis is relative fluorescent units. The data show $IC_{50}$ curves for each compound incubated with MCF-7 cells and 20 nM insulin. The $IC_{50}$ is the concentration of drug required to inhibit MCF-7 cell proliferation by 50%.
Figure 2C:
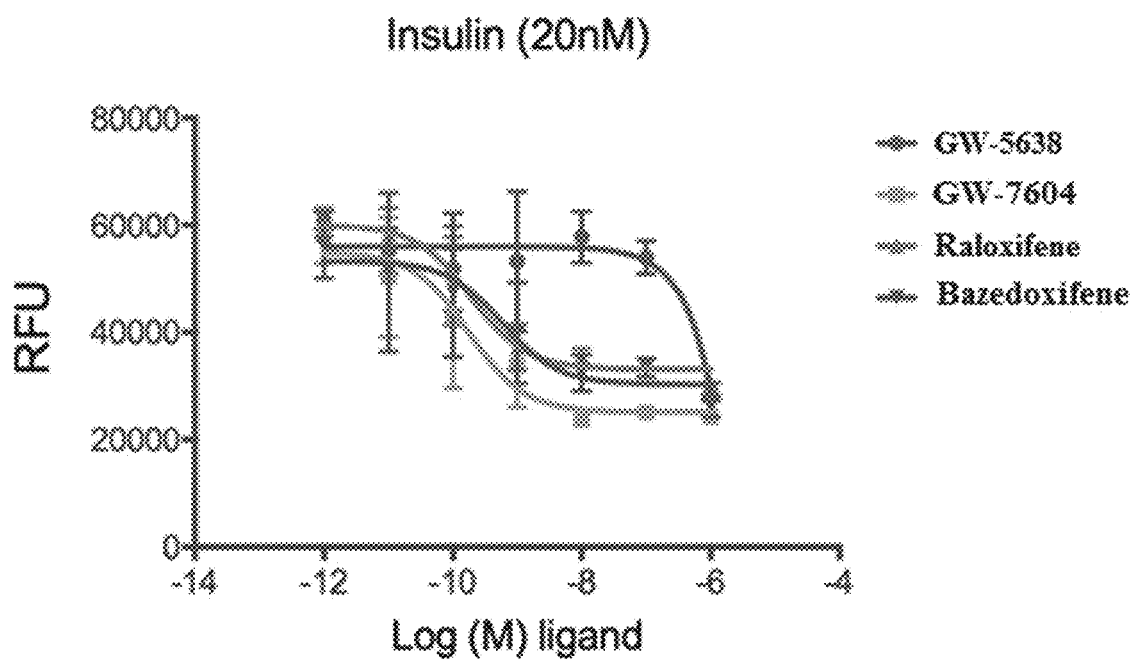
FIG. 2C is a graph of MCF-7 cell growth measured in relative fluorescent units (RFU). The graph shows cell growth in the presence of 20 nM insulin and varying concentrations of GW-5638, GW-7604, raloxifene, and bazedoxifene. The legend to the right identifies these drugs. The x-axis is the logarithmic concentration of drug in molarity (M). The y-axis is relative fluorescent units. The data show $IC_{50}$ curves for each compound incubated with MCF-7 cells and 20 nM insulin. The $IC_{50}$ is the concentration of drug required to inhibit MCF-7 cell proliferation by 50%.

Example 8. MCF7 Cancer Cell Death in the Presence of 20 nM Insulin and Compounds Cell death in the presence of 20 nM insulin and varying concentrations of compounds was measured in relative functional units as corrected to vehicle control. The compounds tested were Compound 20, GW-5638, GW-7604, GDC-0810, AZD9496, lasofoxofene, fulvestrant, RU 58668, tamoxifen, 4-hydroxy tamoxifen, raloxifene, and bazedoxifene. The assay was conducted 7 day proliferation assays using Hoechst dye to measure DNA content. The data shows that Compound 20 inhibits insulin driven proliferation more effectively than bazedoxifene, raloxifene, tamoxifen, 4-hydroxytamoxifen, and lasofoxofene. The IC50 of GDC-0810 was 55 pM, the IC50 of AZD9496 was 2 pM, the IC50 of Compound 20 was 28 pM, the IC50 of fulvestrant was 149 pM, and the IC50 of RU 58668 was 13 pM. This data is shown in FIG. 2A, FIG. 2B, and FIG. 2C.

Example 9. In Cell Western Blot in the Presence of Compounds

Figure 3A:
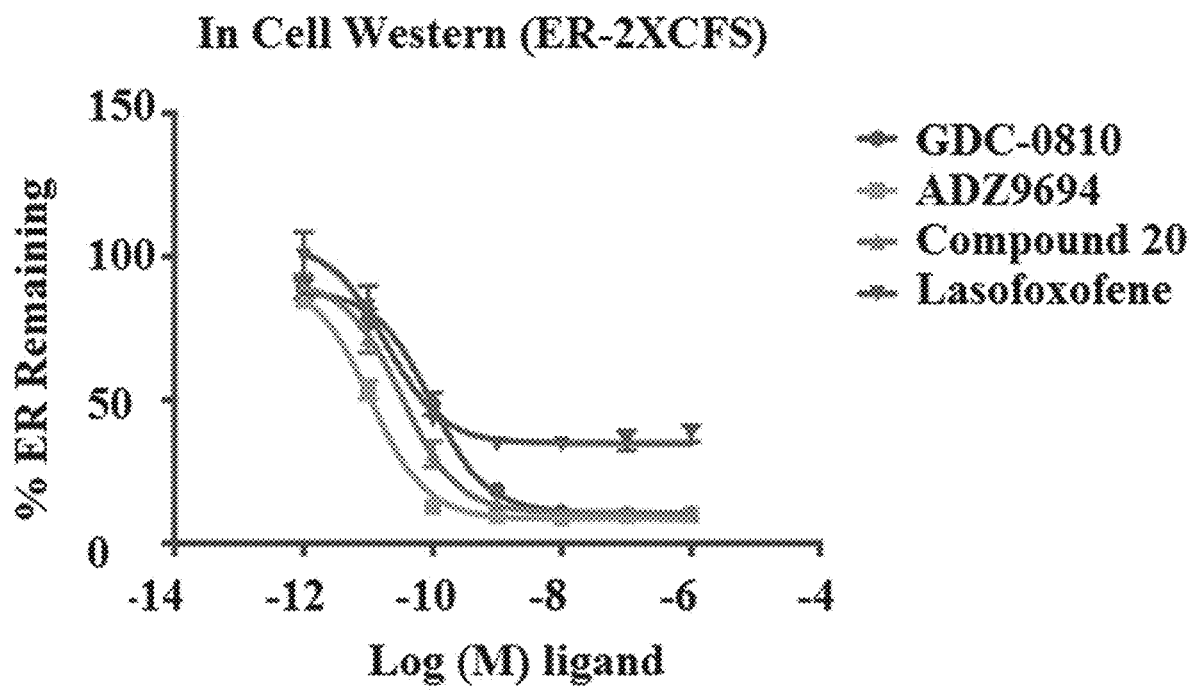
FIG. 3A is a graph showing the degradation of estrogen receptor (ER) as a function of SERM/SERD concentrations. The legend to the right identifies these SERMS and SERDS which include GDC-0810, ADZ9694, Compound 20, and lasofoxofene. The x-axis is the logarithmic concentration of drug in molarity (M). The y-axis is % ER remaining after drug incubation which was quantified by western blot analysis and normalized to an untreated control. The graph shows an $IC_{50}$ dose-dependent response curve for each drug and their effect on ER degradation. The $IC_{50}$ is the concentration of drug required to reduce the % ER remaining to 50%.
Figure 3B:
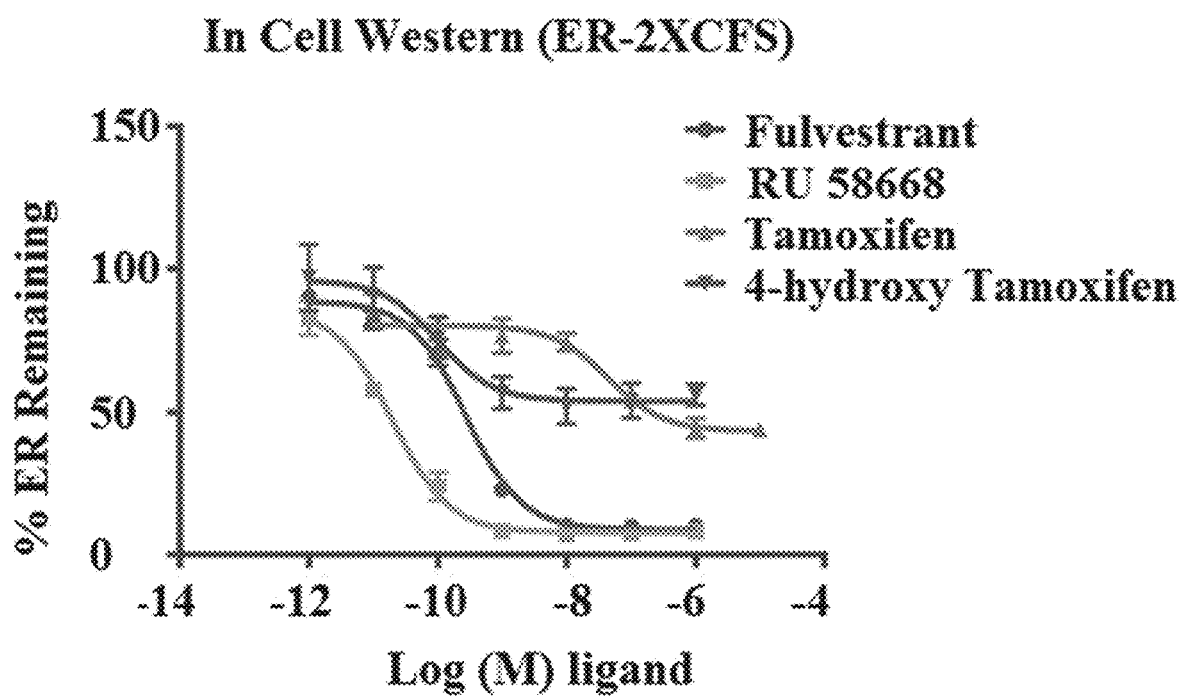
FIG. 3B is a graph showing the degradation of estrogen receptor (ER) as a function of SERM/SERD concentrations. The legend to the right identifies these SERMS and SERDS which include fulvestrant, a fulvestrant analog, tamoxifen, and 4-hydroxytamoxifene (4OHT). The x-axis is the logarithmic concentration of drug in molarity (M). The y-axis is % ER remaining after drug incubation which was quantified by western blot analysis and normalized to an untreated control. The graph shows an $IC_{50}$ dose-dependent response curve for each drug and their effect on ER degradation. The $IC_{50}$ is the concentration of drug required to reduce the % ER remaining to 50%.
Figure 3C:
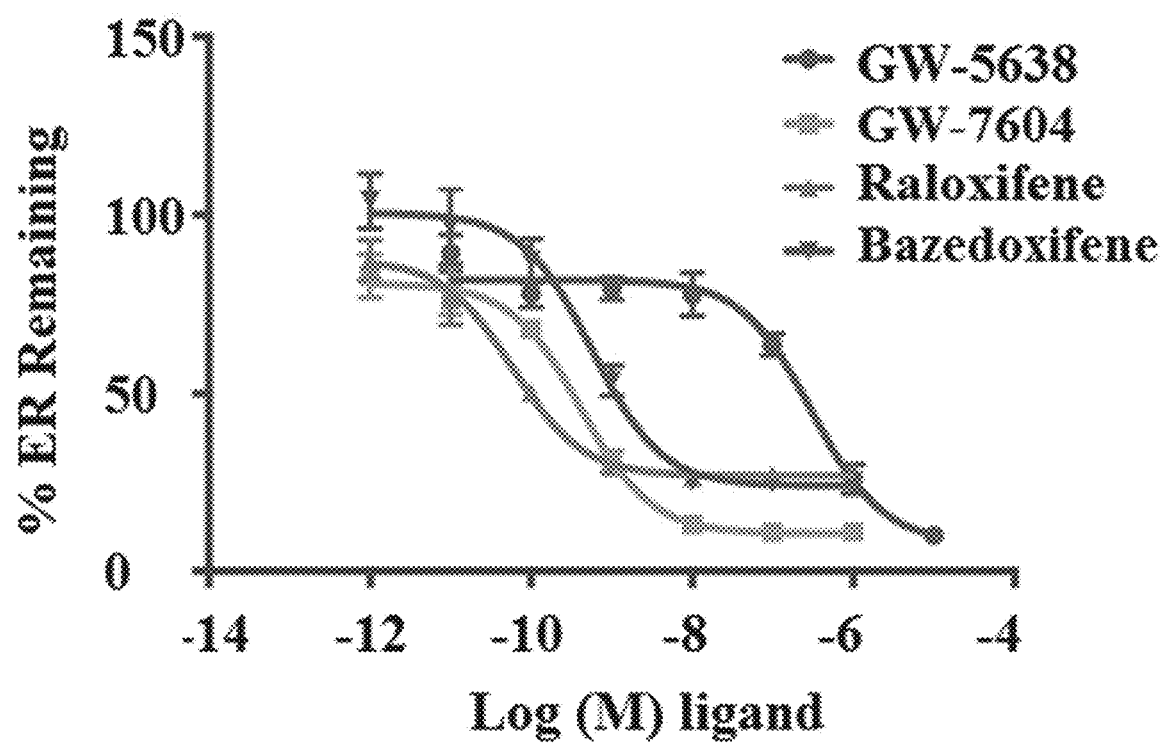
FIG. 3C is a graph showing the degradation of estrogen receptor (ER) as a function of SERM/SERD concentrations. The legend to the right identifies these SERMS and SERDS which include GW-5638, GW-7604, raloxifene, and bazedoxifene. The x-axis is the logarithmic concentration of drug in molarity (M). The y-axis is % ER remaining after drug incubation which was quantified by western blot analysis and normalized to an untreated control. The graph shows an $IC_{50}$ dose-dependent response curve for each drug and their effect on ER degradation. The $IC_{50}$ is the concentration of drug required to reduce the % ER remaining to 50%.

Estrogen receptor degradation was measured in MCF7 cells grown in 2XCFS cells by western blot analysis. The compounds tested were Compound 20, GW-5638, GW-7604, GDC-0810, AZD9496, lasofoxofene, fulvestrant, RU 58668, tamoxifen, 4-hydroxy tamoxifen, raloxifene, and bazedoxifene. The IC50 of Compound 20 was 33 pM, the IC50 of GDC-0810 was 94 pM, the IC50 of AZD9496 was 11 pM, the IC50 of GW5638 was 310 nM, and the IC50 of GW-7604 was 420 pM. This data is shown in FIG. 3A, FIG. 3B, and FIG. 3C.

Figure 4:
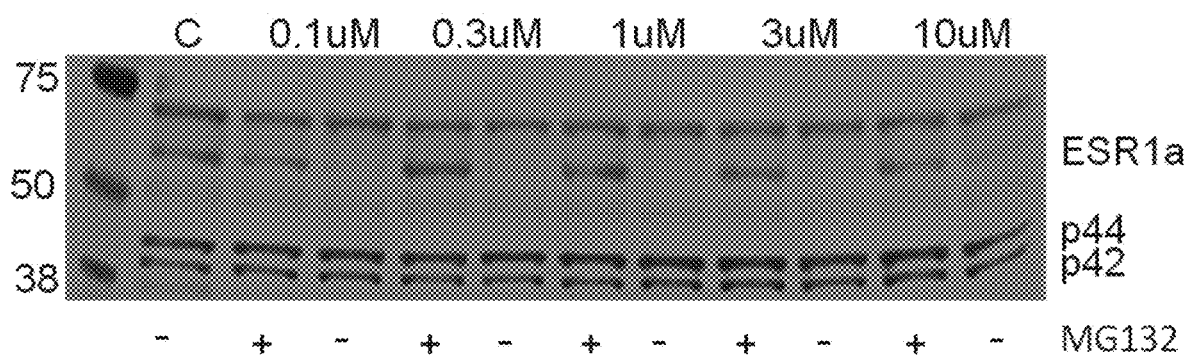
FIG. 4 is a western blot that quantifies the amount of estrogen receptor (ER) remaining after incubation with Compound 20. The top numbers are the concentrations of Compound 20 used (micromolar).

The western blot in FIG. 4 shows that the degradation of the estrogen receptor (ESR1a) in the presence of Compound 20 is dependent on the absence of MG132. G1T48 was dosed in MCF7 cells in the presence or absence of MG132, a proteasome pathway inhibitor. Cells were harvested and lysed for total protein in RIPA buffer containing protease and phosphatase inhibitors. Protein concentrations were determined using standard BCA protein assay (Pierce) following manufacturer's recommendations. Proteins were then separated using Invitrogen's NuPage gel electrophoresis system and transferred onto a nitrocellulose membrane. The membrane was then incubated with primary antibodies (ESR1-a and p44/p42) followed by washes and then incubated in secondary antibodies to differentiate both protein species. Membranes were then washed and imaged using LI-COR Odyssey Fc.

Example 10. SKBR3 (Wild Type Estrogen Receptor) Cell Death

Figure 5A:
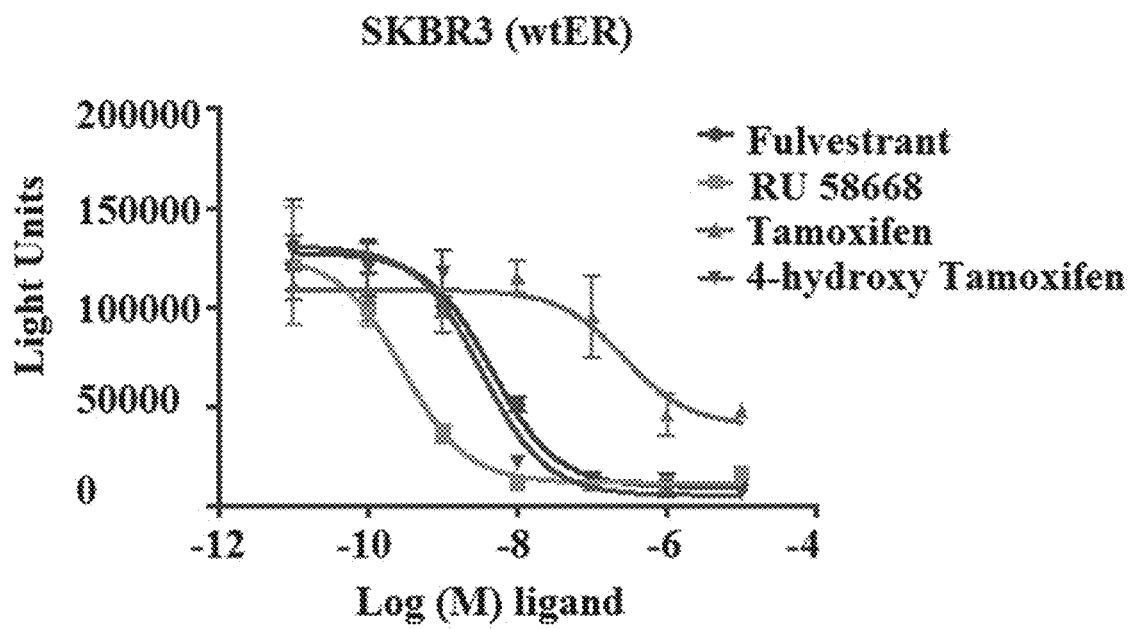
FIG. 5A is a graph showing the inhibition of estrogen receptor (ER)-driven transcription in SKBR3 cells as a function of drug concentration. The cells express wild-type ER (wtER). SKBR3 cells were incubated with varying concentrations of fulvestrant, an analog of fulvestrant, tamoxifene, and 4-hydroxytamoxifene (4OHT). These drugs are identified by the legend on the right. The x-axis is the logarithmic concentration of drug in molarity (M). The y-axis is light units that reflect the intensity of ER transcription. The data show $IC_{50}$ curves for each compound incubated with SKBR3 cells. The $IC_{50}$ is the concentration of drug required to inhibit ER transcription by 50%.
Figure 5B:
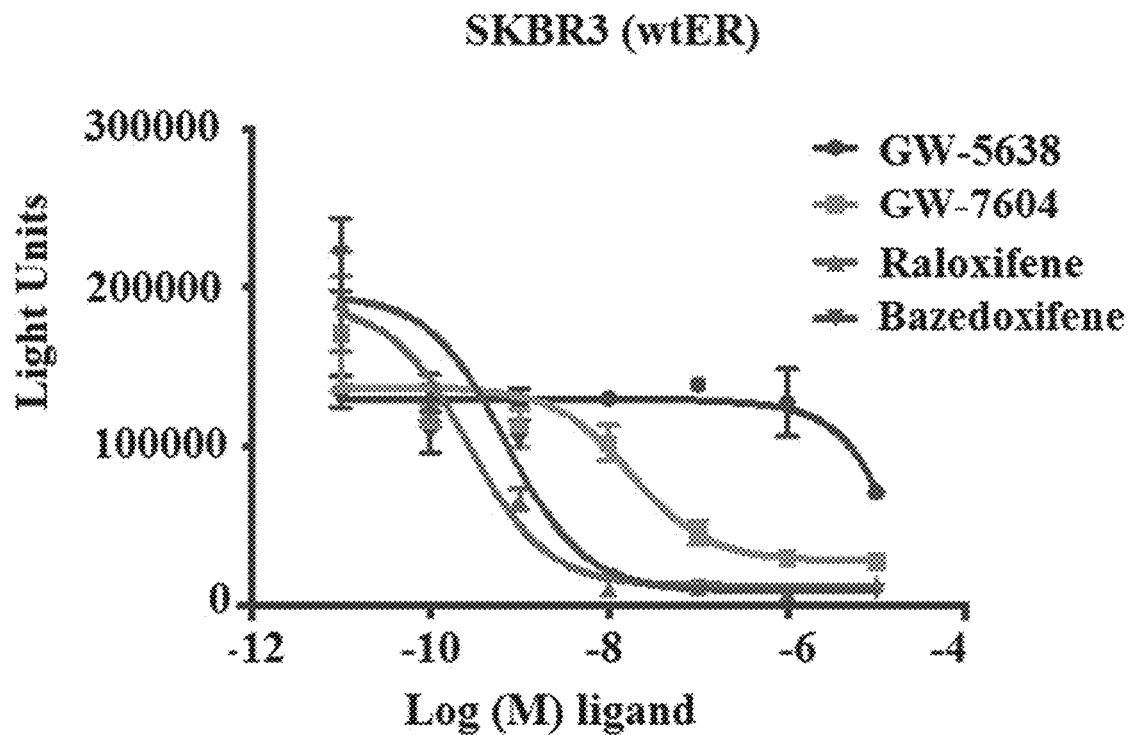
FIG. 5B is a graph showing the inhibition of estrogen receptor (ER)-driven transcription in SKBR3 cells as a function of drug concentration. The cells express wild-type ER (wtER). SKBR3 cells were incubated with varying concentrations of GW-5638, GW-7604, raloxifene, and bazedoxifene. These drugs are identified by the legend on the right. The x-axis is the logarithmic concentration of drug in molarity (M). The y-axis is light units that reflect the intensity of ER transcription. The data show IC50 curves for each compound incubated with SKBR3 cells. The IC50 is the concentration of drug required to inhibit ER transcription by 50%.
Figure 5C:
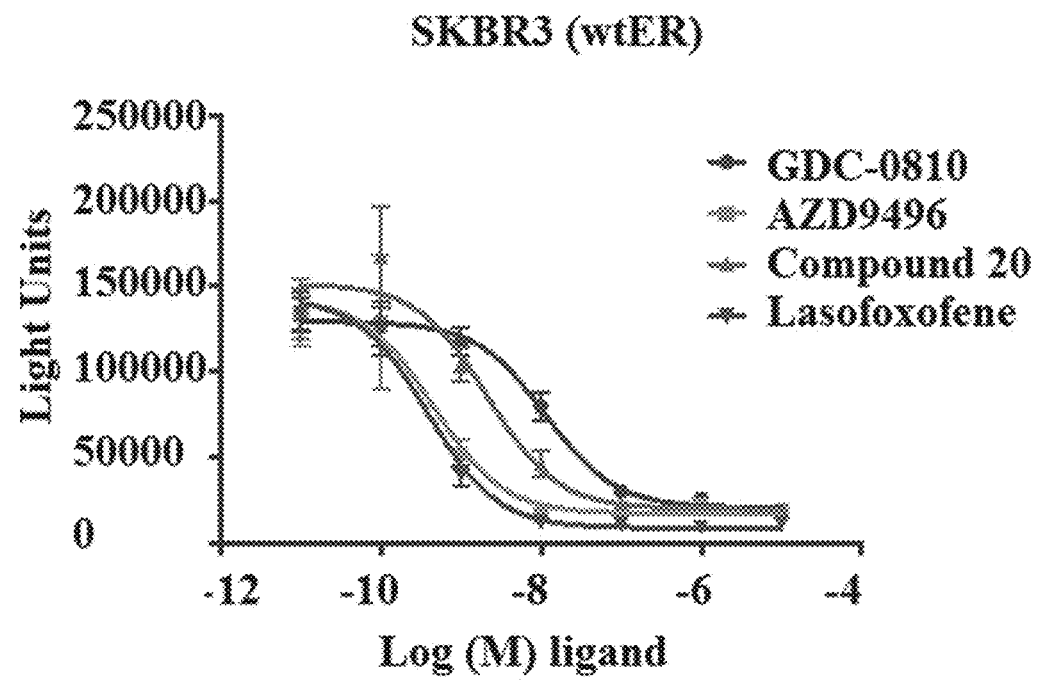
FIG. 5C is a graph showing the inhibition of estrogen receptor (ER)-driven transcription in SKBR3 cells as a function of drug concentration. The cells express wild-type ER (wtER). SKBR3 cells were incubated with varying concentrations of GDC-0810, AZD9496, Compound 20, and lasofoxofene (LASO). These drugs are identified by the legend on the right. The x-axis is the logarithmic concentration of drug in molarity (M). The y-axis is light units that reflect the intensity of ER transcription. The data show IC50 curves for each compound incubated with SKBR3 cells. The IC50 is the concentration of drug required to inhibit ER transcription by 50%.

SKBR3 (WT ER) cell death at varying concentrations of compounds was measured in light units as corrected to vehicle control. The compounds tested were Compound 20, GW-5638, GW-7604, GDC-0810, AZD9496, lasofoxofene, fulvestrant, RU 58668, tamoxifen, 4-hydroxy tamoxifen, raloxifene, and bazedoxifene. In the assay the IC50 of fulvestrant was 4.48 nM, the IC50 of RU 58668 was 0.29 nM, the IC50 of tamoxifen was 267 nM, the IC50 of 4-hydroxytamoxifen 3.25 nM, the IC50 of GW-7604 was 17.9 nM, the IC50 of raloxifene was 0.27 nM, the IC50 of bazedoxifene was 0.71 nM, the IC50 of GDC-0810 was 11.3 nM, the IC50 of AZD9496 was 0.45 nM, the IC50 of Compound 20 was 2.14 nM, and the IC50 of lasofoxofene was 0.38 nM. This data is shown in FIG. 5A, FIG. 5B, and FIG. 5C. The SKBR3 cells had wild type estrogen receptor.

Example 11. SKBR3 (D538G Mutated Estrogen Receptor) Cell Death

Figure 6A:
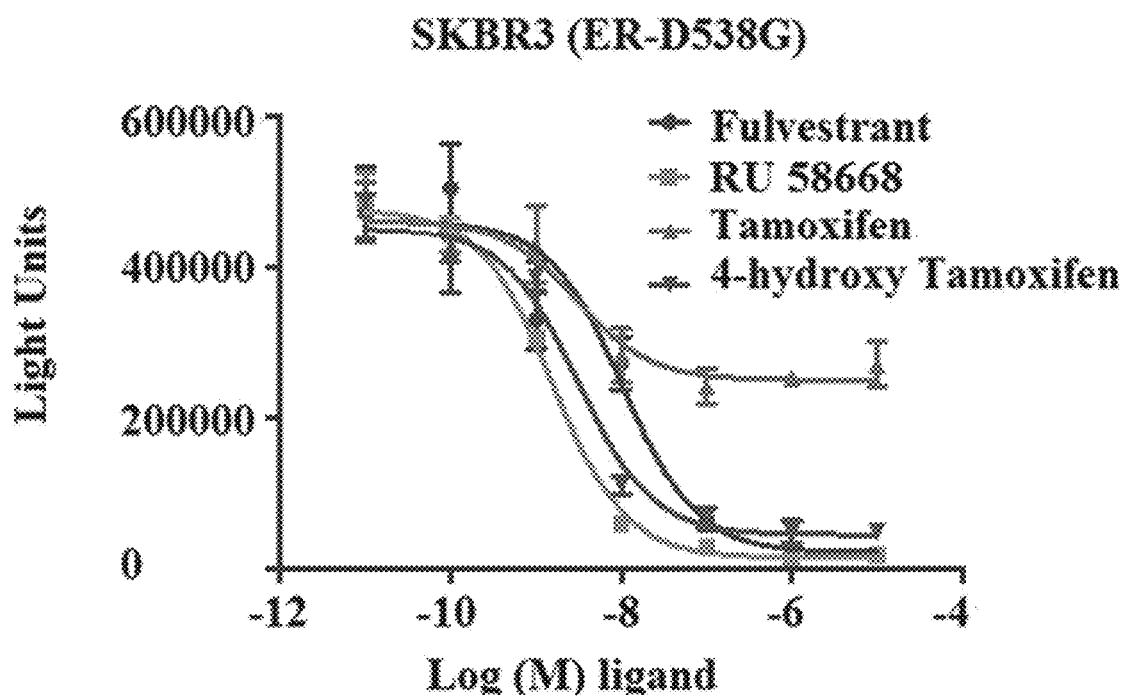
FIG. 6A is a graph showing the inhibition of estrogen receptor (ER)-driven transcription in SKBR3 cells as a function of drug concentration. The cells express mutant ER (D538G). SKBR3 cells were incubated with varying concentrations of fulvestrant, a fulvestrant analog, tamoxifen (Tam), and 4-hydroxytamoxifene (4OHT). These drugs are identified by the legend on the right. The x-axis is the logarithmic concentration of drug in molarity (M). The y-axis is light units that reflect the intensity of ER transcription. The data show IC50 curves for each compound incubated with SKBR3 cells. The IC50 is the concentration of drug required to inhibit ER transcription by 50%.
Figure 6B:
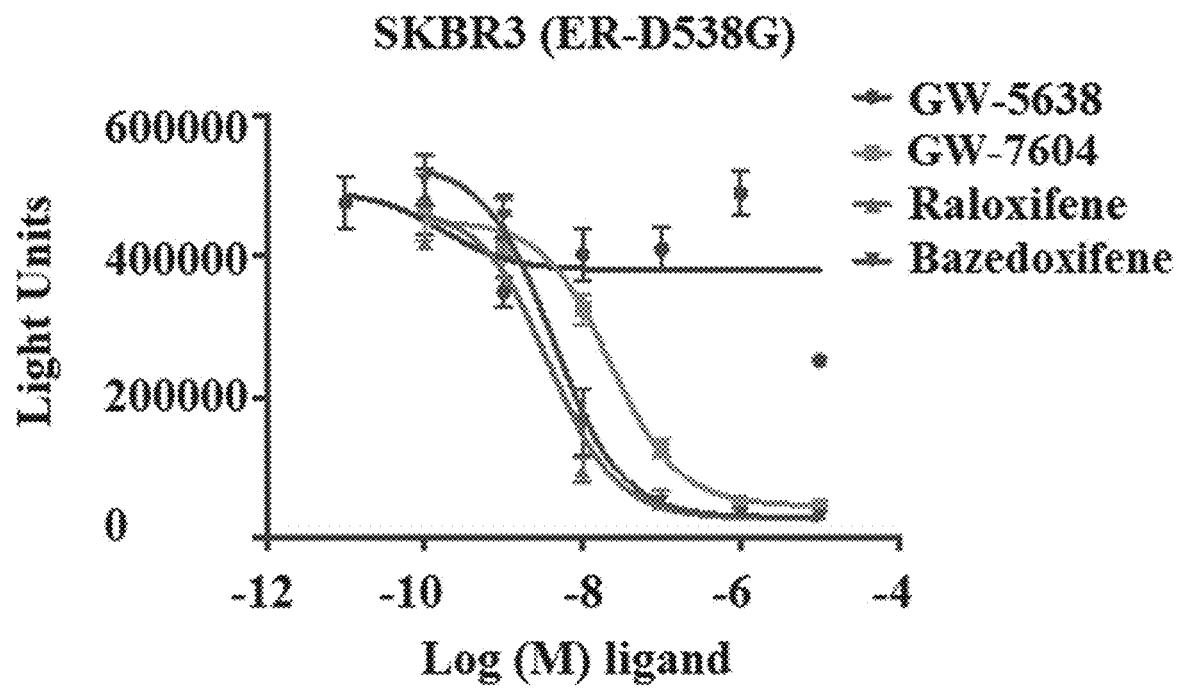
FIG. 6B is a graph showing the inhibition of estrogen receptor (ER)-driven transcription in SKBR3 cells as a function of drug concentration. The cells express mutant ER (D538G). SKBR3 cells were incubated with varying concentrations of GW-5638, GW-7604, raloxifene (Ralox), and bazedoxifene. These drugs are identified by the legend on the right. The x-axis is the logarithmic concentration of drug in molarity (M). The y-axis is light units that reflect the intensity of ER transcription. The data show IC50 curves for each compound incubated with SKBR3 cells. The $IC_{50}$ is the concentration of drug required to inhibit ER transcription by 50%.
Figure 6C:
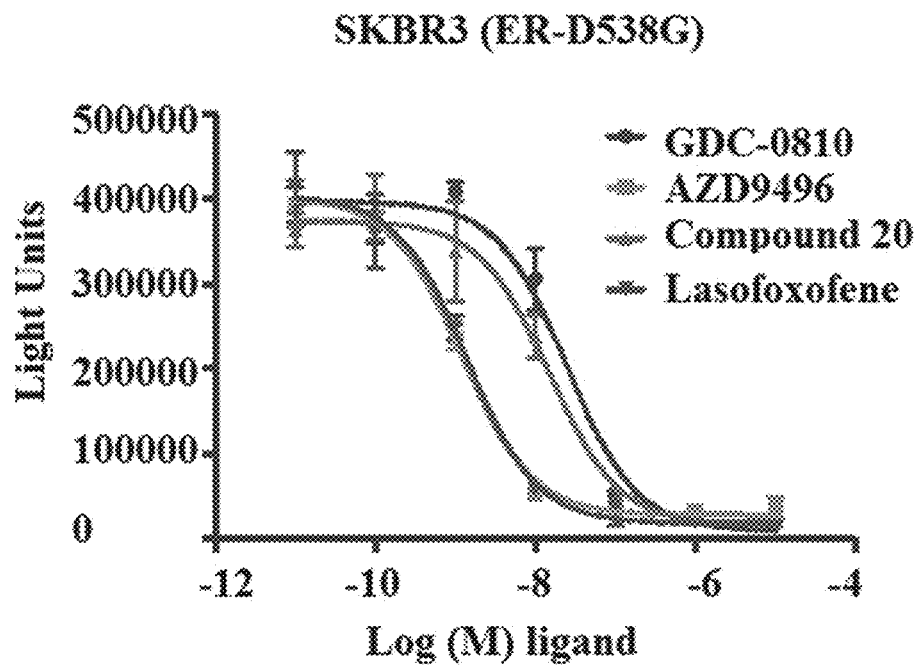
FIG. 6C is a graph showing the inhibition of estrogen receptor (ER)-driven transcription in SKBR3 cells as a function of drug concentration. The cells express mutant ER (D538G). SKBR3 cells were incubated with varying concentrations of GDC-0810, AZD9496, Compound 20, and lasofoxofene (LASO). These drugs are identified by the legend on the right. The x-axis is the logarithmic concentration of drug in molarity (M). The y-axis is light units that reflect the intensity of ER transcription. The data show IC50 curves for each compound incubated with SKBR3 cells. The IC50 is the concentration of drug required to inhibit ER transcription by 50%.

SKBR3 (D538G ER) cell death at varying concentrations of compounds was measured in light units as corrected to vehicle control. The compounds tested were Compound 20, GW-5638, GW-7604, GDC-0810, AZD9496, lasofoxofene, fulvestrant, RU 58668, tamoxifen, 4-hydroxy tamoxifen, raloxifene, and bazedoxifene. In the assay the IC50 of fulvestrant was 10.5 nM, the IC50 of RU 58668 was 1.56 nM, the IC50 of tamoxifen was 2.99 nM, the IC50 of 4-hydroxytamoxifen 3.11 nM, the IC50 of GW-5638 was 0.17 nM, the IC50 of GW-7604 was 22.6 nM, the IC50 of raloxifene was 3.73 nM, the IC50 of bazedoxifene was 4.27 nM, the IC50 of GDC-0810 was 24.5 nM, the IC50 of AZD9496 was 1.20 nM, the IC50 of Compound 20 was 14.7 nM, and the IC50 of lasofoxofene was 1.39 nM. This data is shown in FIG. 6A, FIG. 6B, and FIG. 6C. The SKBR3 cells had D538G mutated estrogen receptor.

Example 12. SKBR3 (Y537S Mutated Estrogen Receptor) Cell Death

Figure 7A:
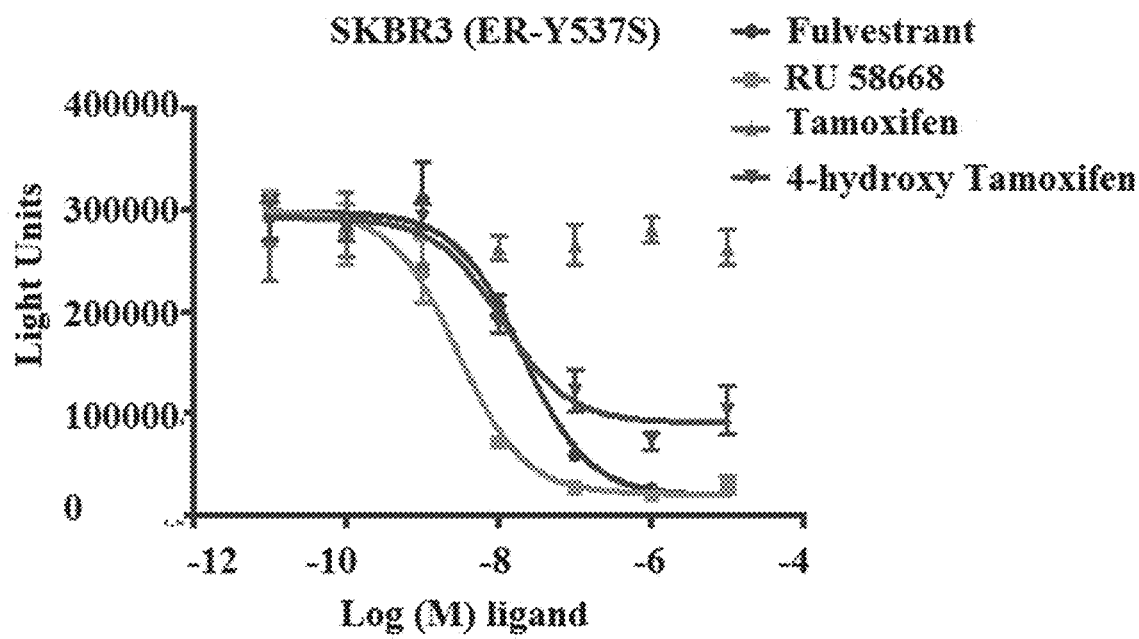
FIG. 7A is a graph showing the inhibition of estrogen receptor (ER)-driven transcription in SKBR3 cells as a function of drug concentration. The cells express mutant ER (Y537S). SKBR3 cells were incubated with varying concentrations of fulvestrant, a fulvestrant analog, tamoxifen (Tam), and 4-hydroxytamoxifene (4OHT). These drugs are identified by the legend on the right. The x-axis is the logarithmic concentration of drug in molarity (M). The y-axis is light units that reflect the intensity of ER transcription. The data show $IC_{50}$ curves for each compound incubated with SKBR3 cells. The $IC_{50}$ is the concentration of drug required to inhibit ER transcription by 50%.
Figure 7B:
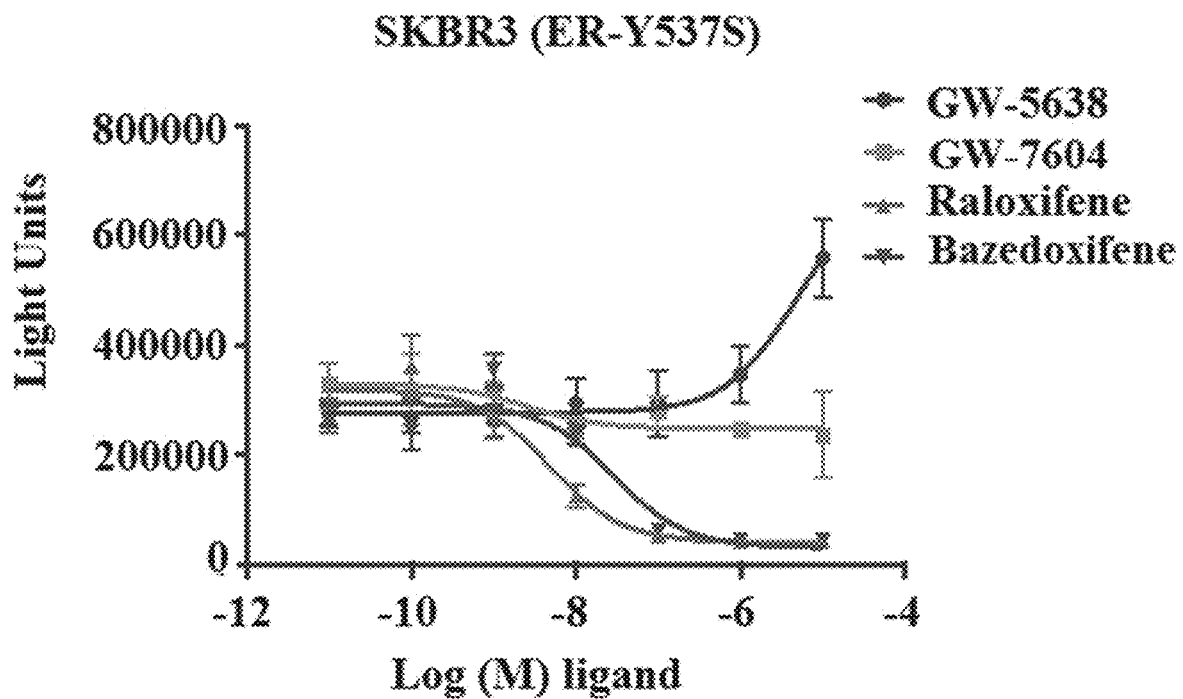
FIG. 7B is a graph showing the inhibition of estrogen receptor (ER)-driven transcription in SKBR3 cells as a function of drug concentration. The cells express mutant ER (Y537S). SKBR3 cells were incubated with varying concentrations of GW-5638, GW-7604, raloxifene (Ralox), and bazedoxifene. These drugs are identified by the legend on the right. The x-axis is the logarithmic concentration of drug in molarity (M). The y-axis is light units that reflect the intensity of ER transcription. The data show $IC_{50}$ curves for each compound incubated with SKBR3 cells. The $IC_{50}$ is the concentration of drug required to inhibit ER transcription by 50%.
Figure 7C:
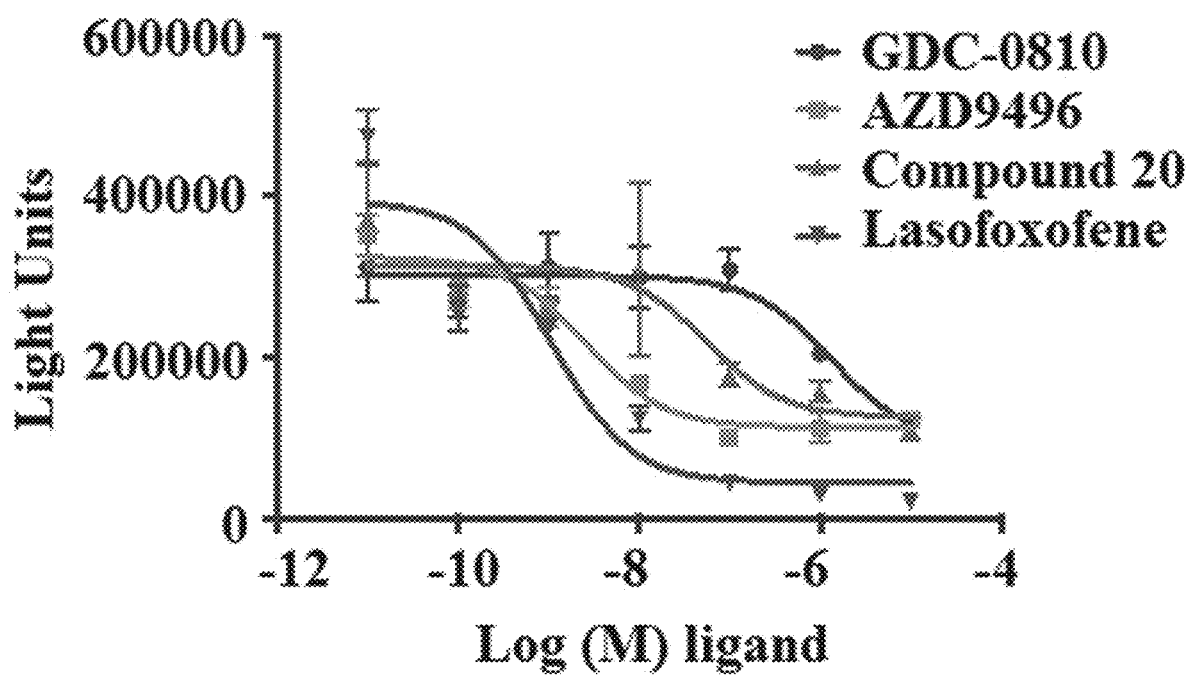
FIG. 7C is a graph showing the inhibition of estrogen receptor (ER)-driven transcription in SKBR3 cells as a function of drug concentration. The cells express mutant ER (Y537S). SKBR3 cells were incubated with varying concentrations of GDC-0810, AZD9496, Compound 20, and lasofoxofene (LASO). These drugs are identified by the legend on the right. The x-axis is the logarithmic concentration of drug in molarity (M). The y-axis is light units that reflect the intensity of ER transcription. The data show $IC_{50}$ curves for each compound incubated with SKBR3 cells. The $IC_{50}$ is the concentration of drug required to inhibit ER transcription by 50%.

SKBR3 (Y537S ER) cell death at varying concentrations of compounds was measured in light units as corrected to vehicle control. The compounds tested were Compound 20, GW-5638, GW-7604, GDC-0810, AZD9496, lasofoxofene, fulvestrant, RU 58668, tamoxifen, 4-hydroxy tamoxifen, raloxifene, and bazedoxifene. In the assay the IC50 of fulvestrant was 20.2 nM, the IC50 of RU 58668 was 2.87 nM, the IC50 of 4-hydroxytamoxifen 11.0 nM, the IC50 of GW-5638 was 4.91 uM, the IC50 of GW-7604 was 2.56 nM, the IC50 of raloxifene was 4.79 nM, the IC50 of bazedoxifene was 29.0 nM, the IC50 of GDC-0810 was 1.30 uM, the IC50 of AZD9496 was 2.57 nM, the IC50 of Compound 20 was 56.0 nM, and the IC50 of lasofoxofene was 1.07 nM. This data is shown in FIG. 7A, FIG. 7B, and FIG. 7C. The SKBR3 cells had Y537S mutated estrogen receptor.

Figure 8:
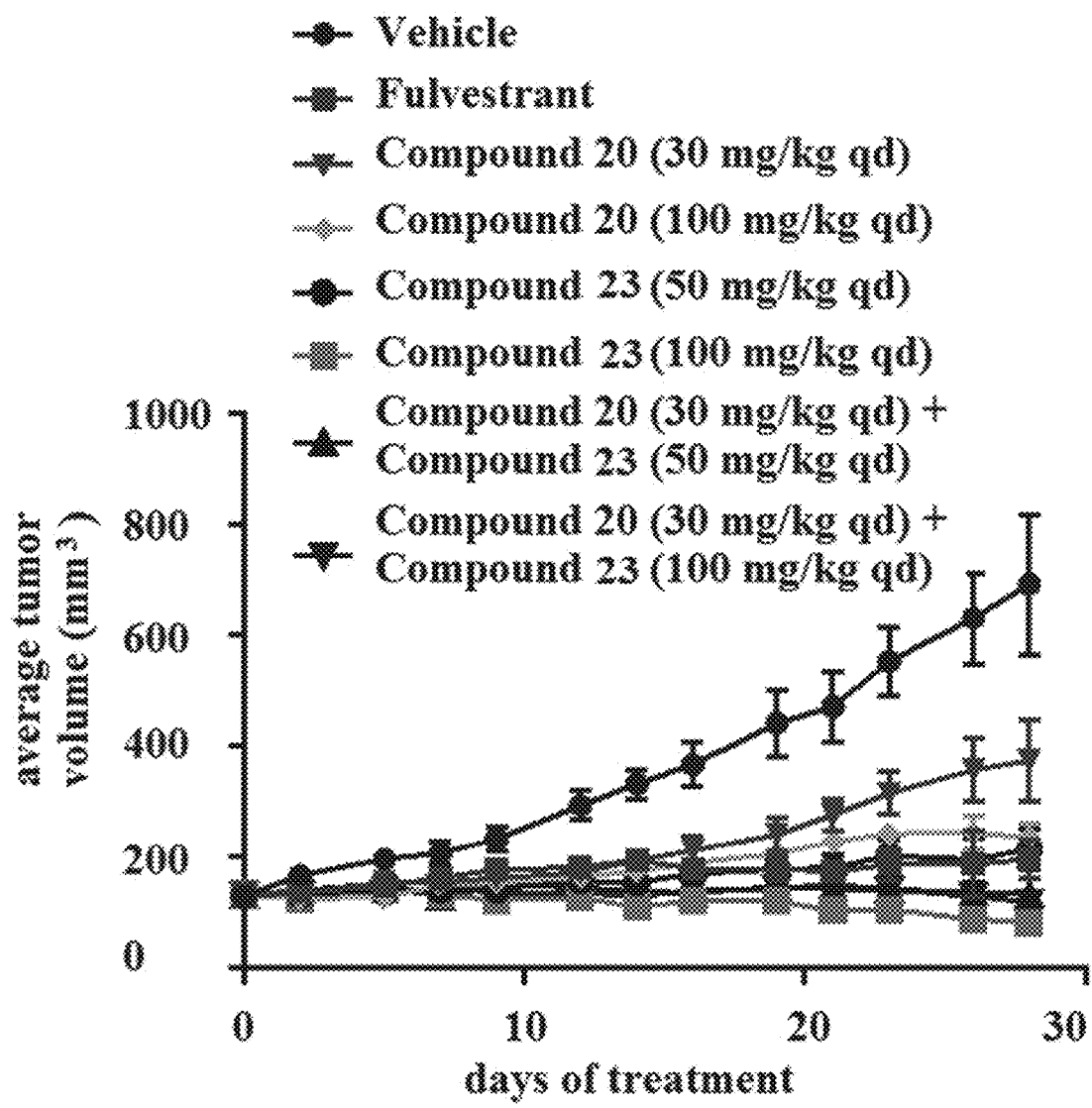
FIG. 8 is a graph of average tumor volume following treatment with various compounds in a Tamoxifen resistant ER+ breast cancer model. The y-axis is average tumor volume measured in $mm^3$. The x-axis is time measured in days.
Figure 9:
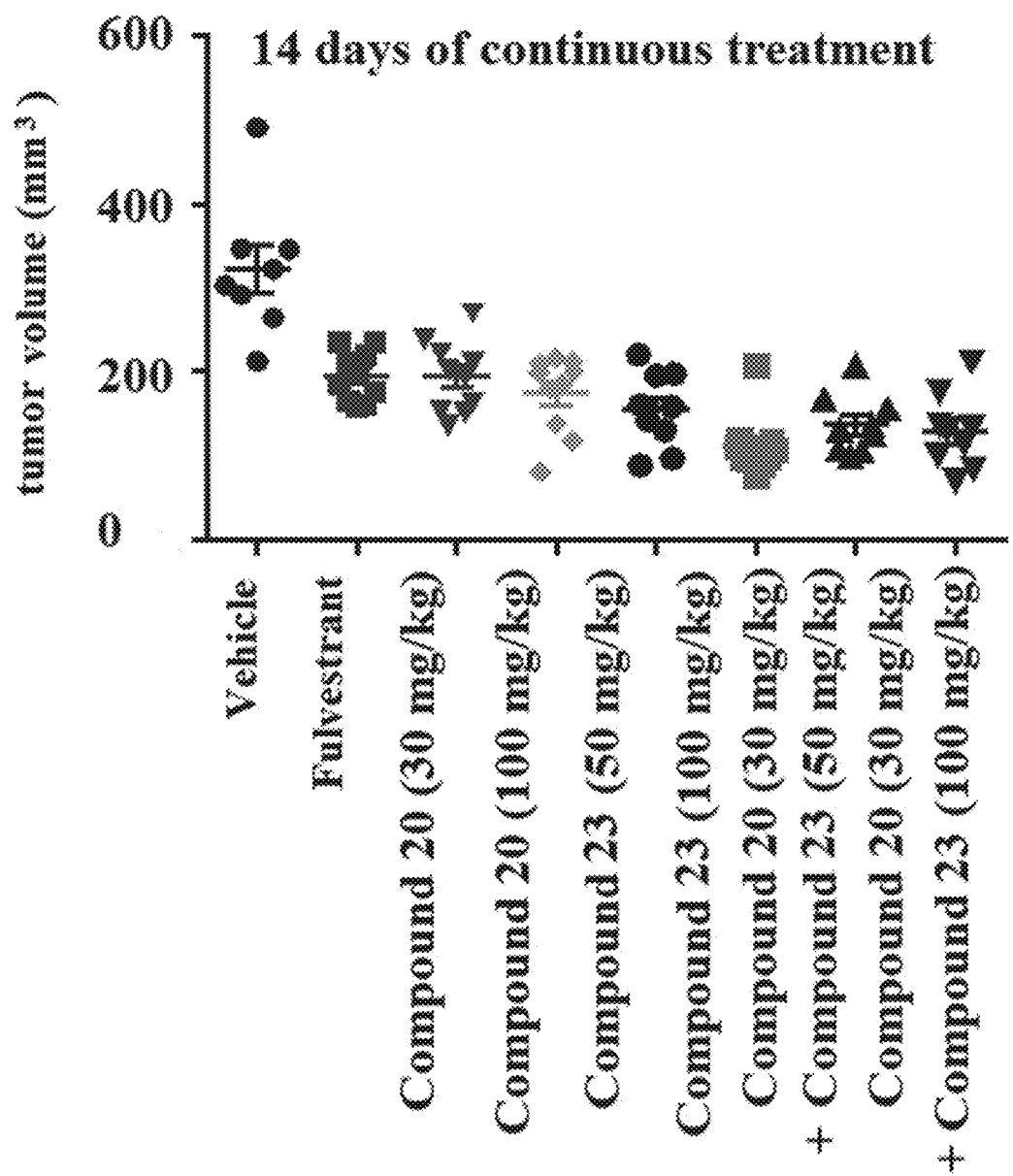
FIG. 9 is a graph of tumor volume following 14 days of continuous treatment with various compounds in a Tamoxifen resistant ER+ breast cancer model. The y-axis is tumor volume measured in $mm^3$. The x-axis is the compound administered continuously for 14 days.

Example 13. Compound 20 Increases Activity of Compound 23 in MCF7 Tam-Stimulated Tumors MCF7:TamR tumor cells were implanted into tamoxifen-treated mice. When Tam-stimulated tumors attained ~0.1 cm³ tumor volume, animals were randomized (7-9 mice per group) to receive continued tamoxifen treatment as well as vehicle or SERD fulvestrant (5 mg/mouse 1× weekly i.m.), the SERD Compound 20 (30 or 100 mg/kg/day, p.o.) and/or the CDK4/6 inhibitor Compound 23 (50 mg/kg or 100 mg/kg/day, p.o.). Tumor growth for each group is presented as average tumor volume+/−SEM per study arm. As shown in FIG. 8, as continuous treatment was given over the course of approximately 30 days, the combination of 50 mg/kg of Compound 23 and 30 mg/kg of Compound 20 was more effective in decreasing tumor volume than 50 mg/kg of CDK4/6 inhibitor Compound 23 alone and 30 mg/kg of Compound 20 alone. FIG. 9 is a depiction of treatment over the first 14 days of continuous dosing, where the same effect was observed; the combination of Compound 23 (50 mg/kg) and Compound 20 (30 mg/kg) decreased tumor more effectively than both Compound 23 and Compound 20 at those same dosages administered alone.

Example 14. Comparison of Compound 20 to GDC-0810, Fulvestrant, and AZD9496 with Estrogen Receptor Wild Type, Estrogen Receptor D538G Mutant, and Estrogen Receptor Y537S Mutant As shown in Table 10 below Compound 20 is comparably active or more active than GDC-810, Fulvestrant, and AZD9496 while having better potency, selectivity DMPK properties, safety, in vivo efficacy, and/or drug like properties. The IC50's collected in Example 10, Example 11, and Example 12 are compared in Table 10.

TABLE 10

$IC_{50}$ values of Select Compounds in $ER^{WT}$, $ER^{D538G}$, and $ER^{Y537S}$

| | $ER^{WT}$ (nM) | $ER^{D538G}$ (nM) | $ER^{Y537S}$ (nM) |
|---|---|---|---|
| Compound 20 | 2.1 | 15 | 56 |
| GDC-0810 | 11 | 25 | 1300 |
| Fulvestrant | 4.5 | 10.5 | 20 |
| AZD9496 | 0.45 | 1.2 | 2.6 |

Figure 10:
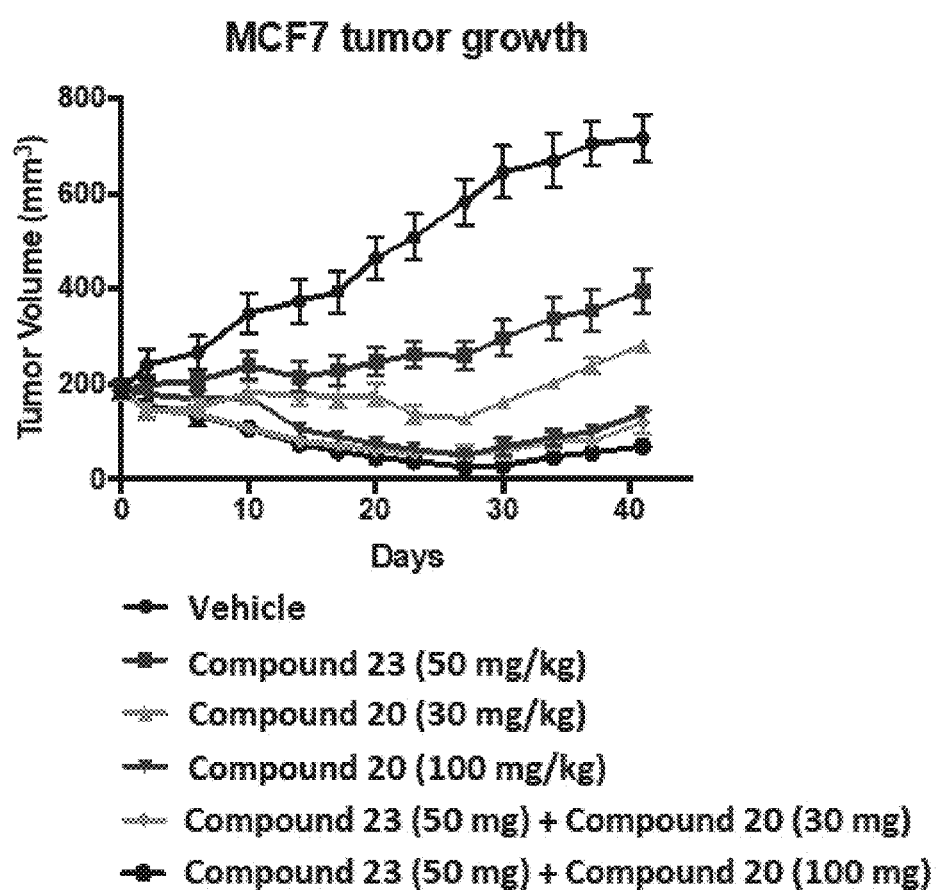
FIG. 10 is a graph of tumor volume in a MCF7 ER+ breast cancer model. Mice were administered either a daily oral dose of Compound 23 (50 mg/kg) alone, a daily oral dose of Compound 20 (30 mg/kg or 100 mg/kg) alone, or a daily oral dose of a combination of Compound 20 (30 mg/kg or 100 mg/kg) and Compound 23 (50 mg/kg). As discussed in Example 15, the combination of Compound 23 increases the efficacy of Compound 20. Statistics were one-way ANOVA and error bars are SEM. The x-axis is time measured in days and the y-axis is tumor volume measured in $mm^3$.
Figure 11:
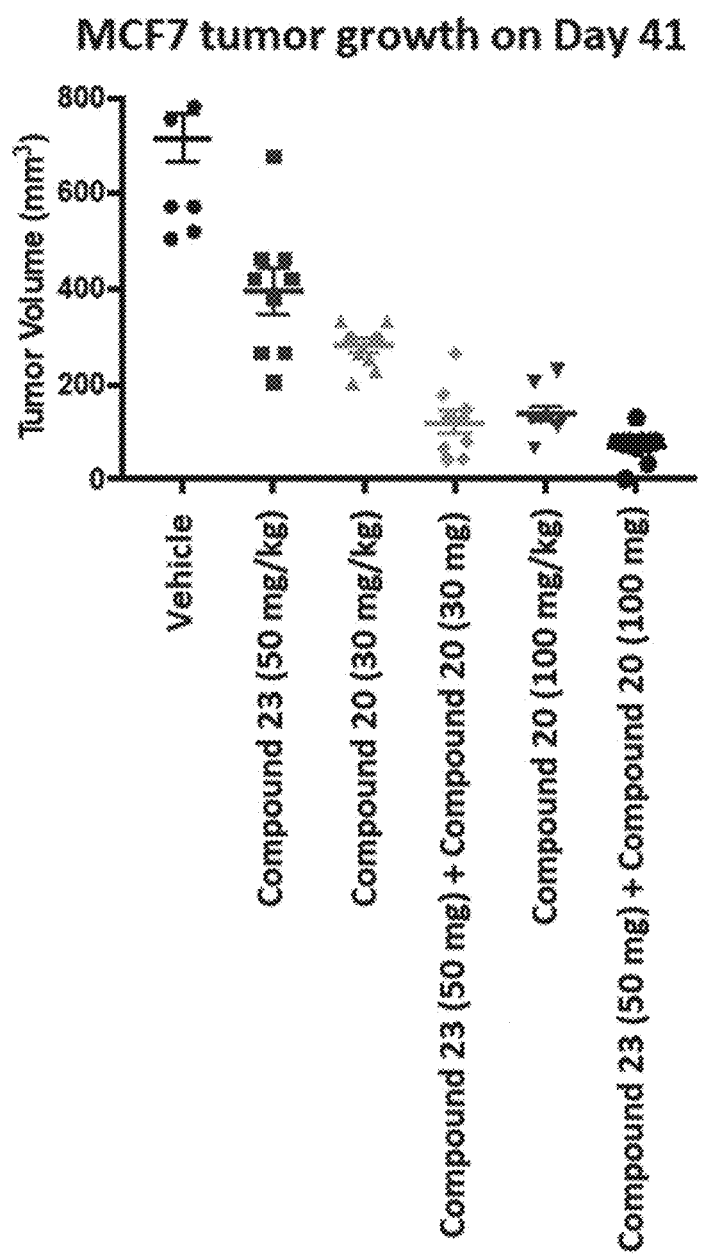
FIG. 11 is a graph of tumor volume in a MCF7 ER+ breast cancer model on day 41 of treatment with either a daily oral dose of Compound 23 (50 mg/kg) alone, a daily oral dose of Compound 20 (30 mg/kg or 100 mg/kg) alone, or a daily oral dose of a combination of Compound 20 (30 mg/kg or 100 mg/kg) and Compound 23 (50 mg/kg). As discussed in Example 15, the combination of Compound 23 increases the efficacy of Compound 20. Statistics were one-way ANOVA and error bars are SEM. The x-axis is labeled with the compound and dosing amount and the y-axis is the tumor volume measured in $mm^3$.

Example 15. Oral Compound 23 Increases Efficacy of Oral Compound 20 in MCF7 ER+ Breast Cancer Model In a MCF7 ER+ breast cancer model, administration of Compound 23 increased the efficacy of oral Compound 20. Mice were administered daily oral doses of Compound 23 (50 mg/kg), Compound 20 (30 mg/kg or 100 mg/kg), or a combination of Compound 20 (30 mg/kg or 100 mg/kg) and Compound 23 (50 mg/kg) for 28 days. Tumor volume was measured for approximately 41 days and dosing began on day 1. FIG. 10 shows the comparison of tumor volume decrease when 30 mg/kg of Compound 20 was administered alone and when 30 mg/kg of Compound 20 was administered in combination with Compound 23 (50 mg/kg). FIG. 10 also shows the comparison of tumor volume decrease when 100 mg/kg of Compound 20 was administered alone and when 100 mg/kg of Compound 20 was administered in combination with Compound 23 (50 mg/kg). In both cases, Compound 23 increased the efficacy of Compound 20. FIG. 11 shows the final tumor volume for each dose on day 41. The tumor volume decreased more when 30 mg/kg of Compound 20 was administered in combination with Compound 23 (50 mg/kg) compared to when 30 mg/kg of Compound 20 was administered alone. Similarly, the tumor volume decreased more when 100 mg/kg of Compound 20 was administered in combination with Compound 23 (50 mg/kg) compared to when 100 mg/kg of Compound 20 was administered alone. At both dosages of 100 mg/kg and 30 mg/kg, Compound 23 increased the efficacy of Compound 20.

Figure 12A:
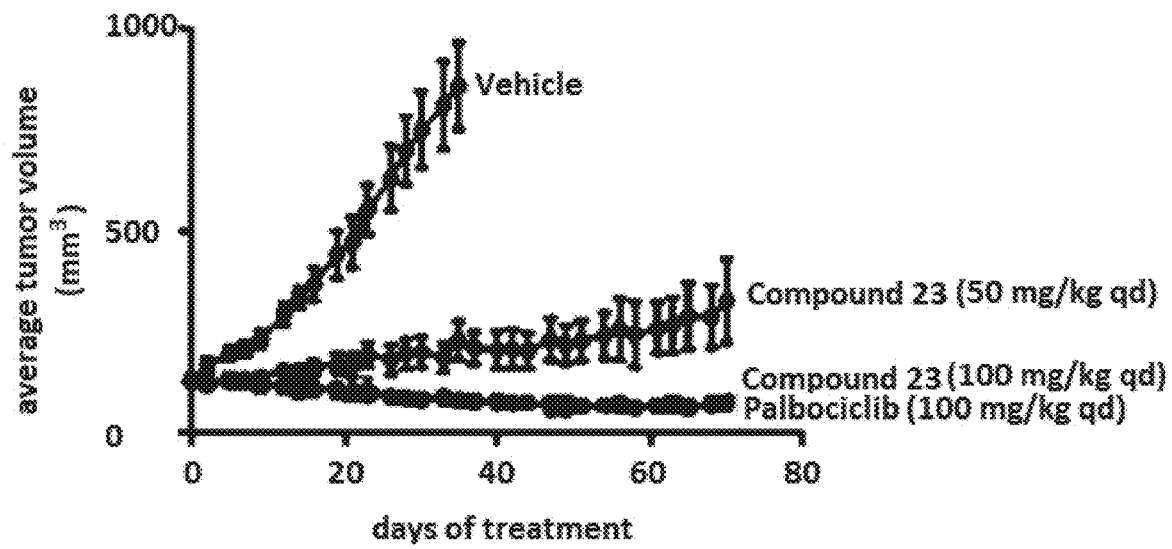
FIG. 12A is a graph measuring the inhibition of tumor volume following treatment with doses of Compound 23 (50 mg/kg qd or 100 mg/kg qd) compared to a dose of Palbociclib (100 mg/kg qd). As discussed in Example 16, the administration of Compound 23 at a dosage of 100 mg/kg qd was comparable in decreasing tumor volume to Palbociclib and both dosages were effective in decreasing tumor volume compared to the vehicle. The x-axis is treatment length measured in days and the y-axis is the average tumor volume measured in $mm^3$.
Figure 12B:
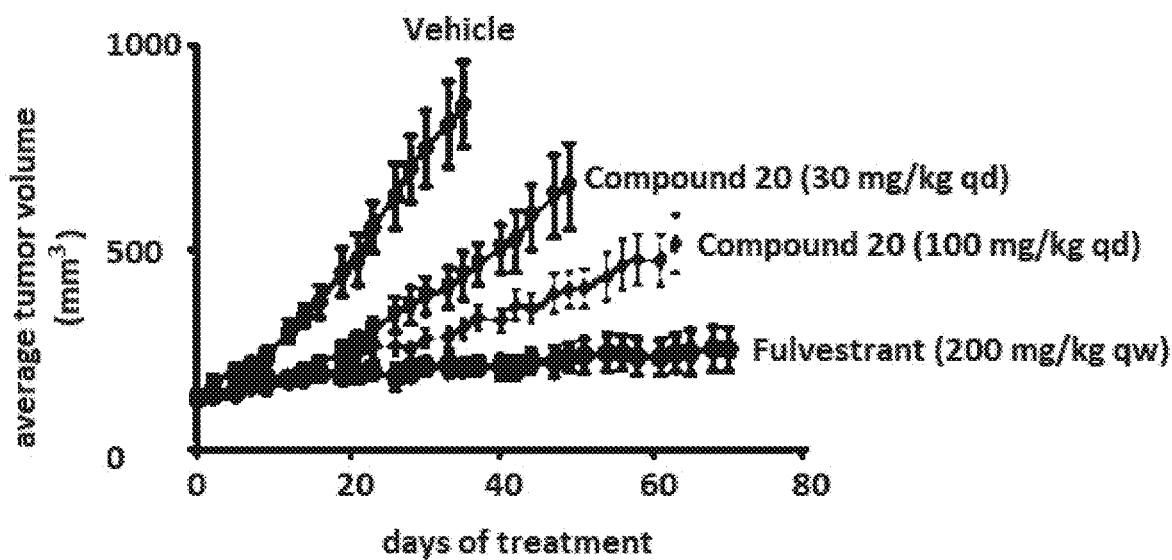
FIG. 12B is a graph measuring the inhibition of tumor volume following treatment with doses of Compound 20 (30 mg/kg qd or 100 mg/kg qd) compared to a dose of Fulvestrant (200 mg/kg qw). As discussed in Example 16, the administration of Compound 20 at both dosages was effective in decreasing tumor volume compared to the vehicle. The x-axis is treatment length measured in days and the y-axis is the average tumor volume measured in $mm^3$.

Example 16. Compound 20 and Compound 23 Both Inhibit the Growth of Tamoxifen-Resistant Xenograft Tumors Compound 20 and Compound 23 (FIGS. 12A and 12B) and the combination of Compound 20 and Compound 23 (FIGS. 12C and 12D) inhibited the growth of tamoxifen-resistant (TamR) xenograft tumors. As shown in FIG. 12A, single doses of Compound 23 (50 mg/kg administered once a day (qd) and 100 mg/kg once a day (qd)) decreased tumor volume when tumor volume was measured over the course of treatment (approximately 70 days). Compound 23 at a dose of 100 mg/kg given once a day was comparable to the administration of Palbociclib at a dose of 100 mg/kg given once a day. As shown in FIG. 12B, single doses of Compound 20 (30 mg/kg administered once a day and 100 mg/kg administered once a day) were effective in decreasing tumor volume over the course of treatment (approximately 70 days). The dosages of Compound 20 were compared to a dose of Fulvestrant (200 mg/kg once a week (qw)).

Figure 12C:
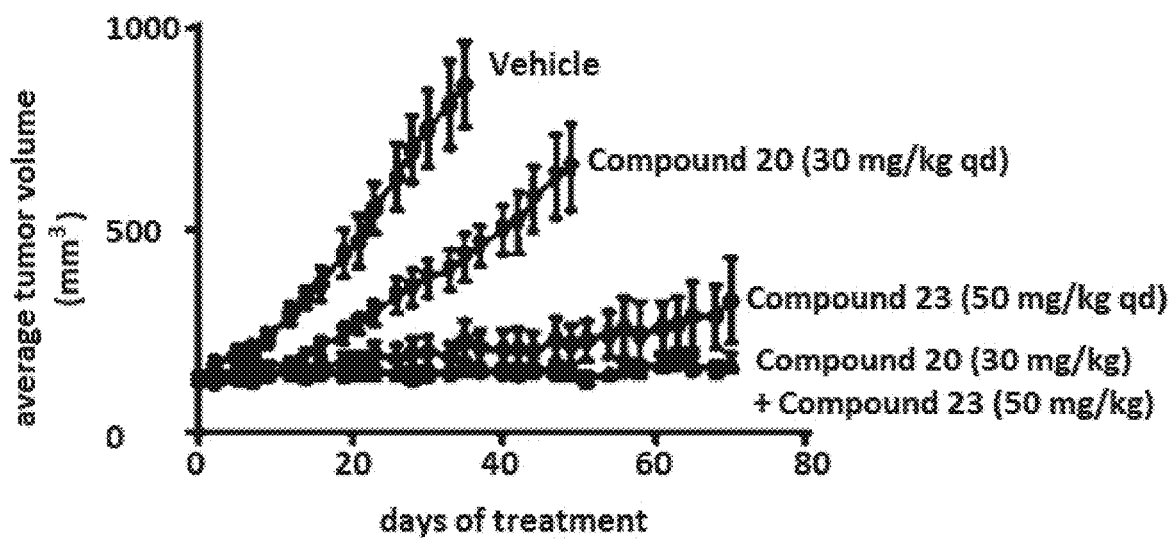
FIG. 12C is a graph measuring the inhibition of tumor volume following treatment with either Compound 20 (30 mg/kg qd), Compound 23 (50 mg/kg qd), or a combination of Compound 20 (30 mg/kg) and Compound 23 (50 mg/kg). As discussed in Example 16, the combination therapy was most effective in decreasing tumor volume compared to the administration of either Compound 20 or Compound 23 alone and Compound 23 increased the efficacy of Compound 20. The x-axis is treatment length measured in days and the y-axis is the average tumor volume measured in $mm^3$.
Figure 12D:
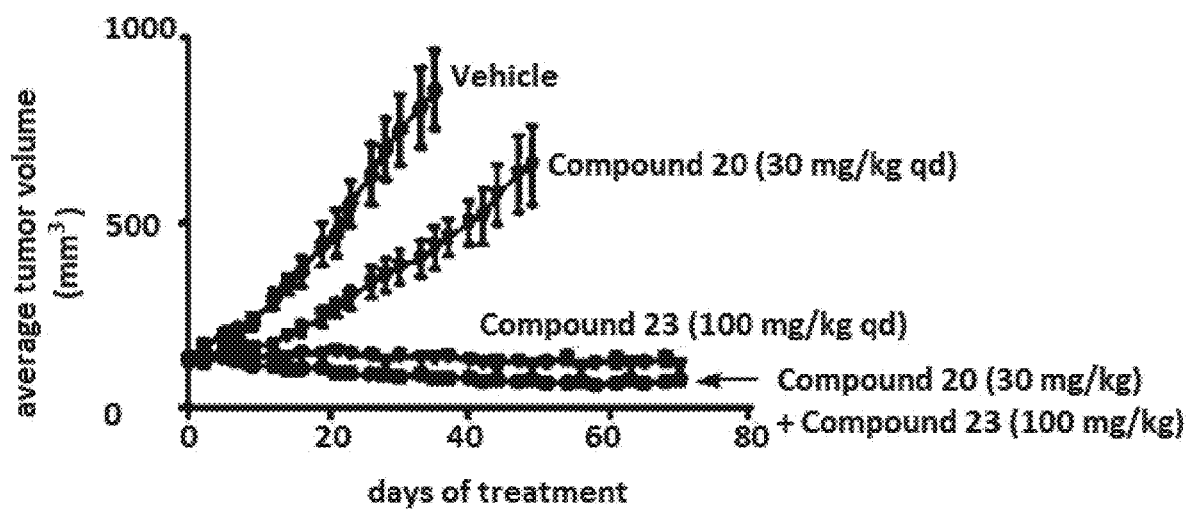
FIG. 12D is a graph measuring the inhibition of tumor volume following treatment with either Compound 20 (30 mg/kg qd), Compound 23 (100 mg/kg qd), or a combination of Compound 20 (30 mg/kg) and Compound 23 (100 mg/kg). As discussed in Example 16, the combination therapy was effective in decreasing tumor volume and Compound 23 increased the efficacy of Compound 20. The x-axis is treatment length measured in days and the y-axis is the average tumor volume measured in mm$^3$.

FIGS. 12C and 12D show the decrease in tumor volume of the course of a treatment of approximately 70 days comparing the administration of Compound 20 and Compound 23 alone and in combination. As shown in FIG. 12C, the combination of Compound 20 (30 mg/kg) and Compound 23 (50 mg/kg) was more effective in decreasing tumor volume than either Compound 30 (30 mg/kg qd) or Compound 23 (50 mg/kg qd) administered alone. Compound 23 was able to increase the efficacy of Compound 20. As shown in FIG. 12D, the combination of Compound 20 (30 mg/kg) and Compound 23 (100 mg/kg) was also effective in decreasing tumor volume and again, Compound 23 was able to increase the efficacy of Compound 20.

Example 17. Compound 20 Inhibits the Growth of LTED Xenograft Tumors in a Model of Aromatase Inhibitor Resistance LTED xenograft tumors in OVX nu/nu (ovariectomy nude) mice were responsive to single doses of Compound 20 as shown in FIG. 13. Mice were administered 5 mg/kg, 10 mg/kg, 30 mg/kg or 100 mg/kg of Compound 20 and the decrease in tumor volume correlated with the dose level as tumor volume was measured over the course of treatment (30 days).

Example 18. Evaluation of Compound 20 and Compound 23 Combination Therapy in $ESR1^{WT}$ and $ESR1^{Y537S}$ Breast Cancer In Vivo Compound 20, Compound 23, tamoxifen, fulvestrant, and palbociclib administered alone and in various combinations were evaluated against $ESR1^{WT}$ (estrogen receptor wild-type) breast cancer in vivo. The combination of Compound 20 and Compound 23, the combination of palbociclib and Compound 23, the combination of Compound 23 and fulvestrant, and the combination of fulvestrant and palbociclib were evaluated in the study. The dose, route of administration, and schedule for each compound is shown in Table 11. Dosing lasted for 28 days and tumor volume was measured past 70 days. FIG. 14A is a graph depicting the tumor volume decrease over the entire study and FIG. 14B is a graph depicting the tumor volume as measured on day 28 when dosing was complete. As shown in FIG. 14A, over the course of the study, the administration of Compound 23 increased the efficacy of fulvestrant and Compound 20. The combination of Compound 20 and palbociclib was also more effective in decreasing tumor volume over the course of the study compared to the administration of either Compound 20 or palbociclib alone. As shown in FIG. 14B, when the tumor volume was measured on day 28, the combination of Compound 20 and Compound 23 was more effective in decreasing tumor volume than the administration of either Compound 20 or Compound 23 alone. Similarly, Compound 20 increased the efficacy of palbociclib and Compound 23 increased the efficacy of fulvestrant when tumor volume was measured on the day that dosing was complete.

Compound 20 and Compound 23 administered alone and in combination were evaluated against ESR1$^{Y537S}$ breast cancer in vivo. The dose, route of administration, and schedule for each compound is shown in Table 5. Tumor volume was measured for 60 days (FIG. 15A). In ESR1$^{Y537S}$ breast cancer, Compound 23 (50 mg/kg) increased the efficacy of Compound 20 when Compound 20 was administered at a dose of 30 mg/kg and at a dose of 100 mg/kg. As shown in FIG. 15B, when the tumor volume was measured on day 33, the combination of Compound 20 and Compound 23 (59 mg/kg) was effective in decreasing tumor volume when Compound 20 was administered at a dose of 30 mg/kg and 100 mg/kg.

TABLE 11

Dose amount, route of administration, and schedule of compounds for ESR1$^{WT}$ and ESR1$^{Y537S}$ breast cancer study

| Compound | Dose | Route of Administration | Schedule |
|---|---|---|---|
| ESR1$^{WT}$ Breast Cancer Study | | | |
| Compound 23 | 50 mg/kg | Oral | Once a day × 28 |
| Palbociclib | 50 mg/kg | Oral | Once a day × 28 |
| Compound 20 | 100 mg/kg | Oral | Once a day × 28 |
| Fulvestrant | 5 mg/animal | Subcutaneous | weekly × 4 |
| ESR1$^{Y537S}$ Breast Cancer Study | | | |
| Compound 23 | 50 mg/kg | Oral | Once a day to end |
| Compound 20 | 30 or 100 mg/kg | Oral | Once a day to end |
| Fulvestrant | 5 mg/animal | Subcutaneous | weekly to end |

This specification has been described with reference to embodiments of the invention. However, one of ordinary skill in the art will appreciate that various modifications and changes can be made without departing from the scope of the invention as set forth in the claims below. While only certain representative materials, methods, and aspects of these materials and methods are specifically described, other materials and methods and combinations of various features of the materials and methods are intended to fall within the scope of the appended claims, as if specifically recited. Accordingly, the specification is to be regarded in an illustrative rather than a restrictive sense, and all such modifications are intended to be included within the scope of invention.

We claim:

1. A method of treating an estrogen-related cancer or tumor in a human comprising administering to the human in need thereof a therapeutically effective amount of a SERD in combination with a therapeutically effective amount of a CDK4/6 inhibitor, wherein the SERD is selected from:

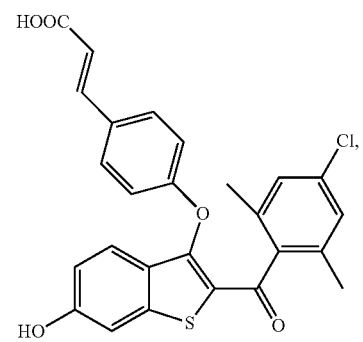

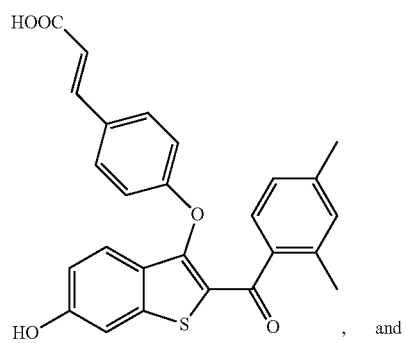
, and

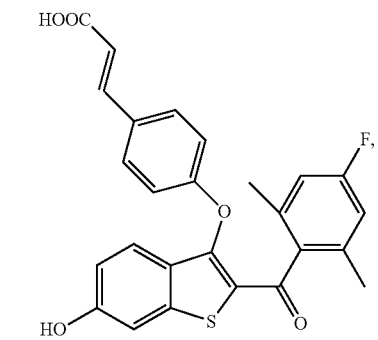

or a pharmaceutically acceptable salt thereof, and wherein the CDK4/6 inhibitor is selected from:

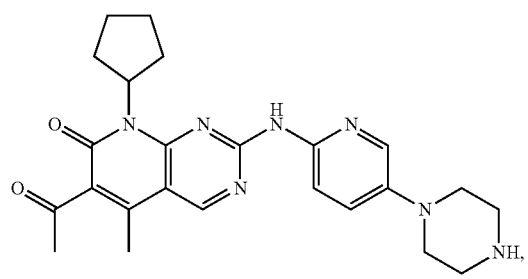

-continued

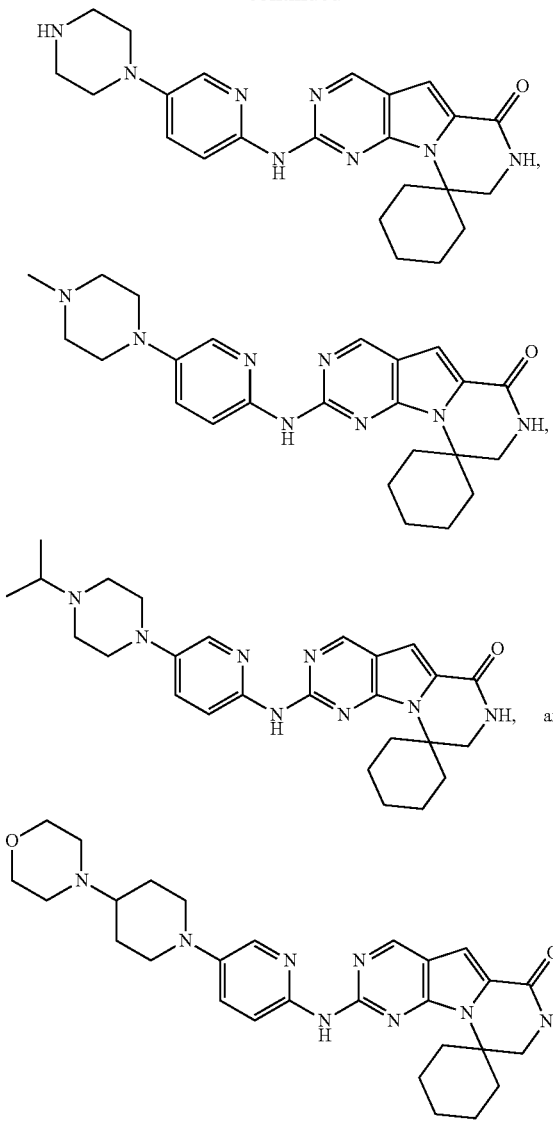

or a pharmaceutically acceptable salt thereof; wherein the estrogen-related cancer or tumor is breast cancer, ovarian cancer, endometrial cancer, kidney cancer, uterine cancer, prostate cancer, or lung cancer.

2. The method of claim 1, wherein the estrogen-related cancer is metastatic endocrine therapy resistant breast cancer.

3. The method of claim 1, wherein the cancer is breast cancer.

4. The method of claim 3, wherein the breast cancer is hormone receptor positive metastatic breast cancer.

5. The method of claim 3, wherein the breast cancer is a tamoxifen resistant breast cancer.

6. The method of claim 3, wherein the breast cancer is a triple negative breast cancer.

7. The method of claim 1, wherein the human is further administered another chemotherapeutic agent in combination or alternation with the SERD and the CDK4/6 inhibitor.

8. The method of claim 1, wherein the SERD is

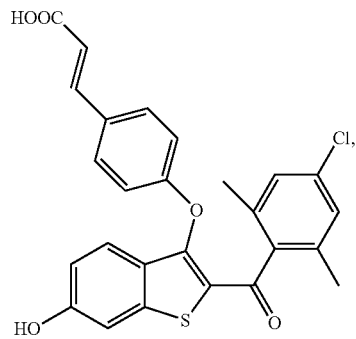 [SMILES: Cc1cc(Cl)cc(C)c1C(=O)c1sc2cc(O)ccc2c1Oc1ccc(/C=C/C(=O)O)cc1]

or a pharmaceutically acceptable salt thereof.

9. The method of claim 1, wherein the SERD is

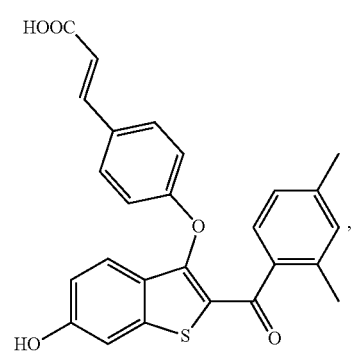

or a pharmaceutically acceptable salt thereof.

10. The method of claim 1, wherein the SERD is

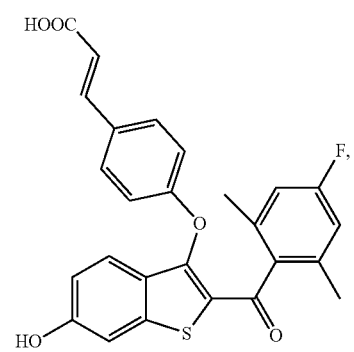

or a pharmaceutically acceptable salt thereof.

11. The method of claim 1, wherein the CDK4/6 inhibitor is

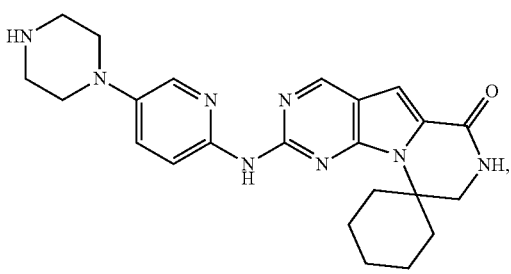 [SMILES: O=C1NCC2(CCCCC2)n2c1cc1cnc(Nc3ccc(N4CCNCC4)cn3)nc12]

or a pharmaceutically acceptable salt thereof.

12. The method of claim 1, wherein the CDK4/6 inhibitor is

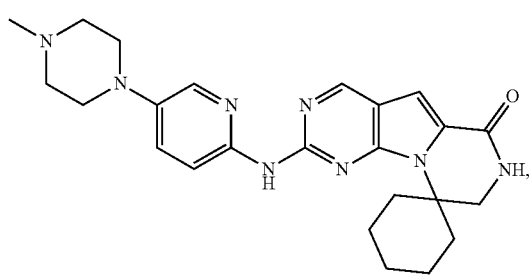 [SMILES: CN1CCN(c2ccc(Nc3ncc4cc5n(c4n3)C3(CCCCC3)CNC5=O)nc2)CC1]

or a pharmaceutically acceptable salt thereof.

13. The method of claim 1, wherein the CDK4/6 inhibitor is

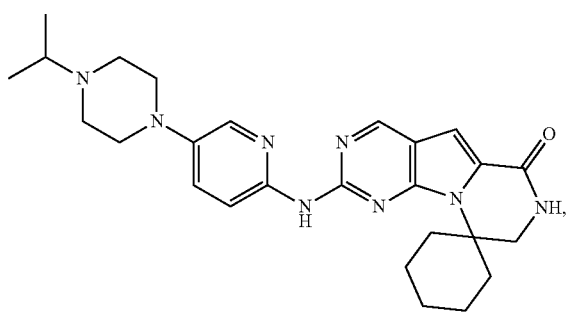 [SMILES: CC(C)N1CCN(c2ccc(Nc3ncc4cc5n(c4n3)C3(CCCCC3)CNC5=O)nc2)CC1]

or a pharmaceutically acceptable salt thereof.

14. The method of claim 1, wherein the CDK4/6 inhibitor is

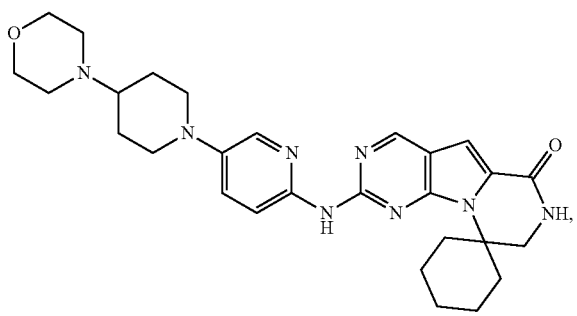 [SMILES: O=C1NCC2(CCCCC2)n2c1cc1cnc(Nc3ccc(N4CCC(N5CCOCC5)CC4)cn3)nc12]

or a pharmaceutically acceptable salt thereof.

15. The method of claim 1, wherein the SERD is

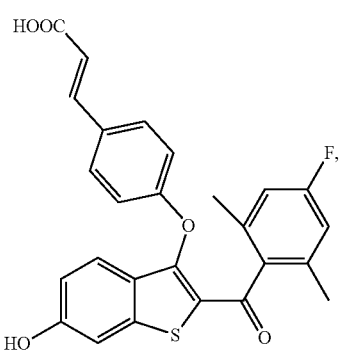 [SMILES: Cc1cc(F)cc(C)c1C(=O)c1sc2cc(O)ccc2c1Oc1ccc(/C=C/C(=O)O)cc1]

or a pharmaceutically acceptable salt thereof, and the CDK4/6 inhibitor is

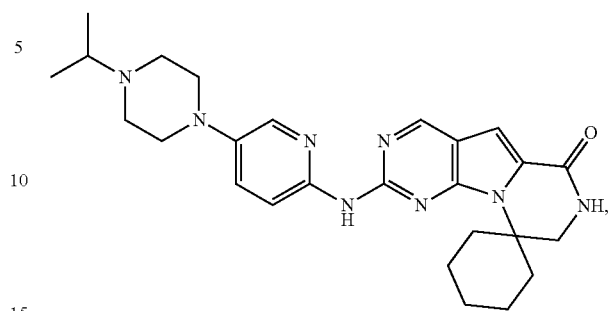

or a pharmaceutically acceptable salt thereof.

16. The method of claim 1, wherein the CDK4/6 inhibitor is

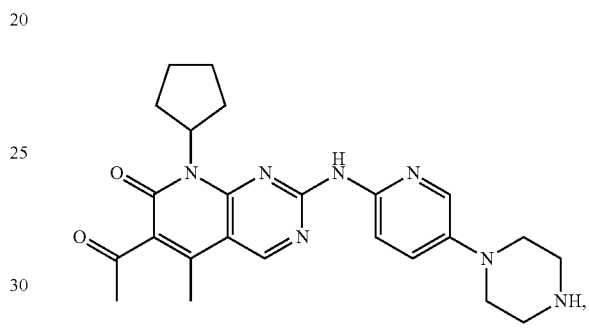

or a pharmaceutically acceptable salt thereof.

17. The method of claim 16, wherein the SERD is

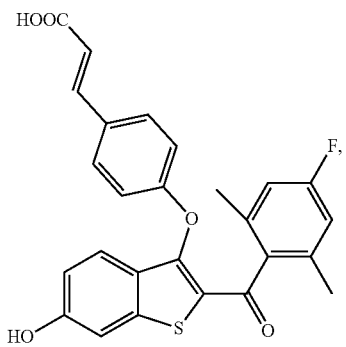

or a pharmaceutically acceptable salt thereof.

18. The method of claim 17, wherein the estrogen-related cancer is metastatic endocrine therapy resistant breast cancer.

19. The method of claim 17, wherein the cancer is breast cancer.

20. The method of claim 19, wherein the breast cancer is hormone receptor positive metastatic breast cancer.

21. The method of claim 19, wherein the breast cancer is a tamoxifen resistant breast cancer.

22. The method of claim 17, wherein the human is further administered another chemotherapeutic agent in combination or alternation with the SERD and the CDK4/6 inhibitor.

23. A pharmaceutical composition comprising a SERD, a CDK4/6 inhibitor, and a pharmaceutically acceptable carrier, wherein the SERD is selected from:

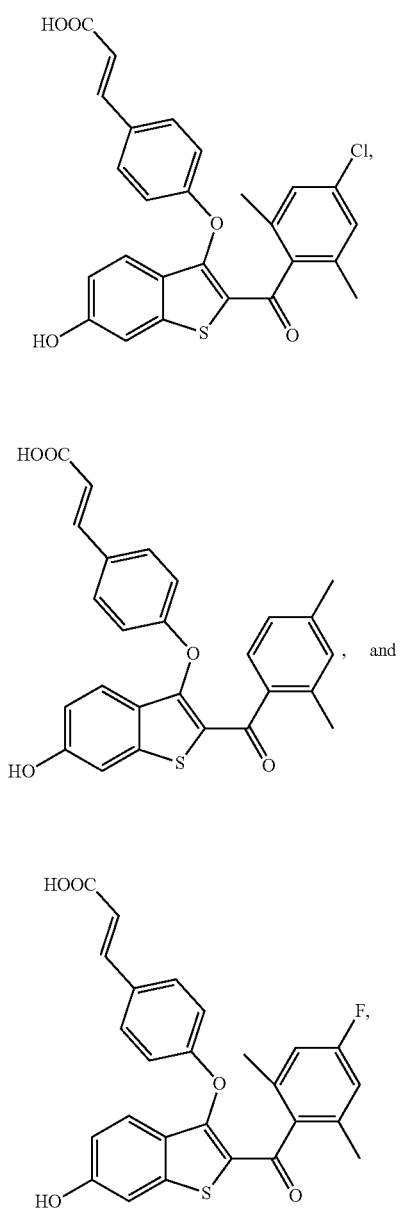

, and or a pharmaceutically acceptable salt thereof,
and wherein the CDK4/6 inhibitor is selected from:

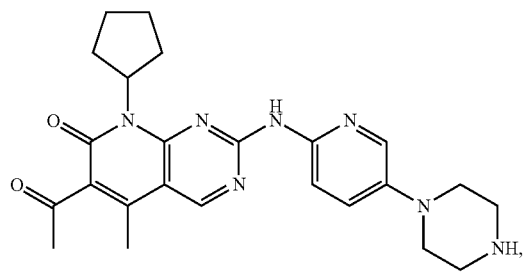 [SMILES: CC(=O)c1c(C)c2cnc(Nc3ccc(N4CCNCC4)cn3)nc2n(C2CCCC2)c1=O]

-continued

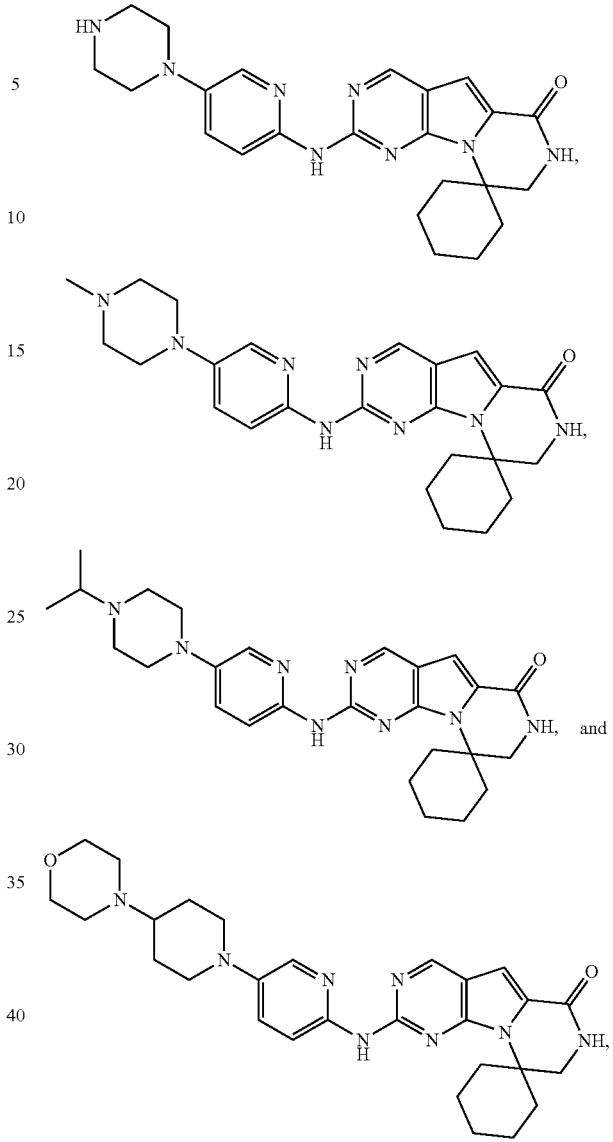

, and or a pharmaceutically acceptable salt thereof.

24. The pharmaceutical composition of claim 23, wherein the SERD is

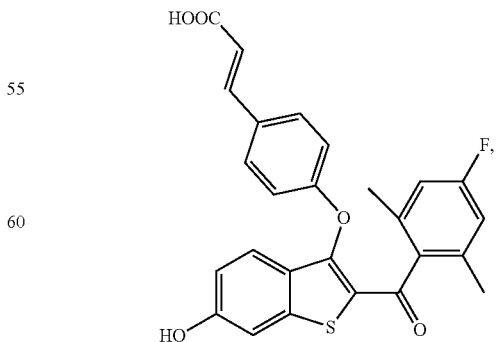

or a pharmaceutically acceptable salt thereof.

25. The pharmaceutical composition of claim 23, wherein the SERD is

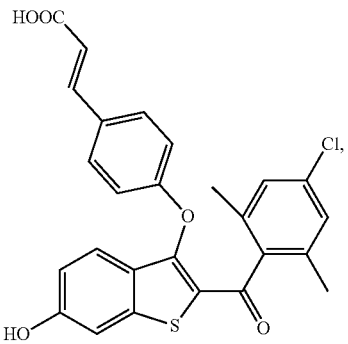 [SMILES: Cc1cc(Cl)cc(C)c1C(=O)c1sc2cc(O)ccc2c1Oc1ccc(/C=C/C(=O)O)cc1]

or a pharmaceutically acceptable salt thereof.

26. The pharmaceutical composition of claim 23, wherein the SERD is

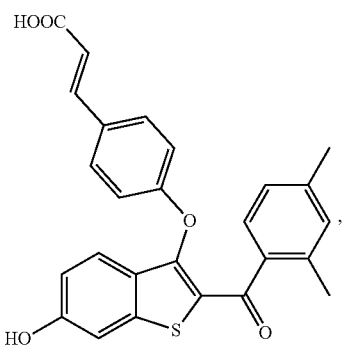 [SMILES: Cc1ccc(C(=O)c2sc3cc(O)ccc3c2Oc2ccc(/C=C/C(=O)O)cc2)c(C)c1]

or a pharmaceutically acceptable salt thereof.

27. The pharmaceutical composition of claim 23, wherein the SERD is

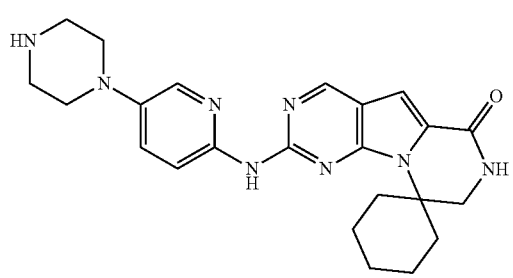 [SMILES: O=C1NCC2(CCCCC2)n2c1cc1cnc(Nc3ccc(N4CCNCC4)cn3)nc12]

or a pharmaceutically acceptable salt thereof.

28. The pharmaceutical composition of claim 23, wherein the CDK4/6 inhibitor is

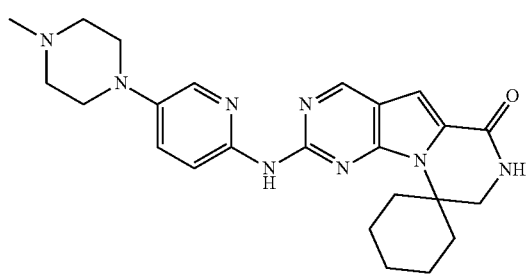 [SMILES: CN1CCN(c2ccc(Nc3ncc4cc5n(c4n3)C3(CCCCC3)CNC5=O)nc2)CC1]

or a pharmaceutically acceptable salt thereof.

29. The pharmaceutical composition of claim 23, wherein the CDK4/6 inhibitor is

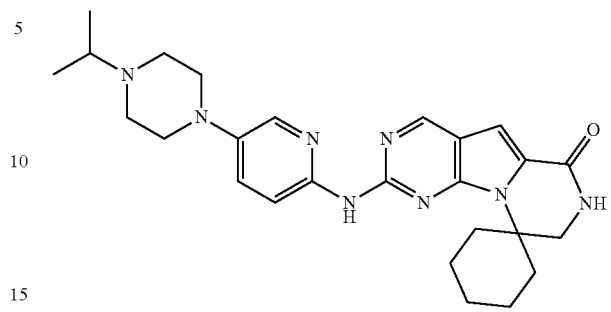

or a pharmaceutically acceptable salt thereof.

30. The pharmaceutical composition of claim 23, wherein the CDK4/6 inhibitor is

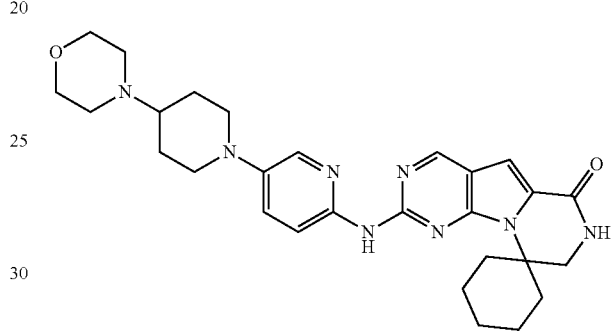

or a pharmaceutically acceptable salt thereof.

31. A pharmaceutical composition comprising:
  (i) a compound of structure:

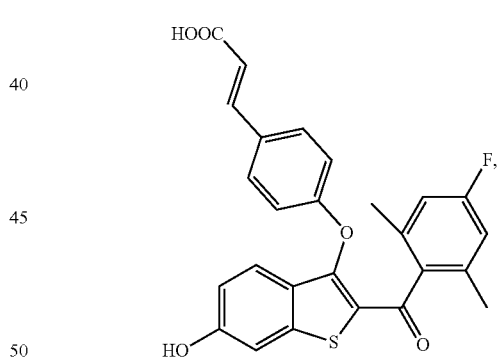

or a pharmaceutically acceptable salt thereof;
  (ii) a compound of structure:

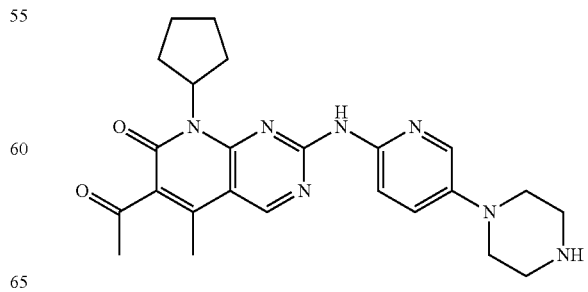

or a pharmaceutically acceptable salt thereof; and
  (iii) a pharmaceutically acceptable carrier.

32. A combination comprising a therapeutically effective amount of a SERD and a CDK4/6 inhibitor;
wherein the SERD is selected from:
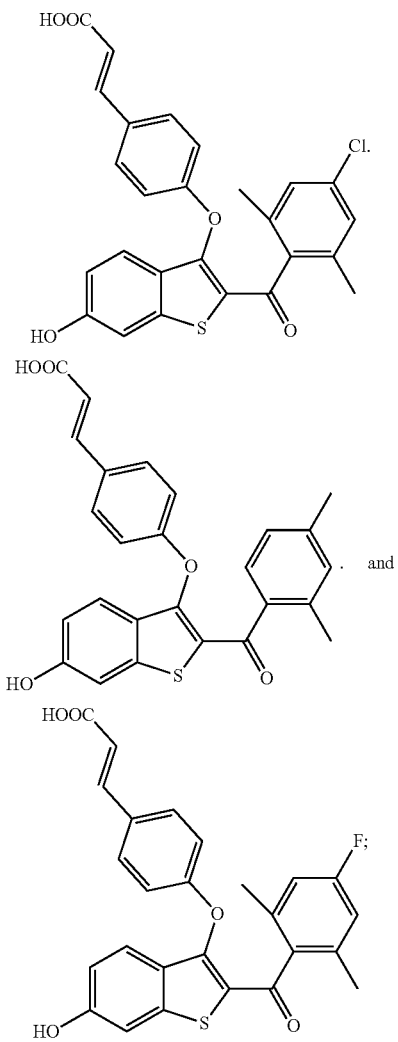
or a pharmaceutically acceptable salt thereof,
and wherein the CDK4/6 inhibitor is selected from:
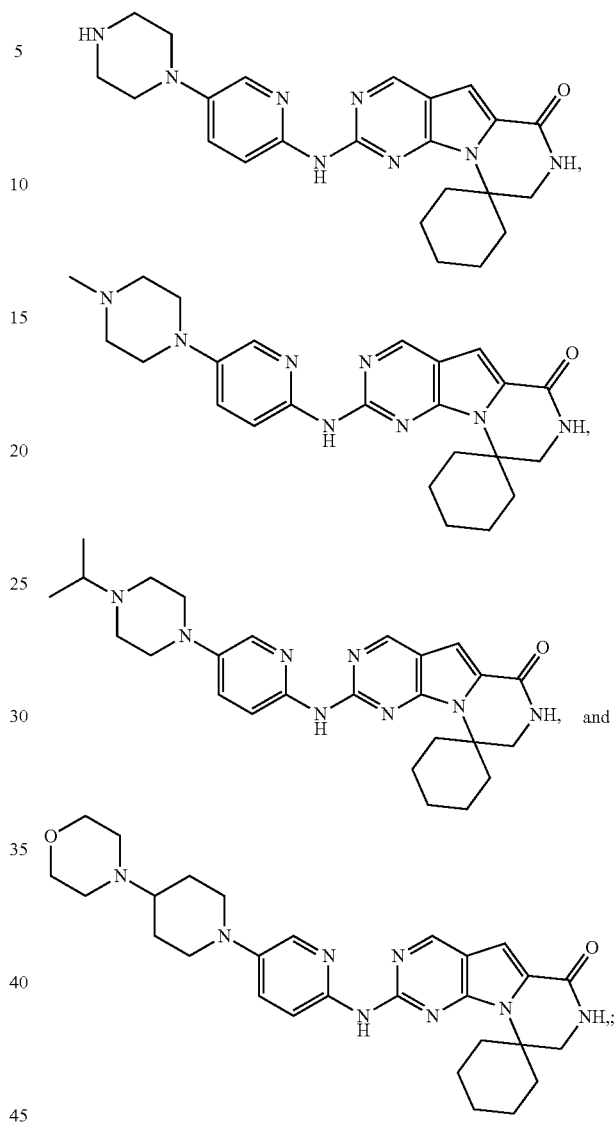
or a pharmaceutically acceptable salt thereof.
* * * * *